United States Patent
Garvin et al.

(10) Patent No.: US 7,563,598 B2
(45) Date of Patent: Jul. 21, 2009

(54) DETECTION OF TRUNCATION MUTATIONS BY MASS SPECTROMETRY

(75) Inventors: Alex Garvin, Durmenach (FR);
Sadanand Gite, Cambridge, MA (US);
Vladislav Bergo, Boston, MA (US);
Kenneth Rothschild, Newton, MA (US)

(73) Assignee: Ambergen, Inc., Watertown, MA (US)

( * ) Notice: Subject to any disclaimer, the term of this patent is extended or adjusted under 35 U.S.C. 154(b) by 0 days.

(21) Appl. No.: 11/487,128

(22) Filed: Jul. 14, 2006

(65) Prior Publication Data

US 2007/0072214 A1 Mar. 29, 2007

Related U.S. Application Data

(63) Continuation-in-part of application No. PCT/US2005/026895, filed on Jul. 28, 2005, which is a continuation of application No. 10/903,612, filed on Jul. 30, 2004.

(51) Int. Cl.
*C12P 21/06* (2006.01)
(52) U.S. Cl. .................. 435/69.1; 435/219
(58) Field of Classification Search ................ None
See application file for complete search history.

(56) References Cited

U.S. PATENT DOCUMENTS 6,207,370 B1 * 3/2001 Little et al. .................. 435/6
6,322,970 B1 * 11/2001 Little et al. .................. 506/6

OTHER PUBLICATIONS

Charebois et al (Electron Capture Dissociation and 13C, 15N Depletion for Deuterium Localization in Intact Proteins after Solution-Phase Exchange. Analytical Chemistry, 2003. 75(13):3263-3266).*
Spirin (High-Throughput cell-free systems for synthesis of functionally active proteins. Trends in Biotechnology, 2004. 22(10):538-545).*
Genbank accession No. P61864. Yeast Ubiquitin.*
Xiong et al (Improved Mass Analysis of Oligoribonucleotides by 13C, 15C Double Depletion and Electrospray Ionization FT-ICR Mass Spec, Analytical Chemistry, 2004. 76(6):1804-1809).*
Shimizu et al Nature Biotechnology 19:751-755, 2001.*
Marshall et al (J. Am. Chem. Soc., 119 (2), 433-434, 1997.*

* cited by examiner

*Primary Examiner*—Deborah Crouch
(74) *Attorney, Agent, or Firm*—Medlen & Carroll, LLP

(57) ABSTRACT

This invention relates to the detection and analysis by mass spec of nascent proteins, and in particular truncated proteins, translated within cellular or cell-free translation systems. N-terminal and C-terminal epitopes introduced into these nascent proteins permit rapid and efficient isolation, as well as a mass difference.

6 Claims, 58 Drawing Sheets

⁻OOC–ALANINE-VALINE-TYROSINE-LYSINE-TRYPTOPHAN–NH$_3$+

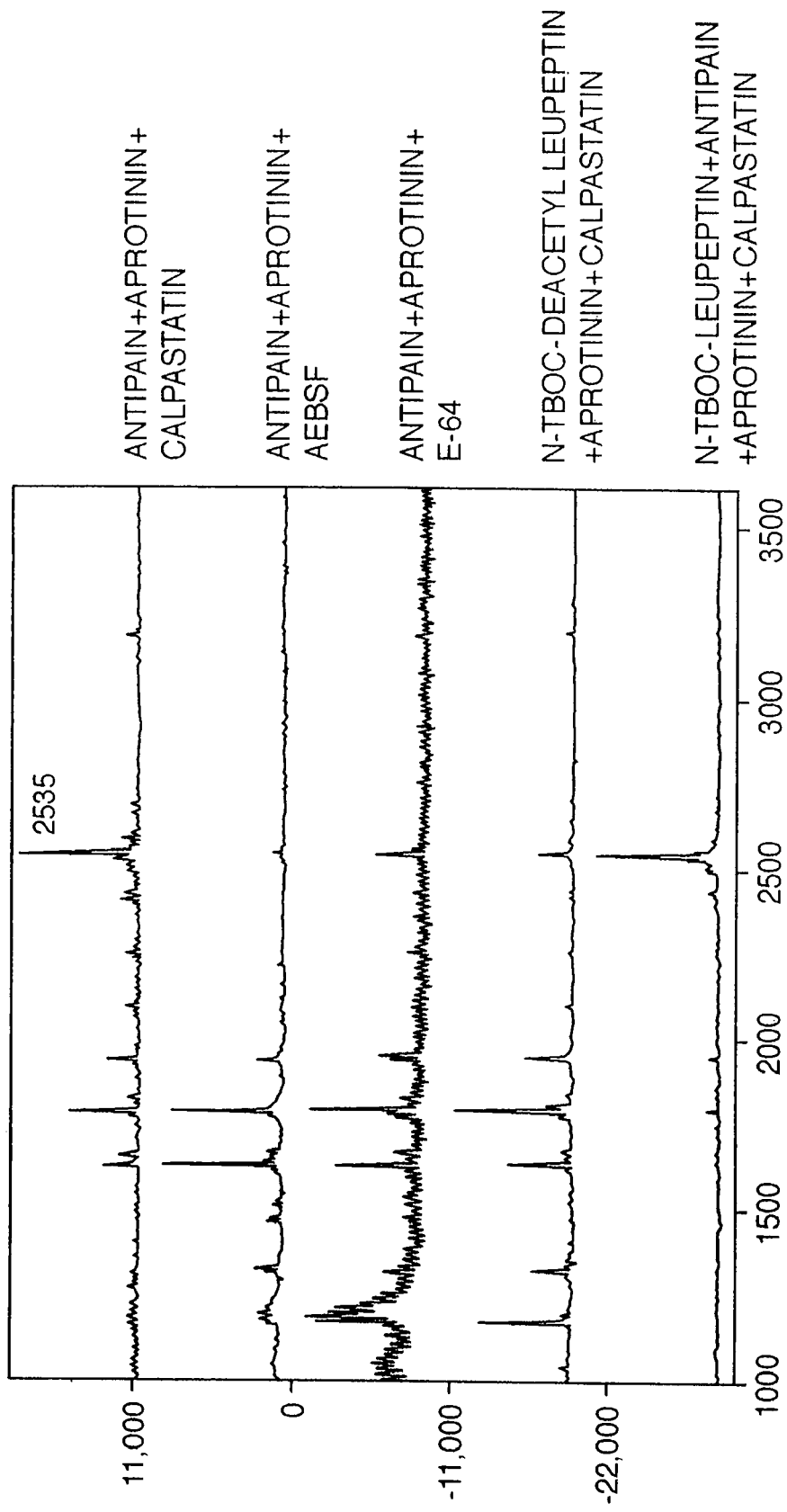

DETECTION OF TRUNCATION MUTATIONS BY MASS SPECTROMETRY

This is a Continuation In Part of co-pending application(s) PCT/US2005/026895 filed on Jul. 28, 2005 which is a Continuation of pending application Ser. No. 10/903,612 filed on Jul. 30, 2004.

FIELD OF THE INVENTION

This invention relates to assays and markers that facilitate the detection and analysis of nascent proteins translated within cellular or cell-free translation systems. Nascent proteins (and in particular, truncated proteins) containing these markers can be rapidly and efficiently detected and analyzed by mass spectrometry.

BACKGROUND OF THE INVENTION

Detection of mutations is an increasingly important area in clinical diagnosis, including but not limited to the diagnosis of cancer and/or individuals disposed to cancer. The protein truncation test (PTT) is a technique for the detection of nonsense and frameshift mutations which lead to the generation of truncated protein products. Genes associated with Duchenne muscular dystrophy, adenomatous polyposis coli, human mutL homologue and human nutS homologue (both involved in colon cancer), and BRAC1 (involved in familial breast cancer) can now be screened for mutations in this manner, along with others.

Typically, the PTT technique involves the incorporation of a T7 promoter site, ribosome binding site, and an artificial methionine start site into a PCR product covering the region of the gene to be investigated. The PCR product is then transcribed and translated using a cell-free translation system, such as an in vitro rabbit reticulocyte lysate, wheat germ lysate or *E. coli* lysate system, to generate a protein corresponding to the region of the gene amplified. The presence of a stop codon in the sequence, generated by a nonsense mutation or a frameshift, will result in the premature termination of protein translation, producing a truncated protein that can be detected by standard gel electrophoresis (e.g. SDS-PAGE) analysis combined with radioactive detection.

There are drawbacks to the technique as currently practiced. One of the most important problems involves the identification of the product of interest. This is made difficult because of nonspecific radiolabeled products. Attempts to address these problems have been made. One approach is to introduce an affinity tag after the start site and before the region encoding the gene of interest. See Rowan and Bodmer, "Introduction of a myc Reporter Taq to Improve the Quality of Mutation Detection Using the Protein Truncation Test," *Human Mutation* 9:172 (1997). However, such approaches still have the disadvantage that they rely on electrophoresis.

SUMMARY OF THE INVENTION

The present invention contemplates an assay wherein two or three markers (preferably N-terminal and C-terminal epitopes) are introduced into the nascent protein and the resulting wild-type and mutant proteins are detected by mass spectrometry. In a preferred embodiment of the invention, the novel compositions and methods are directed to the detection of frameshift or chain terminating mutations associated with disease. It is not intended that the present invention be limited to detecting mutations to only one particular disease. A variety of diseases are linked to such mutations (see Table 1) and are, therefore, contemplated.

In order to detect such mutations, a nascent protein (typically a portion of a gene product, wherein the portion is between 5 and 200 amino acids in length, and more commonly between 5 and 100 amino acids in length, and more preferably between 5 and around 60 amino acids in length— so that one can work in the size range that corresponds to optimal sensitivity on most mass spectrometry equipment) is (in one embodiment) first synthesized in a cell-free or cellular translation system from message RNA or DNA coding for the protein which may contain a possible mutation. The nascent protein is then separated from the cell-free or cellular translation system using the N-terminal epitope (located at or close to the N-terminal end of the protein). The resulting isolated material (which may contain both wild-type and truncated peptides) is then analyzed by mass spectrometry. Detection of a peak in the mass spectrum with a mass correlating with a peptide having the marker/epitope located at or close to the C-terminal of the protein (C-terminal epitope) indicate the wild-type peptide. Detection of a peak in the mass spectrum with a mass correlating with a peptide lacking a C-terminal marker indicates a truncating mutation. To enhance sensitivity, the C-terminal epitope in some embodiments can be used (prior to mass spec) to deplete wild-type sequences (i.e. enrich for truncated proteins) by interacting with a ligand (e.g. an antibody) directed to the C-terminal epitope (e.g. affinity chromatography). Alternative methods of depleting wild type sequence are also contemplated involving the using of an affinity tag incorporated by a misaminoacylated tRNA. In one embodiment, a biotin tag is incorporated in a sequence at or near the C-terminal end. This tag can be used in conjunction with streptavidin coated media to deplete a wild-type sequence.

In yet another embodiment, epitopes are designed into the resulting peptides to add mass. In one embodiment, the reverse primer may comprise codons corresponding to an epitope at the C-terminus. For example, the reverse primer may comprise the codons TGC GTA GTC TGG TAC GTC GTA TGG GTA corresponding to the protein sequence YPY-DVPDYA at the C-terminus ("the HA tag"). The HA tag is present in wild-type peptides only. It allows separation of wild-type and mutant peptides by means of affinity chromatography. Furthermore, it provides additional mass separation of at least 1102 Da between the wild-type and mutant signals, which results in enhanced spectral detection of mutant peptides.

In most cases, it is expected that the wild-type polypeptides will be present in a greater amount that the truncated polypeptides. Nonetheless, the present invention contemplates methods where the truncated polypeptide is readily detected by mass spectrometry. In one embodiment, the present invention contemplates a method, comprising: providing a preparation comprising wild type polypeptides and truncated polypeptides (preferably made in an in vitro translation reaction) in a ratio of at least 10:1, wherein said truncated polypeptides are due to a genetic mutation and are between 10 and 100 amino acids in length (but more typically between 20 and 80 amino acids in length, and more conveniently between 30 and 60 amino acids in length); and determining the molecular mass of said truncated polypeptides by mass spectrometry (experiments have shown that polypeptides less than 40 amino acids in length generate sufficient signal intensity for high sensitivity detection). In some embodiments, the said wild type polypeptides and said truncated polypeptides are in a ratio of at least 50:1. In still other embodiments, said wild type polypeptides and said truncated polypeptides are in a ratio of at least 100:1. In a preferred embodiment, the method further comprising the step of removing at least a portion of said wild type polypeptides from said preparation prior to step (b). In a particularly preferred embodiment, said wild type polypeptides comprises a C-terminal epitope and said removing is achieved by exposing said preparation to a ligand with affinity for said C-terminal epitope. It is preferred that at least a portion of each of said wild-type polypeptides is identical to a portion of a disease-related gene product (e.g. APC gene product).

The creation of a stop codon from a frameshift mutation is random. Where a stop codon is created, there is a significant difference in mass between the proteins containing both the C-terminal marker and N-terminal marker (i.e. wild-type proteins) and the truncated proteins containing only the N-terminal marker. On the other hand, it is possible that a frameshift mutation near the C-terminus will not result in stop codon. In a preferred embodiment, to ensure that full advantage is taken of this mass difference, a sequence (discussed below) is introduced adjacent the C-terminal epitope which will generate a stop codon if there is a frameshift. Such an approach does not rely on the random formation of stop codons.

In a preferred embodiment, mass spectrometry provides information about the fraction of nascent proteins containing frameshift or chain terminating mutations in the gene sequence coding for the nascent protein. The amount of wild-type sequence (i.e. protein containing the C-terminal epitope) reflects the fraction of protein which did not contain chain terminating or out-of-frame mutations.

Separating the protein(s) from the translation mixture (prior to mass spectrometry) using an affinity marker located at or close to the N-terminal end of the protein eliminates the occurrence of false starts which can occur when the protein is initiated during translation from an internal AUG in the coding region of the message. A false start can lead to erroneous results since it can occur after the chain terminating or out-of-frame mutation. This is especially true if the internal AUG is in-frame with the message. In this case, the peptide C-terminal marker will still be present even if message contains a mutation.

It is not intended that the present invention be limited to the source of nucleic acid. A variety of sources are contemplated (e.g. tissue samples from a biopsy), including but not limited to nucleic acid from blood and stool samples. Humans of all ages can be so tested in a relatively non-invasive manner. Both the existence of disease and the predisposition to disease can be tested. For example, in one embodiment, the present invention contemplates both pre-natal (e.g. amniotic fluid) and post-natal testing to determine predisposition to disease.

The present invention overcomes the problems and disadvantages associated with current strategies and designs and provides methods for the labeling, isolation, detection, quantitation, and analysis of nascent proteins produced in a cell-free or cellular translation system without the use of gels or radioactive labels.

It is not intended that the present invention be limited to a particular translation system. In one embodiment, a cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof. In a preferred embodiment, the system is a cell-free translation system that has been reconstituted with purified components (e.g. initiation factors, elongation factors, termination factors, aminoacyl-tRNA synthetase, methionyl-tRNA transformylase). See Y. Shimizu et al., "Cell-free translation reconstituted with purified components," *Nature Biotechnology* 19:751 (2001). See also U.S. patent application Ser. No. 983067, filed Oct. 23, 2001, hereby incorporated by reference.

While it is not intended that the present invention be limited to the particular reaction conditions employed, some parameters need to be kept in mind. Typically the cell-free translation system is incubated at a temperature of between about 25° C. to about 45° C. (and preferably 37° C.). Importantly, it has been found that all commercially available translation systems (including the reconstituted systems advertised as protease-free) have significant protease activity. Certain protease inhibitors (discussed below) can be used to reduce this protease activity—without significantly interfering with translation. Steps can be taken to directly remove proteases (e.g. by immunoprecipitation with specific antibodies or substrates). In addition, replacement of the ribosome component with more highly purified ribosomes can reduce protease activity. However, even with protease inhibitors and more purified components, exposure of the nascent protein to the translation mixture for extended periods of time (e.g. an hour) is generally to be avoided.

To ensure that proteases are not complicating the analysis (e.g. causing false negatives by proteolyzing the truncated peptides or causing false positives by proteolyzing the wild-type peptides), the present invention contemplates the use of a control or reference peptide that is "protease sensitive," i.e. sensitive to the protease activity of the particular translation system (the protease activity of various systems is described herein) such that partial protease digestion, e.g. at least 20% (and more typically between 40-60%) of the peptides in the population have had one or more amino acids removed, can be observed after 10 minutes of exposure (or less) to the translation mixture at 37° C. Quantitation can be approximated simply by comparing peak heights in the mass spectrum, with the understanding that factors influencing peak height will be similar (but not identical) for the digested and undigested peptides. Quantitation can be better approximated by using an undigested control (i.e. a peptide that has not been exposed to the translation mixture); however, adding the control to the sample can complicate the analysis unless steps are taken to create a control that has a mass that is distinct from undigested peptide (which has been exposed to the translation mixture but was not proteolyzed). In one embodiment, the control is an isotope labeled version of the protease sensitive peptide. This permits the use of compounds that are substantially chemically identical, but isotopically distinguishable. A method for the production of molecules comprising deuterium atoms is given in U.S. Patent Application No. 2002/0119490 A1 and references therein, all of which are incorporated herein by reference. For example, one or more hydrogens in the peptide can be substituted with deuterium to generate isotopically heavy reagents. Isotopically labeled amino acids are commercially available (Cambridge Isotope Laboratories, Andover, Mass.) and can simply be used in peptide synthesis.

While a variety of peptide designs are possible, the present invention contemplates an embodiment wherein the protease-sensitive peptide comprises an N-terminal epitope (for convenient capture and purification from the mixture), a region of positively charged amino acids such as arginine, lysine or histidine (to improve flight in the mass spec), and a C-terminal region comprising hydrophobic amino acids (e.g. phenylalanine) for protease digestion. Optionally, the N-terminus can have other amino acids (e.g. methionine) or protecting groups (FMOC, etc.). It is not intended that the present invention be limited by the particular epitope; known epitopes (or variants thereof) can be employed (whether containing positively charged amino acids or not). The region of positively charged amino acids can be a) a single amino acid (e.g. one arginine), or b) a plurality of amino acids. Where it is a plurality, it may be comprised of a mixture of different amino acids or (preferably) can be a string (e.g. between 2 and 20 amino acids, preferably between 2 and 9 amino acids, and more preferably between 5 and 7 amino acids) of a single amino acid (e.g. arginine). Examples of protease-sensitive peptides where arginine is used (between one and nine amino acids) in the region of positively charged amino acids—along with a variety of epitopes—are shown in Table 2 (SEQ ID NOS: 1-109). The present invention contemplates these peptides as compositions of matter and as useful in various assays described herein (including but not limited to a mass spec-based protease detection assay which can be used, among other things, to quality control commercially available translation systems).

While the protease-sensitive peptide can be made synthetically, it can also be made during the translation process. Therefore, in one embodiment, the present invention contemplates nucleic acid coding for the protease-sensitive peptide as well as a method wherein said nucleic acid is used as a template for translation. Nucleic acid sequences (SEQ ID NOS: 110-119) for a number of epitopes (SEQ ID NOS: 120-129) are provided in Table 3. An experimental example is described herein wherein the protease-sensitive peptide is made during in vitro translation.

For high throughput, most of the steps can be readily automated. While a batch approach can be readily utilized, the present invention also contemplates both continuous flow systems or dialysis systems.

In a preferred embodiment, a transcription/translation system used wherein nucleic acid (typically DNA, but RNA if desired) coding for the protein which may contain a possible mutation is added to the translation system. The system is incubated to synthesize the nascent proteins. The nascent protein is then separated from the translation system using an affinity marker. In one embodiment the affinity marker is located at or close to (e.g. within ten amino acids of) the N-terminal end of the protein, while in another embodiment, the affinity marker can be distributed throughout the sequence of the protein (whether randomly or at defined intervals).

It is not intended that the present invention be limited by the nature of the N- and C-terminal epitopes, or the type of affinity marker utilized. A variety of markers are contemplated. Table 3 provides a number of commercially available epitopes (and additional epitopes are described in the examples). In one embodiment, the affinity marker comprises an epitope recognized by an antibody or other binding molecule. In another embodiment, the affinity marker is biotin and is distributed randomly on lysine residues. In one embodiment, the N-terminal marker comprises a fluorescent marker (e.g. a BODIPY marker), while the C-terminal marker comprises a metal binding region (e.g. His tag).

The present invention contemplates a variety of methods wherein two or three markers (e.g. the N- and C-terminal markers and the affinity markers) are introduced into a nascent protein. In both the two marker and three marker embodiments, the present invention contemplates that one or more of the markers (and in the preferred embodiment, all of the markers/epitopes) will be introduced into the nucleic acid template by primer extension or PCR (and thus, introduction via charged tRNAs is unnecessary). In one embodiment, the present invention contemplates a primer comprising (on or near the 5'-end) a promoter, a ribosome binding site ("RBS"), and a start codon (e.g. ATG), sequence encoding an epitope, along with a region of complementarity to the template (e.g. sufficiently complementary to hybridize to a portion of a disease-related gene or, in preferred embodiments, completely complementary to a portion of a disease-related gene). In another embodiment, the present invention contemplates a primer comprising (on or near the 5'-end) a promoter, a ribosome binding site ("RBS"), a start codon (e.g. ATG), a region encoding a second epitope, and a region of complementarity to the template. It is not intended that the present invention be limited by the length of the region of complementarity; preferably, the region is greater than 8 bases in length, more preferably greater than 15 bases in length, and still more preferably greater than 20 bases in length (but commonly less than 40 bases in length, and more typically less than 30 bases in length).

It is also not intended that the present invention be limited by the ribosome binding site. In one embodiment, the present invention contemplates primers comprising the Kozak sequence, a string of non-random nucleotides (consensus sequence 5'-GCCA/GCCATGG-3') (SEQ ID NO: 130) which are present before the translation initiating first ATG in majority of the mRNAs which are transcribed and translated in eukaryotic cells. See M. Kozak, Cell 44:283-292 (1986). In another embodiment, the present invention contemplates a primer comprising the prokaryotic mRNA ribosome binding site, which usually contains part or all of a polypurine domain UAAGGAGGU (SEQ ID NO:131) known as the Shine-Dalgarno (SD) sequence found just 5' to the translation initiation codon: mRNA 5'-UAAGGAGGU-$N_{5-10}$-AUG. (SEQ ID NO:132)

For PCR, two primers are used. In one embodiment, the present invention contemplates as the forward primer a primer comprising (on or near the 5'-end) a promoter, a ribosome binding site ("RBS"), a start codon (e.g. ATG), a region encoding an affinity marker, and a region of complementarity to the template. The present invention contemplates that the reverse primer, in one embodiment, comprises (at or near the 5'-end) one or more stop codons and a region encoding a C-terminus marker (such as a HIS-tag) and (optionally) a region which will generate a stop codon if there is a frameshift. This latter region can be designed in a number of ways. However, to efficiently generate stop codons for every type of frameshift, the following sequence is useful: ATA-AAT-AAA (SEQ ID NO: 133). Where there are no frameshifts, this sequence codes for Ile-Asn-Lys (SEQ ID NO: 134). Where there are frameshifts, the sequence will generate a stop codon. Since the sequence is preferred as part of the reverse primer, the sequence is used in the following orientation: 5'-TTT-ATT-TAT-3' (SEQ ID NO:135).

The present invention also contemplates embodiments where the affinity marker is introduced through a misaminoacylated tRNA. In one embodiment the misaminoacylated tRNA only recognizes a codon which codes for a particular amino acid such as a codon for lysine. In this case, the affinity marker is incorporated randomly throughout the protein sequence. In another embodiment, more than one misaminoacylated tRNA is utilized. In this case, the affinity marker may be randomly distributed throughout the protein sequence at more than a single amino acid such as lysine or tyrosine. In another embodiment the misaminoacylated tRNA is a suppressor tRNA and incorporates the affinity marker at a specific position in the protein sequence.

Another aspect of the present invention contemplates an oligonucleotide, comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for an epitope marker (or variant thereof that can be recognized by an antibody), and iii) said 3' portion comprises a sequence complementary to a portion of the APC gene (or another gene whose truncated products are associated with disease, i.e. a "disease related gene"). In one embodiment, said oligonucleotide is less than two hundred bases in length. In a preferred embodiment, said oligonucleotide is less than one hundred bases in length, and most preferably less than 70 bases in length (e.g. between 40 and 60 bases in length). In one embodiment, said 5' portion is between ten and forty bases in length (preferably between eight and sixty bases in length, and more preferably between fifteen and thirty bases in length). In one embodiment, said middle portion is between ten and one hundred bases in length (preferably between eight and sixty bases in length, and more preferably between fifteen and thirty bases in length). In one embodiment, said 3' portion is between ten and forty bases in length (and more preferably between fifteen and thirty bases in length). In one embodiment, said sequence complementary to the portion of the APC gene is greater than 15 bases in length. In another embodiment, said sequence complementary to the portion of the APC gene is greater than 20 bases in length.

Another aspect of the present invention contemplates a kit, comprising: a) a first oligonucleotide comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for a first epitope marker, and iii) said 3' portion comprises a sequence complementary to a first portion of the APC gene (or other disease related gene); b) a second oligonucleotide comprising a 5' portion, a middle portion contiguous with said 5' portion, and a 3' portion contiguous with said middle portion, wherein i) said 5' portion comprises at least one stop codon, ii) said middle portion comprises a sequence encoding for a second epitope marker, and iii) said 3' portion comprises a sequence complementary to a second portion of the APC gene (or other disease related gene). Optionally, the kit comprises a protease-sensitive peptide (discussed above) to be used as a control for mass spec. In one embodiment, said kit further comprises a polymerase. In another embodiment, said kit further comprises a misaminoacylated tRNA. In another embodiment, said kit further comprises antibodies directed against said epitopes.

Another aspect of the present invention contemplates a method of introducing coding sequence for one or more epitope markers into nucleic acid, comprising: a) providing: a first oligonucleotide primer comprising a 5' portion, a middle portion contiguous with said 5' portion, and a 3' portion contiguous with said middle portion, wherein 1) said 5' portion comprises a sequence corresponding to a promoter, 2) said middle portion comprises a sequence corresponding to a ribosome binding site, a start codon, and a sequence coding for a first epitope marker, and 3) said 3' portion comprises a sequence complementary to a first portion of the APC gene (or other disease related gene); ii) a second oligonucleotide primer comprising a 5' portion, a middle portion contiguous with said 5' portion, and a 3' portion contiguous with said middle portion, wherein 1) said 5' portion comprises at least one stop codon, 2) said middle portion comprises a sequence encoding for a second epitope marker, and 3) said 3' portion comprises a sequence complementary to a second portion of the APC gene (or other disease related gene); iii) a polymerase; and iv) template nucleic acid comprising a region of the APC gene (or other disease related gene), said region comprising at least said first portion of the APC gene; and b) mixing said template nucleic acid with said first primer, second primer and said polymerase under conditions such that amplified template is produced, said amplified template comprising said sequence coding for an epitope marker. In one embodiment, said first and said second oligonucleotide are each less than one hundred bases in length. In one embodiment, said sequence complementary to a portion of the APC gene of said first and said second oligonucleotide is 10 bases or greater, but preferably greater than 15 bases in length. In another embodiment, said sequence complementary to a portion of the APC gene of said first and said second oligonucleotide is greater than 20 bases in length.

While not intending to limit the present invention, it is understood by one skilled in the art, that "a region of the APC gene" is larger than "a portion of the APC gene" (just as "regions" of any other gene associated with disease are larger than "portions" of the same). For example, a region of the APC gene may comprise, but is not limited to, the region coding for amino acids 1098-1696 (i.e., segment 3). Other segments (such as segment 23) are also contemplated.

In one embodiment, the present invention contemplates 12 primer sets designed to amplify specific sequences (called segments) of the cell-line APC gene (S1-S12; FIG. 44) using DNA (e.g. isolated from fecal material, urine, polyps, tumors, biopsies, cell lines, etc.) or RNA (e.g. mRNA). It is not intended that the present invention be limited to the precise primers or primer sets. However, Table 4 provides 12 illustrative, 5'-primers and Table 5 provides 12 illustrative, 3'-primers. Together, these primers permit coverage of the MCR region. In one embodiment, the 3'-primers have stop codons (see e.g. Table 6); in another embodiment, the 3'-primers lack stop codons (see e.g. Table 7).

While these 12 sets may be optimal for cell-lines, the integrity of fecal DNA can affect the ability to perform PCR-amplification over regions this large. Therefore, in another embodiment, the same MCR region could be covered with 20-30 or fewer primers sets, more preferably 12-20 primer sets.

Another aspect of the present invention contemplates a method, comprising: a) providing: i) the amplified template (described above); i) a translation system; b) introducing said amplified template into said translation system so as to create nascent protein (or portion thereof) comprising an N-terminal epitope; c) isolating said nascent protein; and d) detecting said protein (or portion thereof) by mass spectrometry.

In one embodiment, the isolating of the nascent protein comprises immobilizing said nascent protein by contacting said nascent protein with a ligand (e.g. antibody) which binds the N-terminal epitope. Typically, said ligand is attached to a solid support. Where the N-terminal epitope is biotin (for example), said ligand is selected from the group consisting of avidin and strepavidin, and variants, mutants and derivatives thereof.

In one embodiment, the present invention contemplates detecting simultaneously the mass of multiple polypeptides (i.e. two or more) by mass spec. In the context of the present invention, this can be an important advantage, since multiplex detection of several WT segments and simultaneous scanning for possible mutations can lower time and cost of ultimate CRC assay. In one embodiment, the present invention contemplates the simultaneous detection of 2 different APC segments; importantly, these were translated in a single cell-free reaction.

Other embodiments and advantages of the invention are set forth, in part, in the description which follows and, in part, will be obvious from this description, or may be learned from the practice of the invention.

DEFINITIONS

To facilitate understanding of the invention, a number of terms are defined below.

"Proteins" are composed of "amino acids" arranged into linear polymers or polypeptides. In living systems, proteins comprise over twenty common amino acids. These twenty or so amino acids are generally termed the "native" amino acids. At the center of every amino acid is the alpha carbon atom which forms four bonds or attachments with other molecules (FIG. 1). One bond is a covalent linkage to an amino group ($NH_2$) and another to a carboxyl group (COOH) which both participate in polypeptide formation. A third bond is nearly always linked to a hydrogen atom and the fourth to a side chain which imparts variability to the amino acid structure. For example, alanine is formed when the side chain is a methyl group ($-CH_3$) and a valine is formed when the side chain is an isopropyl group ($-CH(CH_3)_2$). It is also possible to chemically synthesize amino acids containing different side-chains, however, the cellular protein synthesis system, with rare exceptions, utilizes native amino acids. Other amino acids and structurally similar chemical compounds are termed non-native and are generally not found in most organisms.

A central feature of all living systems is the ability to produce proteins from amino acids. Basically, protein is formed by the linkage of multiple amino acids via peptide bonds such as the pentapeptide depicted in FIG. 1B. Key molecules involved in this process are messenger RNA (mRNA) molecules, transfer RNA (tRNA) molecules and ribosomes (rRNA-protein complexes). Protein translation normally occurs in living cells and in some cases can also be performed outside the cell in systems referred to as cell-free translation systems. In either system, the basic process of protein synthesis is identical. The extra-cellular or cell-free translation system comprises an extract prepared from the intracellular contents of cells. These preparations contain those molecules which support protein translation and depending on the method of preparation, post-translational events such as glycosylation and cleavages as well. Typical cells from which cell-free extracts or in vitro extracts are made are *Escherichia coli* cells, wheat germ cells, rabbit reticulocytes, insect cells and frog oocytes.

Both in vivo and in vitro syntheses involve the reading of a sequence of bases on a mRNA molecule. The mRNA contains instructions for translation in the form of triplet codons. The genetic code specifies which amino acid is encoded by each triplet codon. For each codon which specifies an amino acid, there normally exists a cognate tRNA molecule which functions to transfer the correct amino acid onto the nascent polypeptide chain. The amino acid tyrosine (Tyr) is coded by the sequence of bases UAU and UAC, while cysteine (Cys) is coded by UGU and UGC. Variability associated with the third base of the codon is common and is called wobble.

Translation begins with the binding of the ribosome to mRNA (FIG. 2). A number of protein factors associate with the ribosome during different phases of translation including initiation factors, elongation factors and termination factors. Formation of the initiation complex is the first step of translation. Initiation factors contribute to the initiation complex along with the mRNA and initiator tRNA (fmet and met) which recognizes the base sequence UAG. Elongation proceeds with charged tRNAs binding to ribosomes, translocation and release of the amino acid cargo into the peptide chain. Elongation factors assist with the binding of tRNAs and in elongation of the polypeptide chain with the help of enzymes like peptidyl transferase. Termination factors recognize a stop signal, such as the base sequence UGA, in the message terminating polypeptide synthesis and releasing the polypeptide chain and the mRNA from the ribosome.

The structure of tRNA is often shown as a cloverleaf representation (FIG. 3A). Structural elements of a typical tRNA include an acceptor stem, a D-loop, an anticodon loop, a variable loop and a T1C loop. Aminoacylation or charging of tRNA results in linking the carboxyl terminal of an amino acid to the 2'-(or 3'-) hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase. These tRNA synthetases have evolved to be extremely accurate in charging a tRNA with the correct amino acid to maintain the fidelity of the translation process. Except in special cases where the non-native amino acid is very similar structurally to the native amino acid, it is necessary to use means other than enzymatic aminoacylation to charge a tRNA.

The term "portion" refers to something is "less than the whole" and thus may refer to a relatively small part of a protein or an oligonucleotide. Specifically, a portion of a protein typically is in the range of between 5-200 contiguous amino acids (assuming that the protein has more than 200 amino acids) while a portion of a nucleic acid refers to a range of between 15-600 contiguous bases (again, assuming the gene has more than 600 continguous bases). Smaller portions (e.g. less than 5 amino acids) can be used but are not practical if one is attempted to detect mutations over a large area by examining a plurality of "test sequences". For example, to cover segment 3 of the APC gene, amplification of ten (usually contiguous) test sequences (whether overlapping or non-overlapping) of this region are performed. Since mass spec is used for analysis, the size of the test sequence is dictated in part by the reliable mass range of the equipment (factoring in the size of the N- and C-terminal epitopes). If overlapping test sequences are employed, the primers can be designed to hybridize inside the test sequence. If non-overlapping test sequences are employed, the primers are designed to hybridize outside (but adjacent) the test sequence.

The term "region" may refer to a relatively large segment of a protein or an oligonucleotide. Specifically, a region of a protein refers to a range of between 101-1700 contiguous amino acids, while a region of an oligonucleotides refers to a range of between 303-5100 contiguous nucleic acids.

The term "contiguous" when used in reference to a single molecule refers to a continuous, finite, sequence of units wherein each unit has physical contact with at least one other unit in the sequence. For example, a contiguous sequence of amino acids are physically connected by peptide bonds and a contiguous sequence of nucleic acids are physically connect by phosphodiester bonds. When used in the context of test sequences, contiguous refers to the coverage of the region without gaps.

The term "sequence corresponding to a promoter" refers to a non-coding nucleic acid region that is responsible for the regulation of transcription (an open reading frame) of the DNA coding for the protein of interest.

The term "sequence corresponding to a ribosome binding site" refers to a coding nucleic acid region that, when transcribed, allows the binding a mRNA in such a manner that translation occurs.

The term "gene" refers to a DNA sequence that comprises control and coding sequences necessary for the production of a polypeptide or precursor. The polypeptide can be encoded by a full length coding sequence or by any portion of the coding sequence. Typically, because of current limitations of mass spec equipment, an entire protein coded for by a disease gene will not be translated. Nonetheless, the portion may be referred to as a nascent protein or nascent polypeptide.

The term "wild-type" refers to a gene or gene product (or portion thereof) which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product (or portion thereof) which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. Importantly, the mass spec analysis of mutations does not require functional portions of the protein.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may have 5' and 3' ends.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically. Primers are used in primer extension reactions and PCR.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refers to the annealing of a complementary sequence to the target nucleic acid. The ability of two polymers of nucleic acid containing complementary sequences to find each other and anneal through base pairing interaction is a well-recognized phenomenon. Marmur and Lane, Proc. Natl. Acad. Sci. USA 46:453 (1960) and Doty et al., Proc. Natl. Acad. Sci. USA 46:461 (1960). The terms "annealed" and "hybridized" are used interchangeably throughout, and are intended to encompass any specific and reproducible interaction between an oligonucleotide and a target nucleic acid, including binding of regions having only partial complementarity.

The complement of a nucleic acid sequence as used herein refers to an oligonucleotide which, when aligned with the nucleic acid sequence such that the 5' end of one sequence is paired with the 3' end of the other, is in "antiparallel association." The term "complement" or "complementary" does not imply or limit pairing to the sense strand or the antisense strand of a gene; the term is intended to be broad enough to encompass either situation. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$." The $T_m$ of a particular nucleic acid duplex under specified conditions is the temperature at which on average half of the base pairs have disassociated. Where amplification is performed in a mixture of genomic DNA, it is convenient to carry out the hybridization of primers at a temperature that is at or above the Tm.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

As used herein, the term "poly-histidine tract" or (HIS-tag) refers to the presence of two to ten histidine residues at either the amino- or carboxy-terminus of a nascent protein A polyhistidine tract of six to ten residues is preferred. The polyhistidine tract is also defined functionally as being a number of consecutive histidine residues added to the protein of interest which allows the affinity purification of the resulting protein on a nickel-chelate column, or the identification of a protein terminus through the interaction with another molecule (e.g. an antibody reactive with the HIS-tag).

As used herein, the term "marker" is used broadly to encompass a variety of types of molecules (e.g. introduced into proteins using methods and compositions of the present invention) which are detectable through spectral properties (e.g. fluorescent markers or "fluorophores") or through functional properties (e.g. affinity markers). An epitope marker or "epitope tag" is a marker of the latter type, functioning as a binding site for antibody or other types of binding molecules (e.g. receptors, lectins and other ligands). Of course, if the epitope marker is used to immobilize the nascent protein, the epitope marker is also an affinity marker. An epitope has the property that it selectively interacts with molecules and/or materials containing acceptor groups. There are many epitope sequences reported in the literature including His×6 (HHH-HHH) (SEQ ID NO: 120) described by ClonTech and C-myc (EQKLISEEDL) (SEQ ID NO: 122) described by Roche-BM, Flag (DYKDDDDK) (SEQ ID NO: 121) described by Stratagene, SteptTag (WSHPQFEK) (SEQ ID NO:123) described by Sigma-Genosys and HA Tag (YPYDVPDYA) (SEQ ID NO:127) described by Roche-BM. Other epitopes are shown in Table 3 or are described in the examples.

One group of fluorophores with members possessing several favorable properties (including favorable interactions with components of the protein translational synthesis system) is the group derived from dipyrrometheneboron difluoride derivatives (BODIPY). Compared to a variety of other commonly used fluorophores with advantageous properties such as high quantum yields, some BODIPY compounds have the additional unusual property that they are highly compatible with the protein synthesis system. The core structure of all BODIPY fluorophores is 4,4-difluoro-4-bora-3a, 4a-diaza-s-indacene. See U.S. Pat. Nos. 4,774,339; 5,187, 288; 5,248,782; 5,274,113; 5,433,896; 5,451,663, all hereby incorporated by reference. A central feature is a difluoroboron as shown in FIG. 4. All BODIPY fluorophores have several desirable properties for a marker (Molecular Probes Catalog, pages 13-18) including a high extinction coefficient, high fluorescence quantum yield, spectra that are insensitive to solvent polarity and pH, narrow emission bandwidth resulting in a higher peak intensity compared to other dyes such as fluorescein, absence of ionic charge and enhanced photostability compared to fluorescein. The addition of substituents to the basic BODIPY structure which cause additional conjugation can be used to shift the wavelength of excitation or emission to convenient wavelengths compatible with the means of detection. An additional advantage of BODIPY-FL as a marker is the availability of monoclonal antibodies directed against it which can be used to affinity purify nascent proteins containing said marker. One example of such a monoclonal antibody is anti-BODIPY-FL antibody (Cat# A-5770, Molecular Probes, Eugene, Oreg.). This combined with the ability incorporate BODIPY-FL into nascent proteins with high efficiency relative to other commercially available markers using misaminoacylated tRNAs facilitates more efficient isolation of the nascent protein. These antibodies against BODIPY-FL can be used for quantitation of incorporation of the BODIPY into the nascent protein.

As used herein, the term "total tRNA" is used to describe a mixture comprising misaminoacylated marker tRNA molecules representing each amino acid. This mixture has a distinct advantage over the limited ability of misaminoacylated lys-tRNA to reliably incorporate in large variety of proteins. It is contemplated that "total tRNA" will provide a homogenous insertion of affinity markers in all nascent proteins.

DESCRIPTIONS OF THE DRAWINGS

FIG. 1 shows the structure of (A) an amino acid and (B) (SEQ ID NO: 164) a peptide.

FIG. 2 provides a description of the molecular steps that occur during protein synthesis in a cellular or cell-free system (SEQ ID NOS:165-167).

Figure 7A:
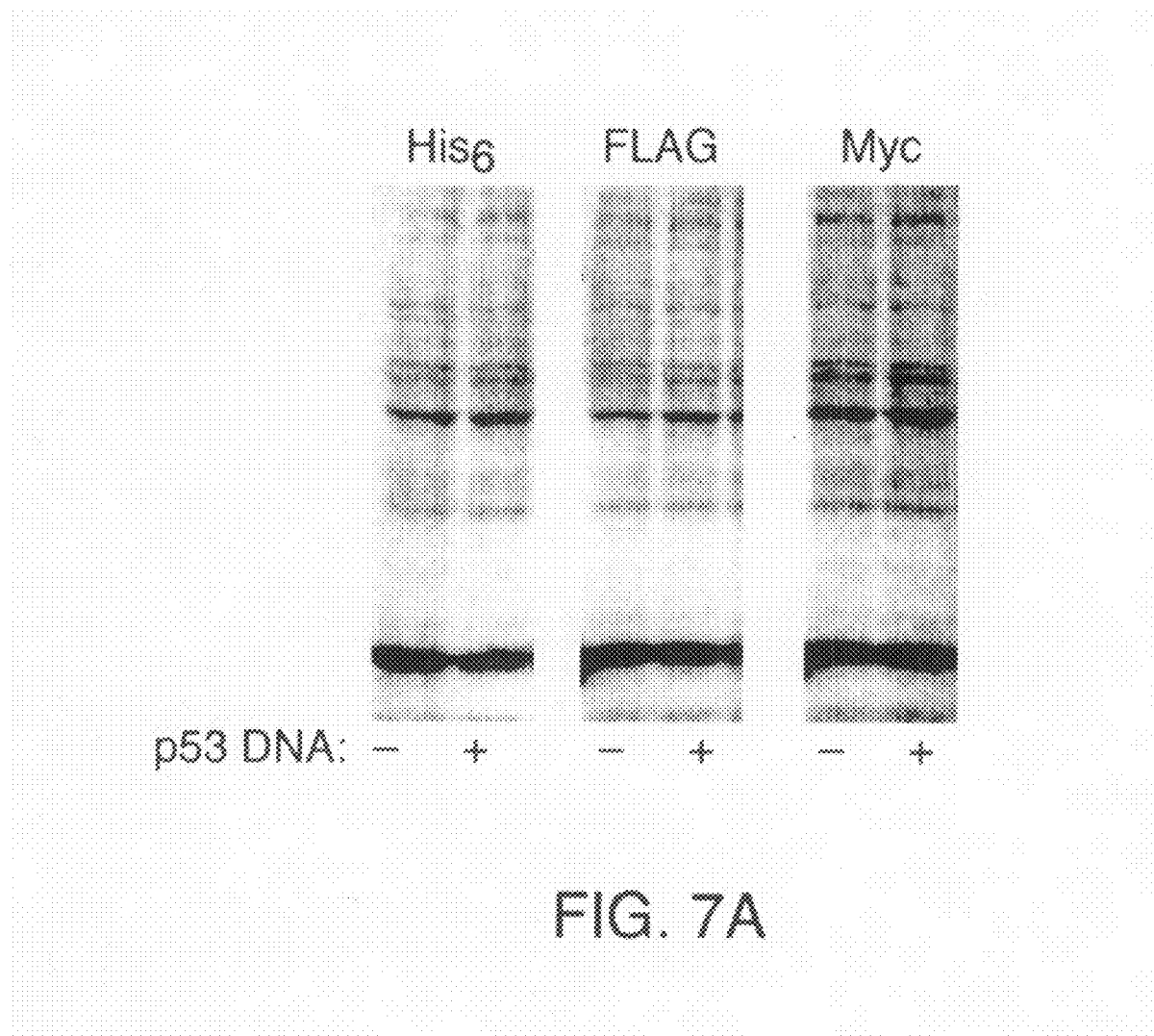
Figure 7B:
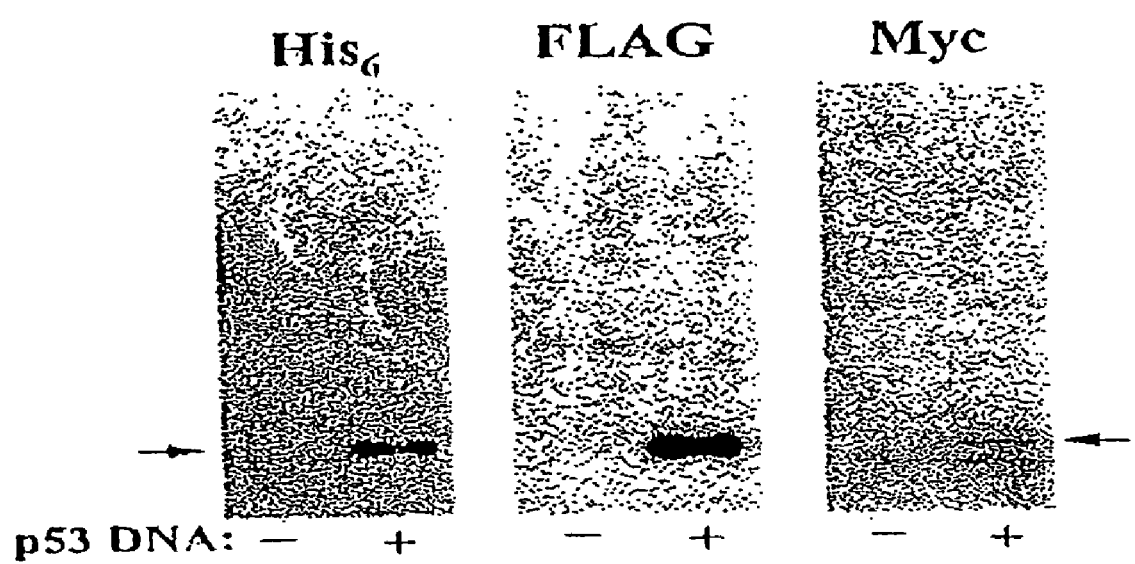

FIG. 7 shows Western blot analysis of in vitro translated triple-epitope-tagged wild-type p53 (RT-PCR derived DNA). FIG. 7A shows the total protein staining. FIG. 7B presents the Western blot analysis.

Figure 8A:
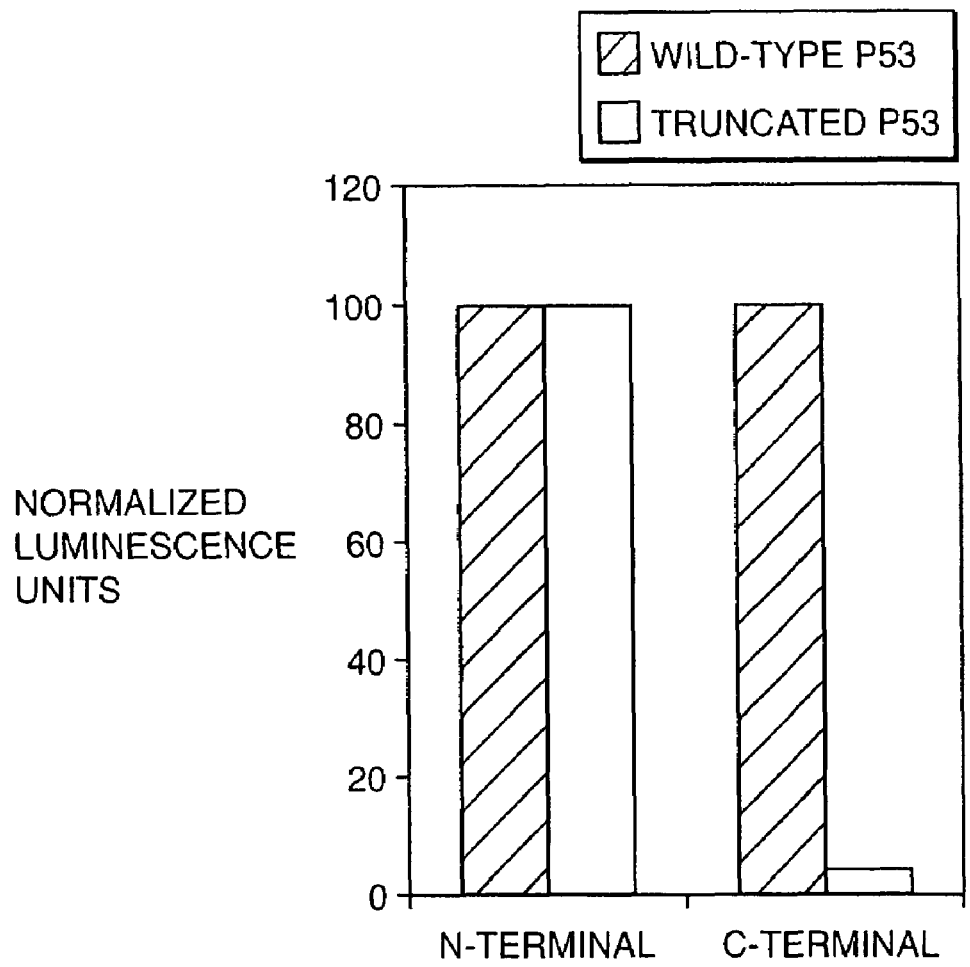
Figure 8B:
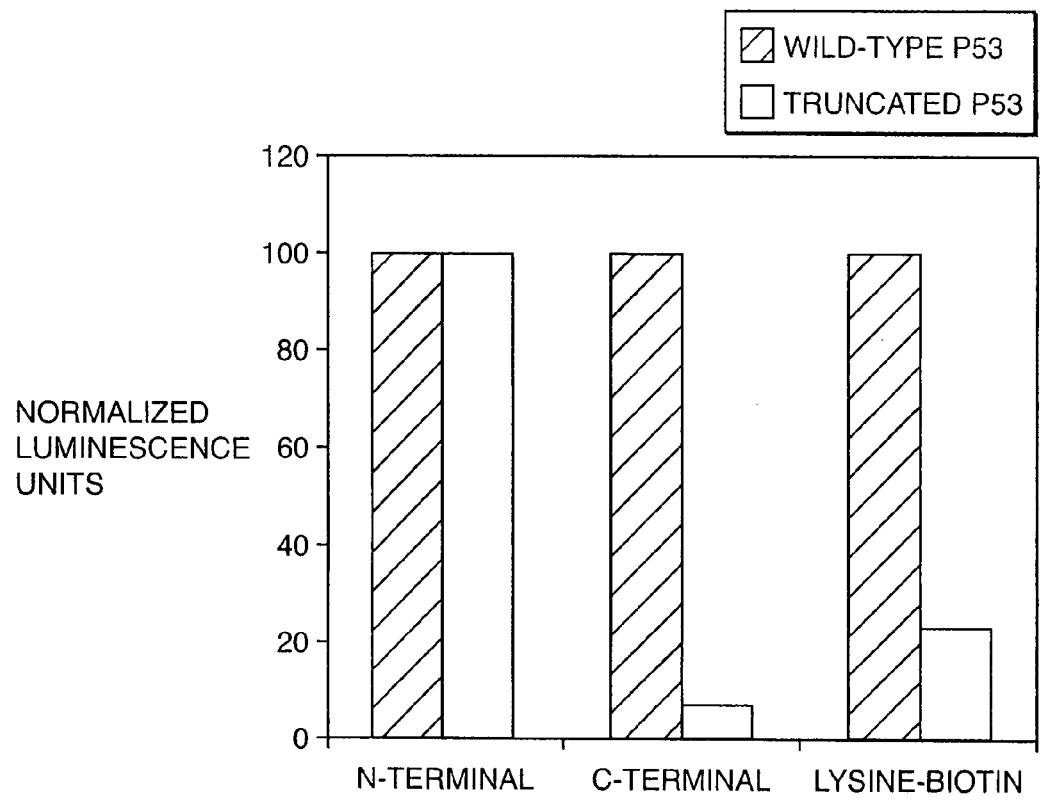
Figure 8C:
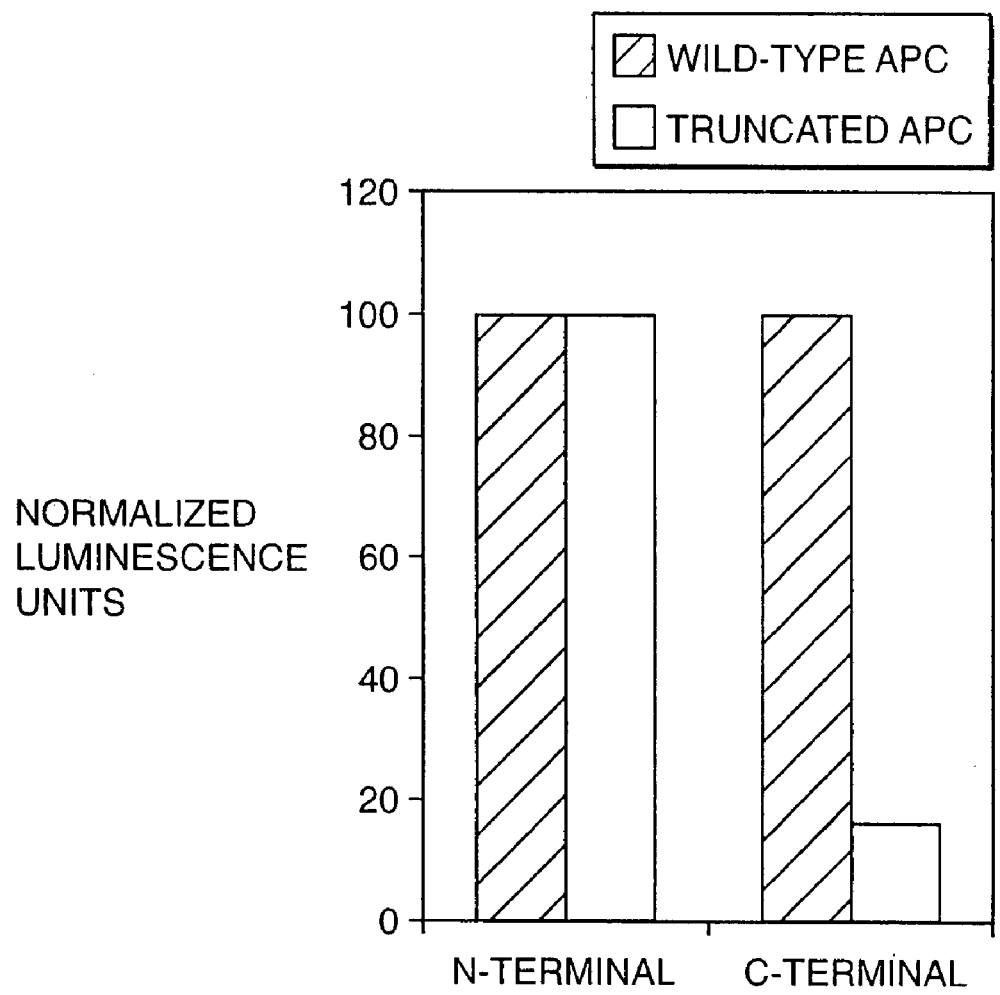

FIG. 8 shows three bar graphs representing the results of a gel-free chemiluminescent protein truncation assay of p53 and APC. FIG. 8A shows the results for p53 produced by in vitro translation, where the product is captured in a 96-well ELISA plate format using a mouse monoclonal antibody directed against the N-terminal FLAG epitope. FIG. 8B shows the results for p53 produced by in vitro translation, where the product is captured in a 96-well ELISA plate format using a nickel chelate plate. FIG. 8C shows the results for APC produced by in vitro translation, where the product is captured on nickel metal chelate 96-well ELISA plates. All WT N- and C-terminal signals as well as mutant N-terminal signals were normalized to 100%.

Figure 9:
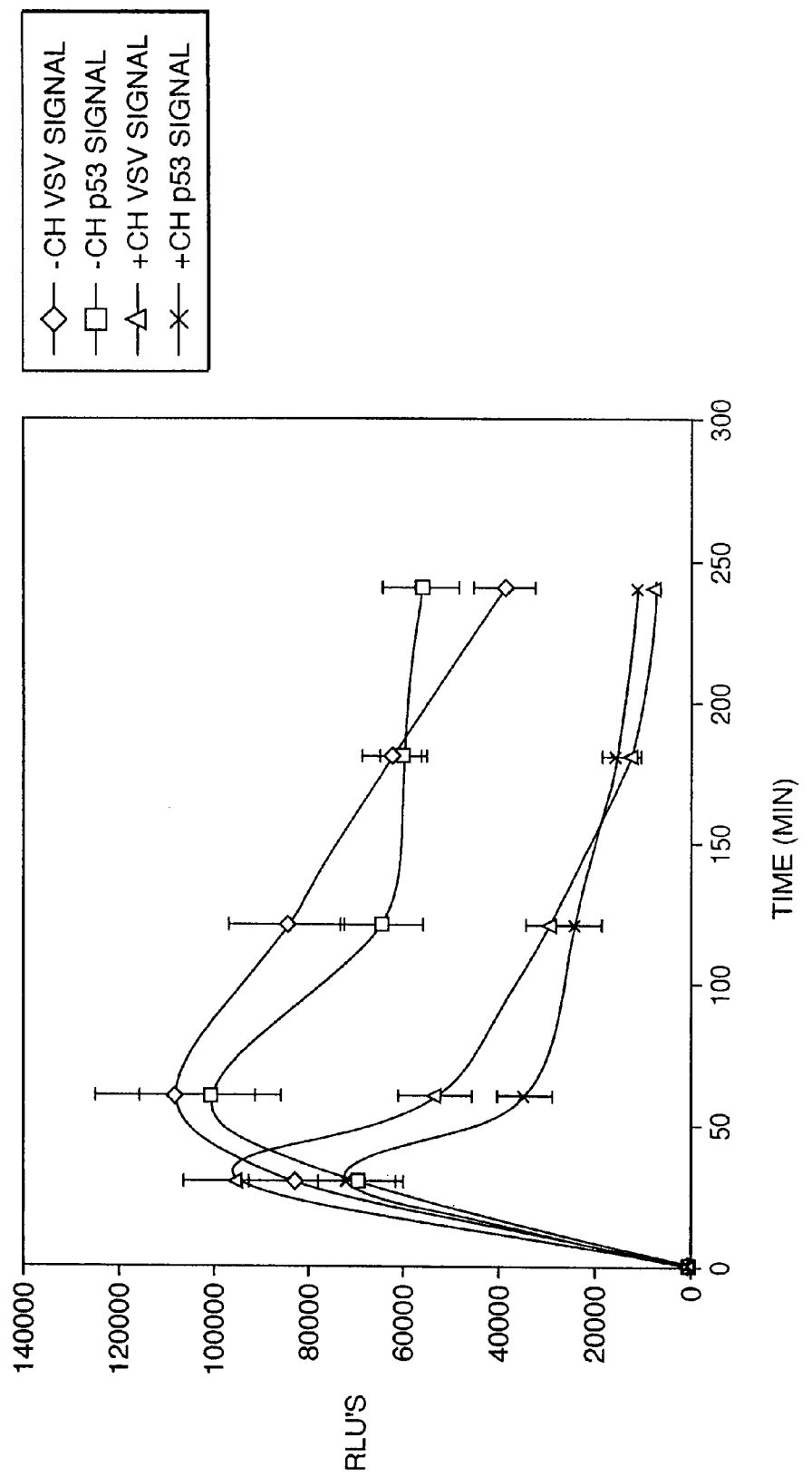

FIG. 9 shows the effect of addition of cycloheximide on the degradation of the N-terminal (VSV) and C-terminal (P53) signal of nascent protein.

Figure 10:
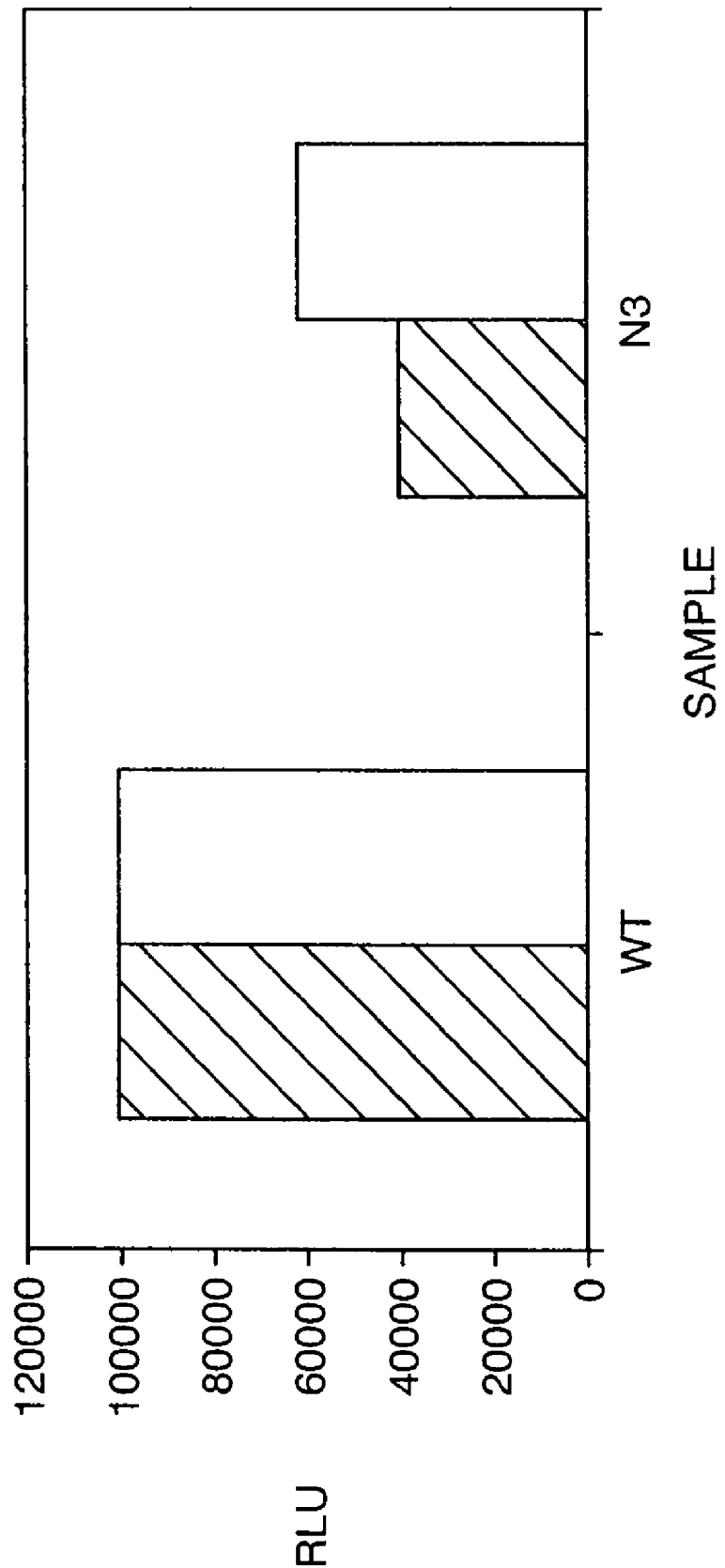

FIG. 10 displays data comparing the signals between standard incorporation of biotin-tRNA$^{lys}$ on an unmodified nascent protein (grey bars) and PCR insertion of five (5) extra terminal lysine residues on a nascent protein (black bars). WT: Wild-Type DNA. N3: Human Truncated Mutant DNA.

Figure 11:
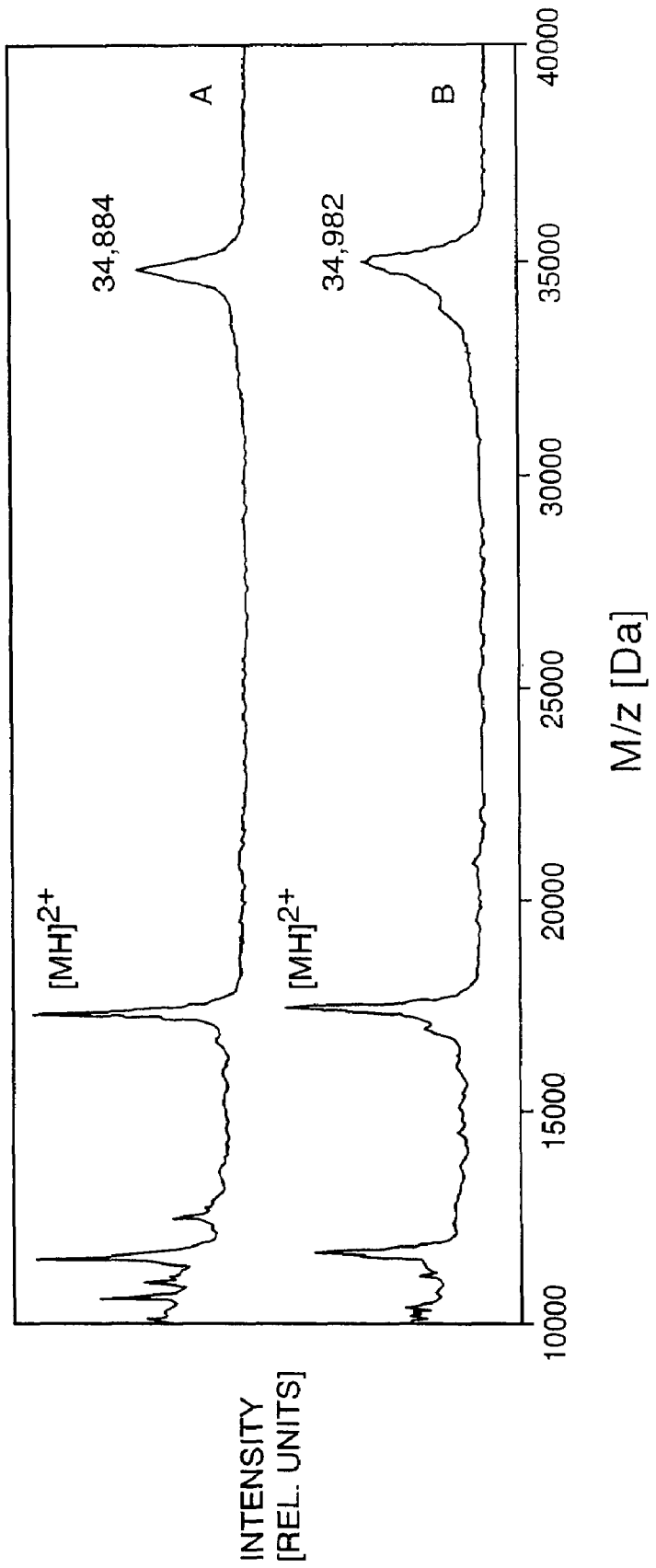

FIG. 11 displays the detection of a point mutation in in vitro expressed alpha-hemolysin by MALDI-TOF. Tracing a: 34,884-WT singly ionized species; $[MH]^{2+}$-WT doubly ionized species. Tracing b: 34,982-mutant singly ionized species; $[MH]^{2+}$-mutant doubly ionized species.

Figure 12:
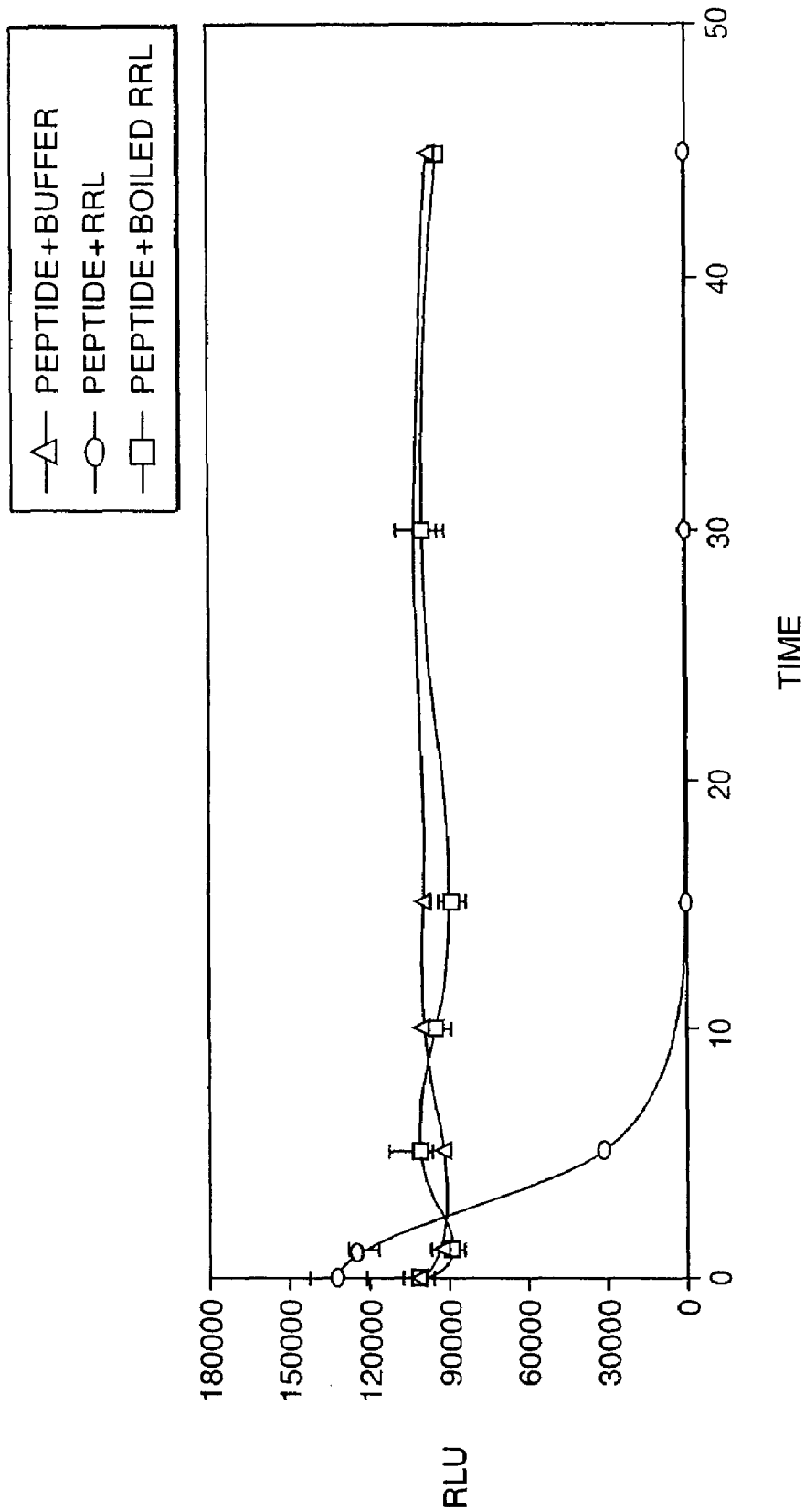

FIG. 12 shows a time course study wherein a VSV peptide is tested in buffer and RR extract.

Figure 13:
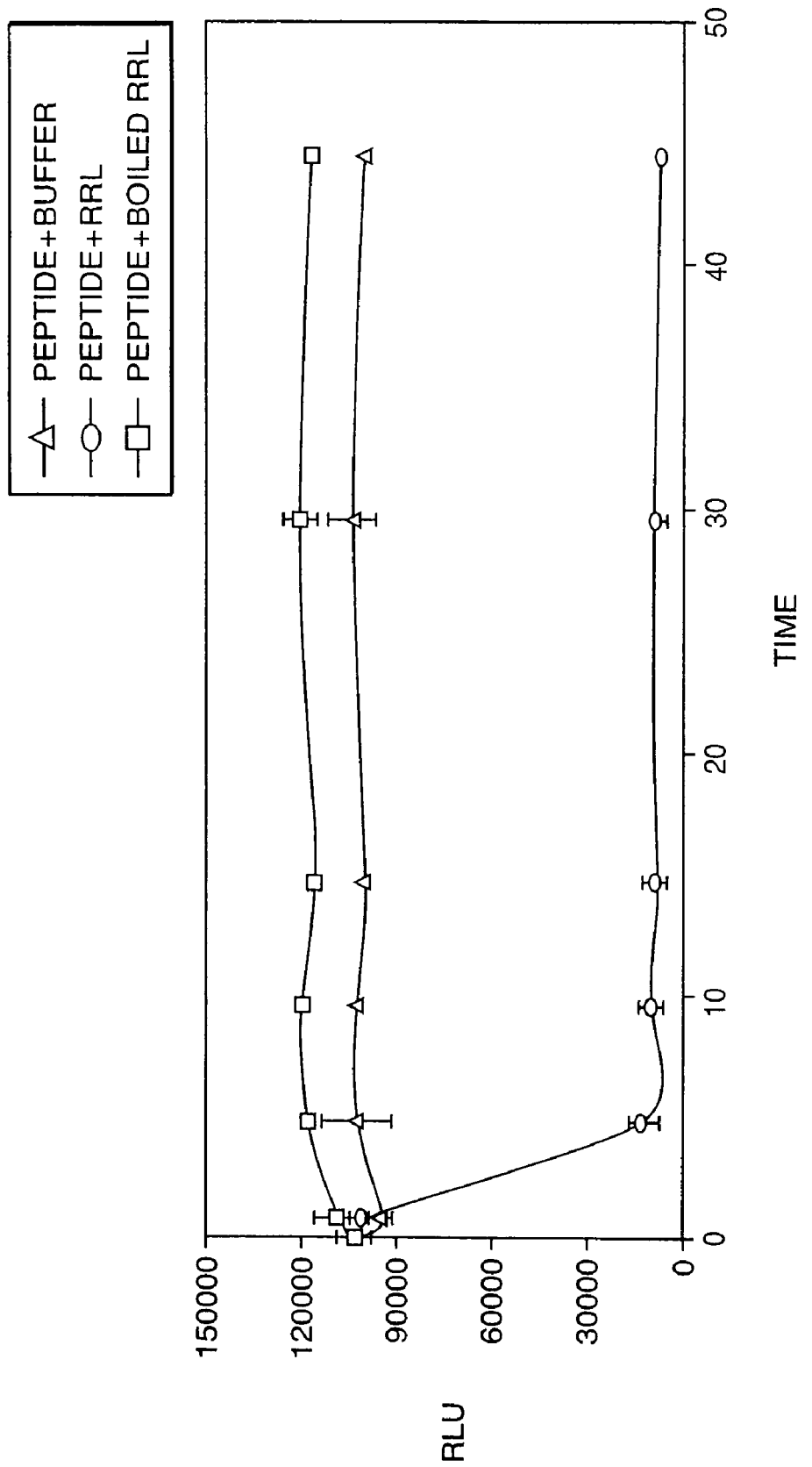

FIG. 13 shows a time course study wherein a P53 peptide is tested in buffer and RR extract.

Figure 14:
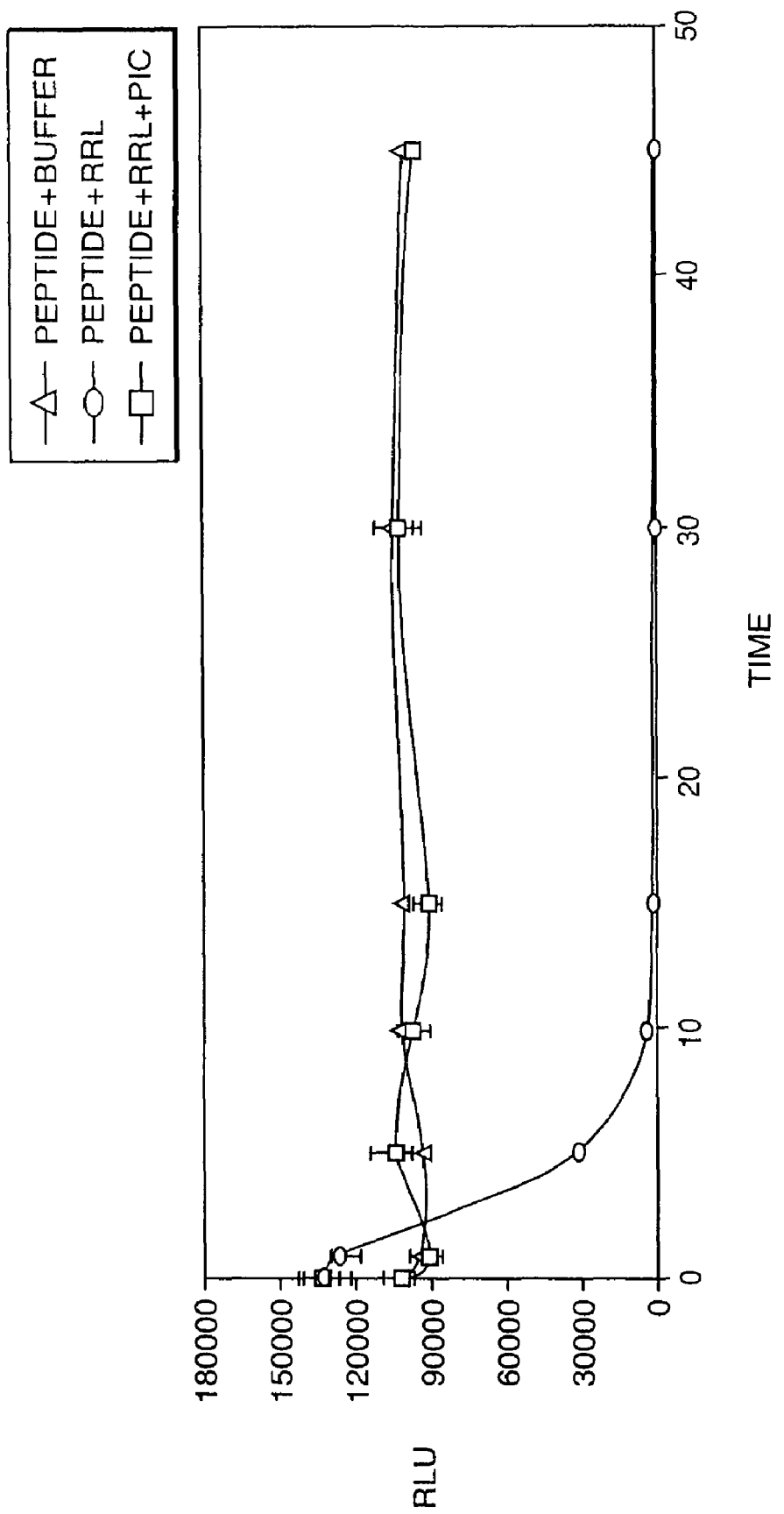

FIG. 14 shows a time course study wherein the proteolysis of a VSV peptide by RR extract is inhibited by a protease inhibitor cocktail.

Figure 15:
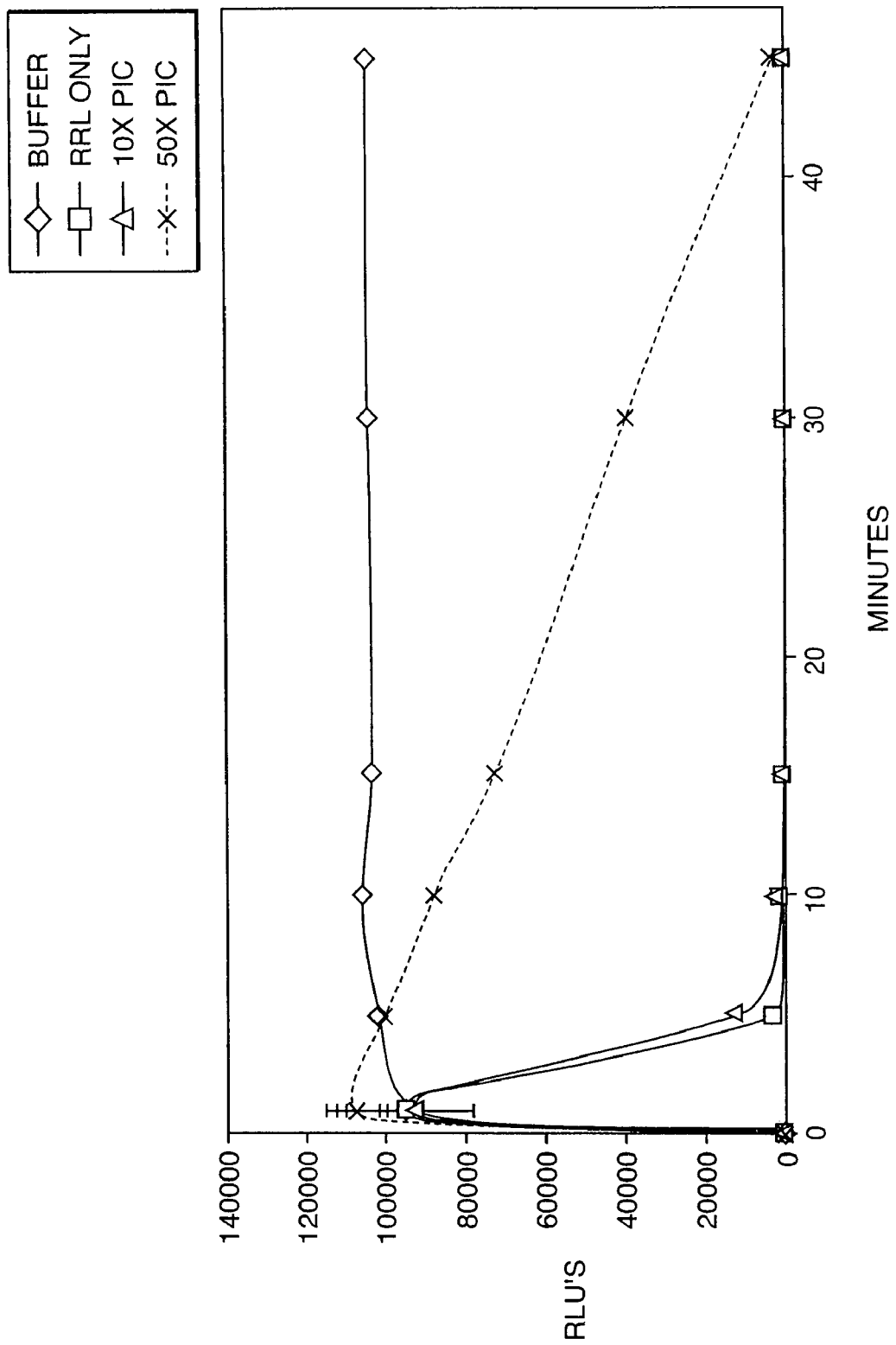

FIG. 15 shows a time course study wherein the proteolysis of a P53 peptide is only partially inhibited by a protease inhibitor cocktail.

Figure 16:
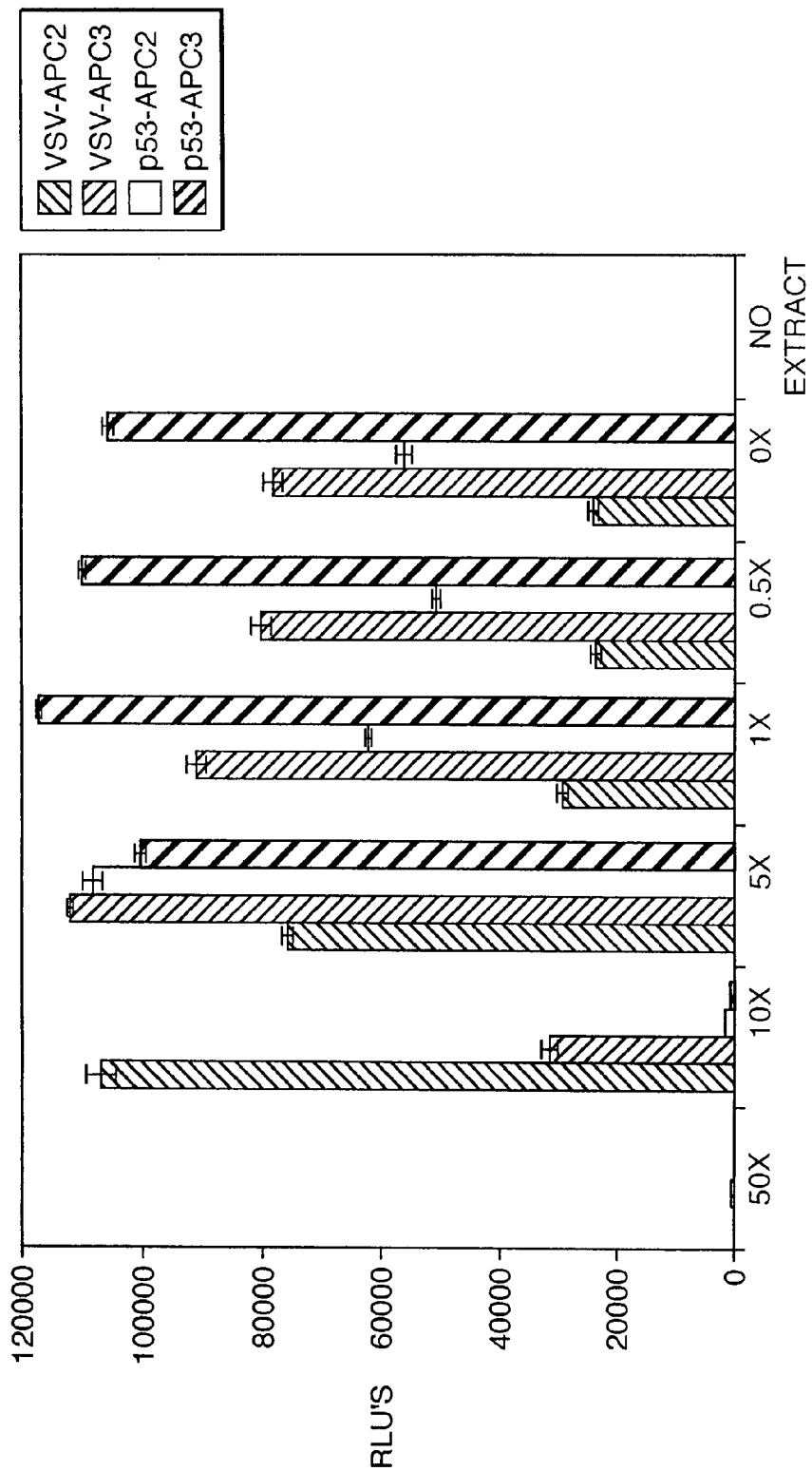

FIG. 16 is a bar graph showing the concentration dependence of the protease inhibitor cocktail on interference with protein production.

Figure 17:
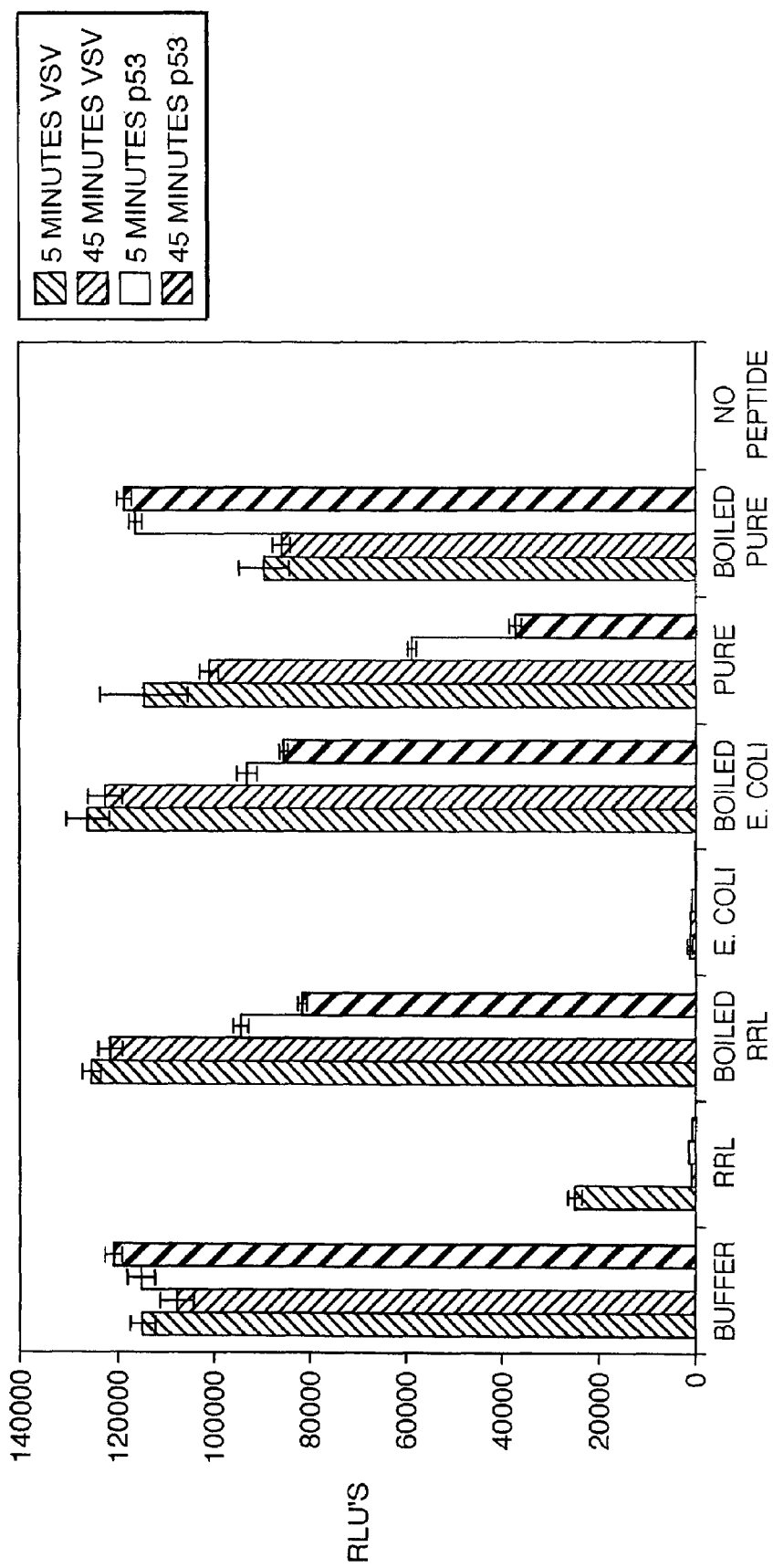

FIG. 17 is a bar graph showing that a reconstituted system nonetheless contains protease activity, albeit less than RR and E. coli extracts.

Figure 18:
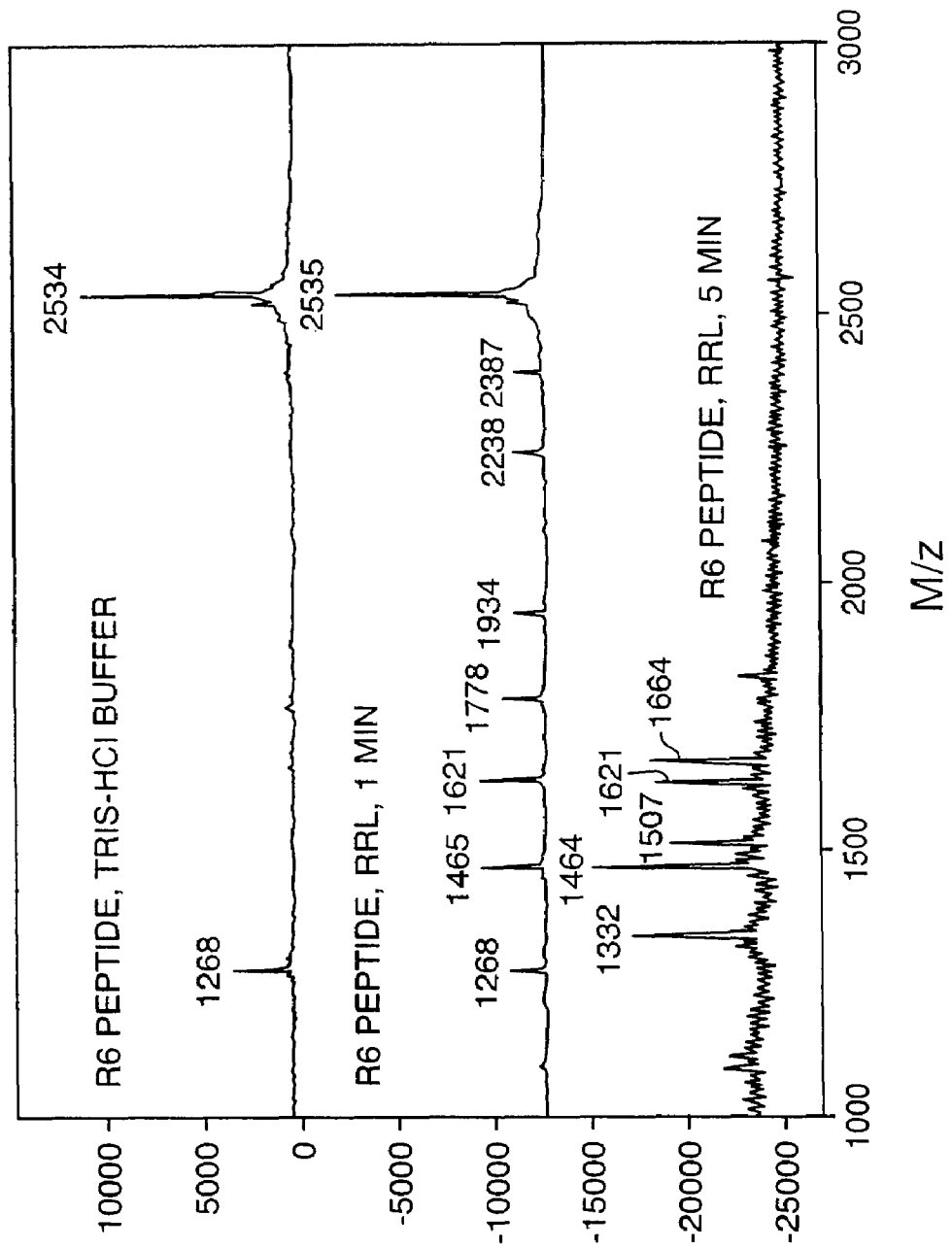

FIG. 18 is a three-panel readout of mass spec data wherein a protease-sensitive peptide is shown to be partially degraded at one minute (middle panel) and completely degraded (lower panel) at five minutes by a RR extract, as compared to the control (top).

Figure 19:
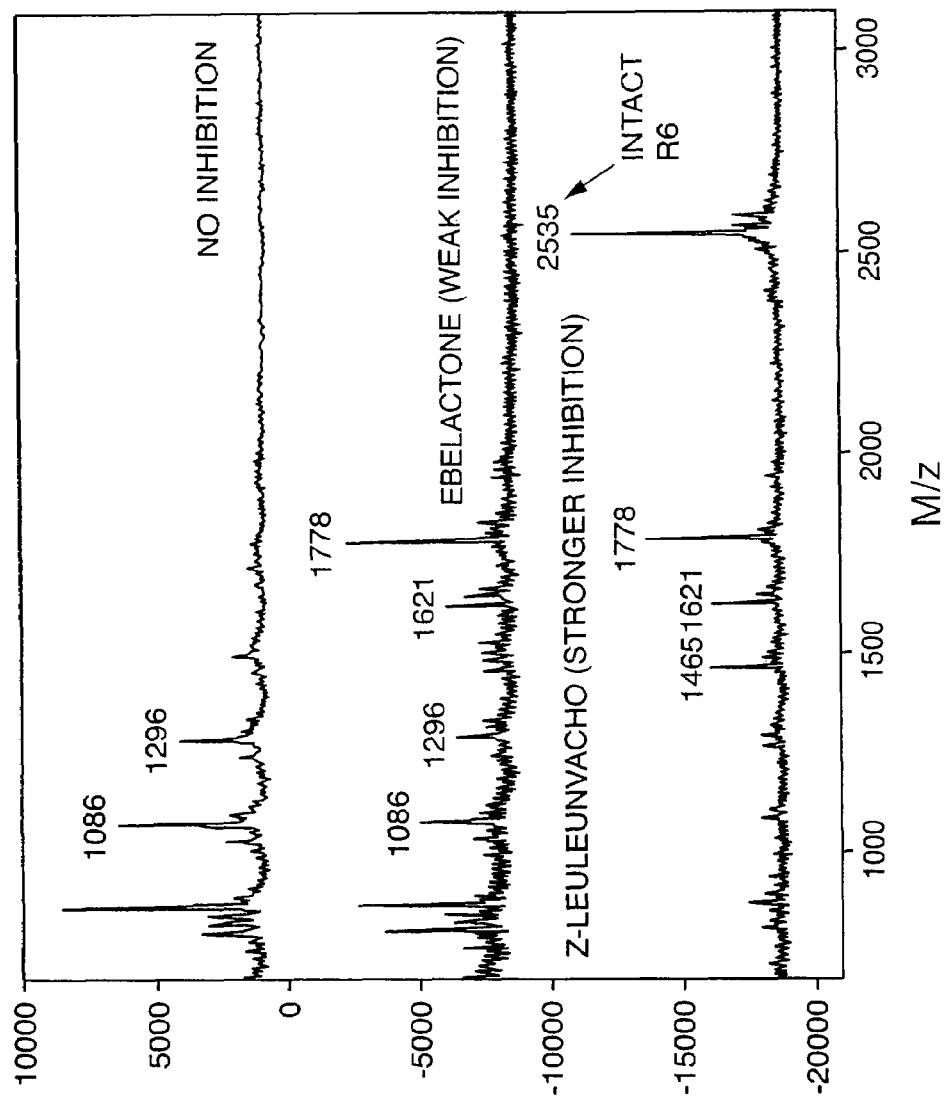

FIG. 19 is a three-panel readout of mass spec data wherein the degradation of a protease-sensitive peptide by RR extract is partially inhibited by one inhibitor (lower) and only weakly inhibited by another inhibitor (middle).

Figure 20:
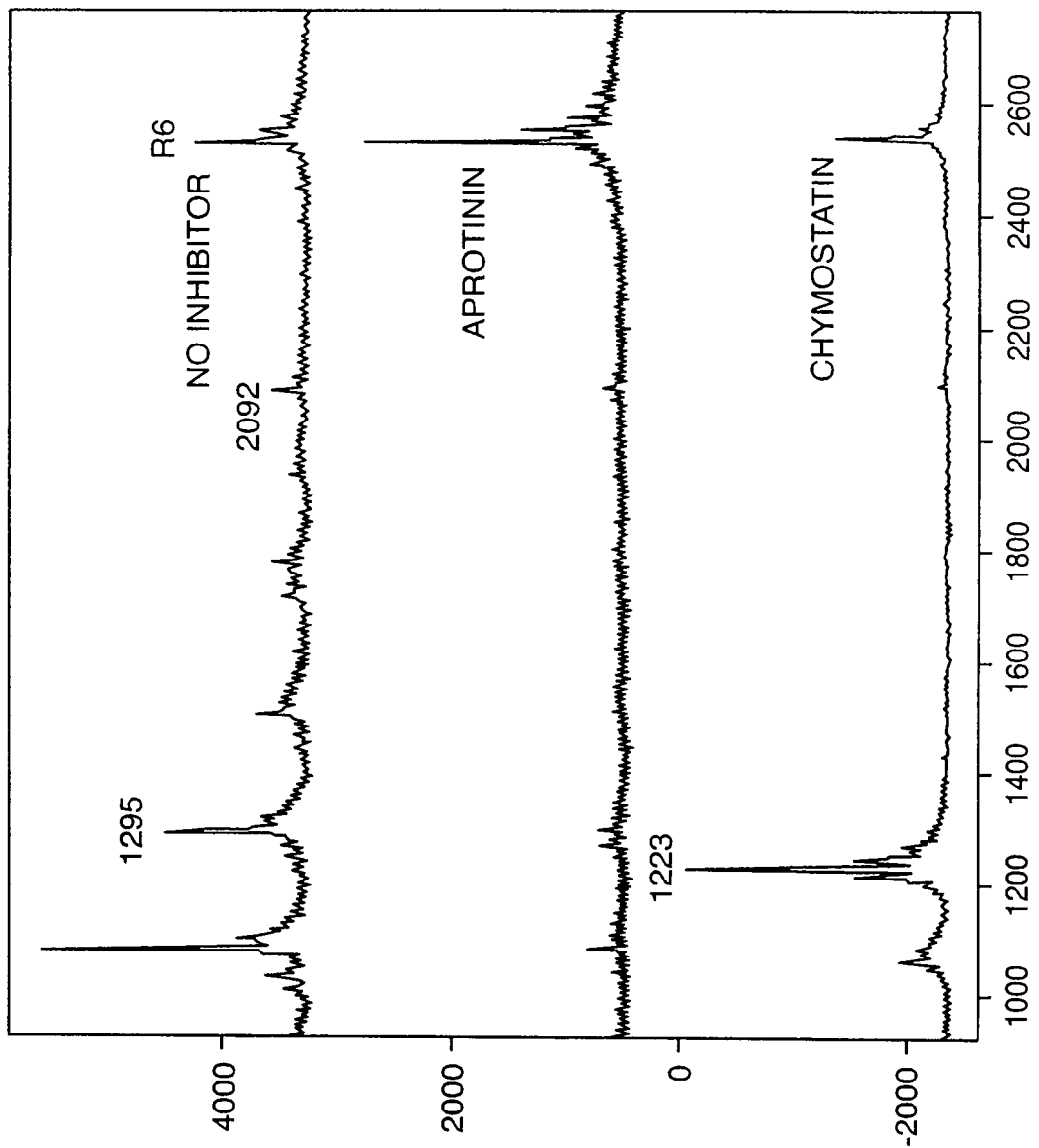

FIG. 20 is a three-panel readout of mass spec data wherein the degradation of a protease-sensitive peptide by E. coli extract is strongly inhibited by one inhibitor (middle) and only weakly inhibited by another inhibitor (lower).

Figure 21:
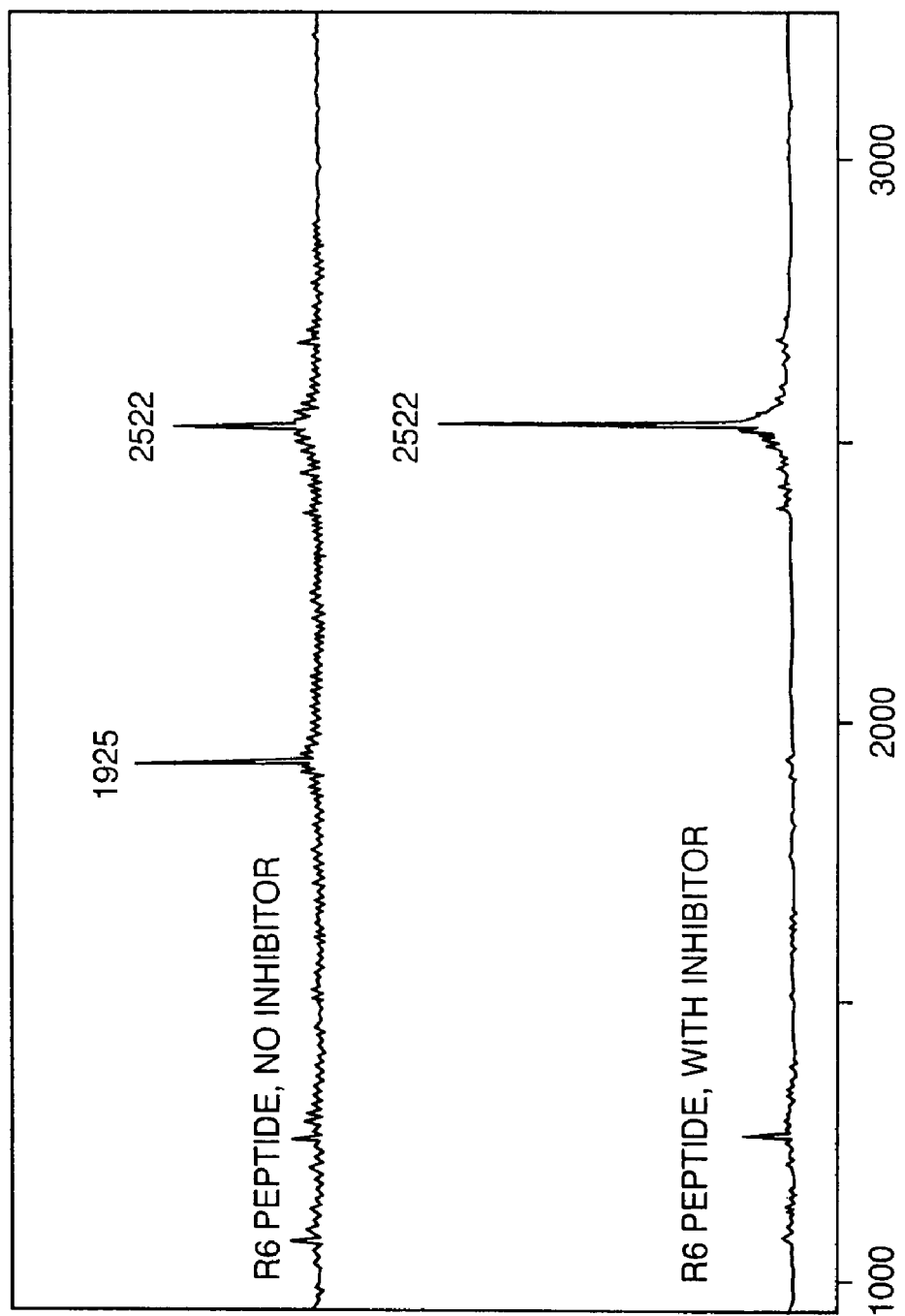

FIG. 21 is a two-panel readout of mass spec data showing the disappearance of the intact reference peptide (R6) after a 15 minute exposure to a reconstituted translation system (PURE I) in the absence of protease inhibitors (top). On other hand, the inhibitor AEBSF showed excellent inhibition of proteolysis under the same conditions (bottom).

Figure 22:
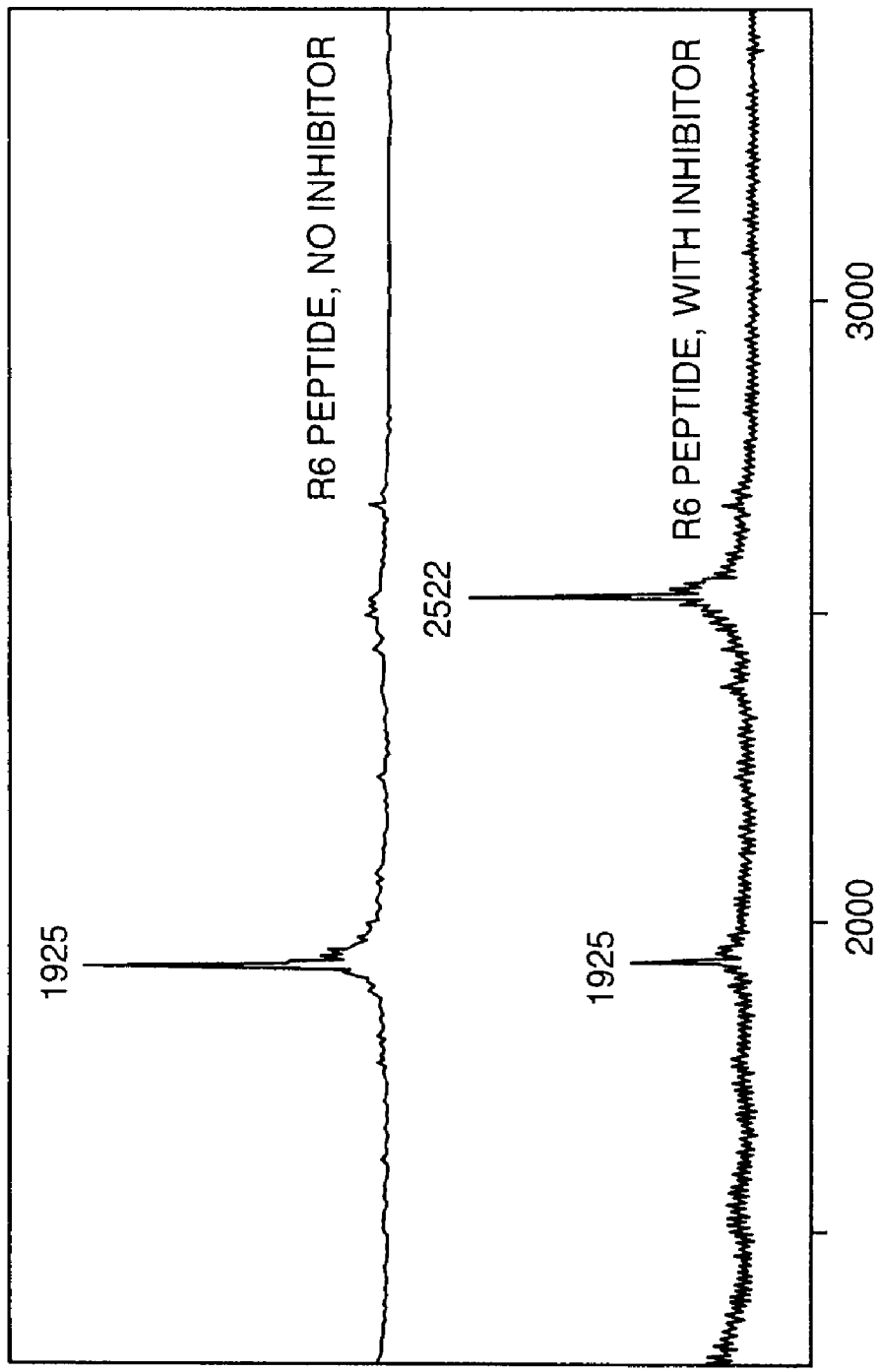

FIG. 22 is a two-panel readout of mass spec data showing virtually complete degradation of the reference peptide (R6) after exposure to the PURE II system with (bottom) and without (top) the AEBSF inhibitor.

Figure 23:
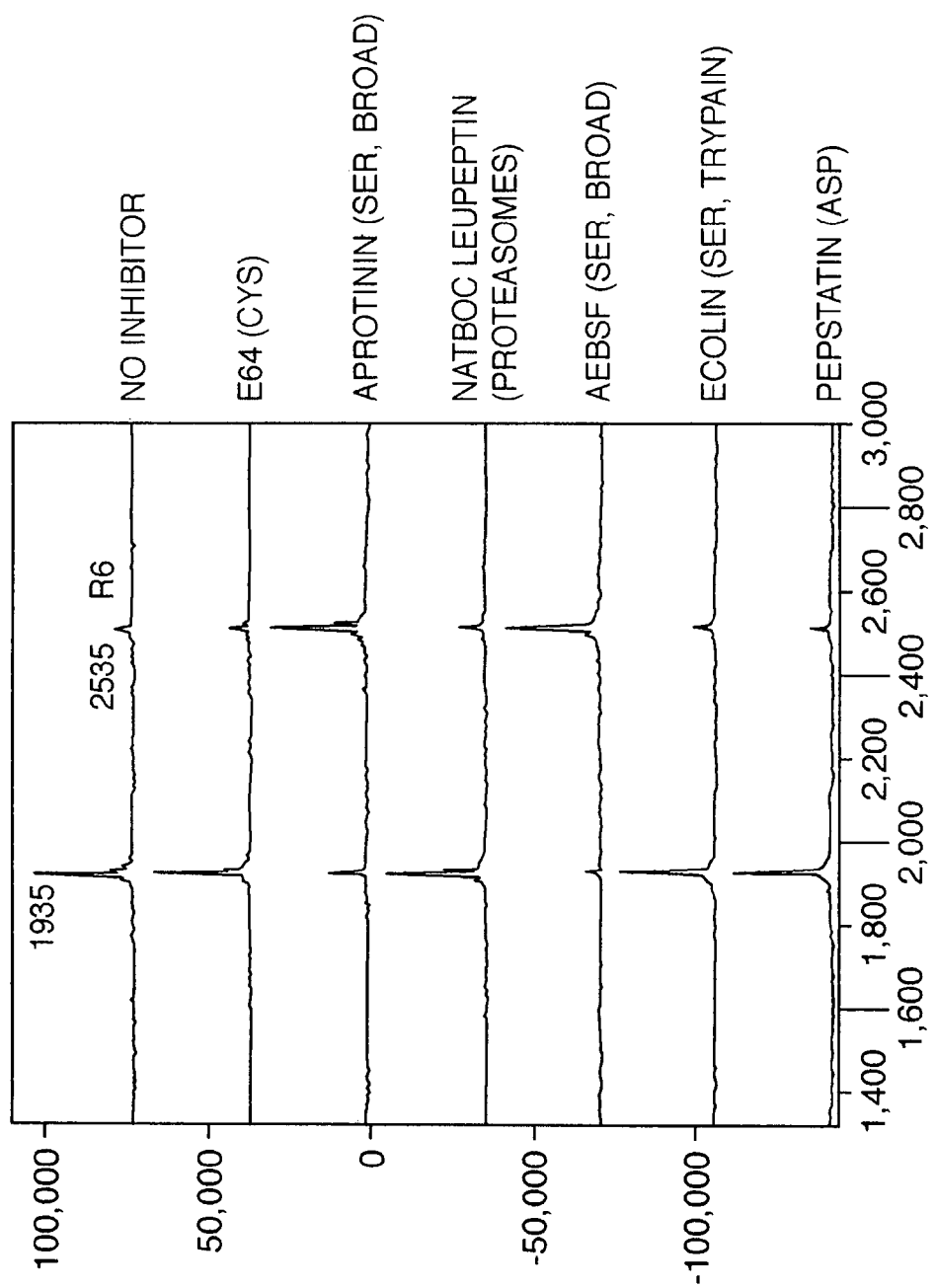

FIG. 23 is a seven-panel readout of mass spec data showing that the vast majority of compounds tested as possible inhibitors in the Pure II system were not effective, with the exception of AEBSF and aprotinin (third and fifth panels).

Figure 24:
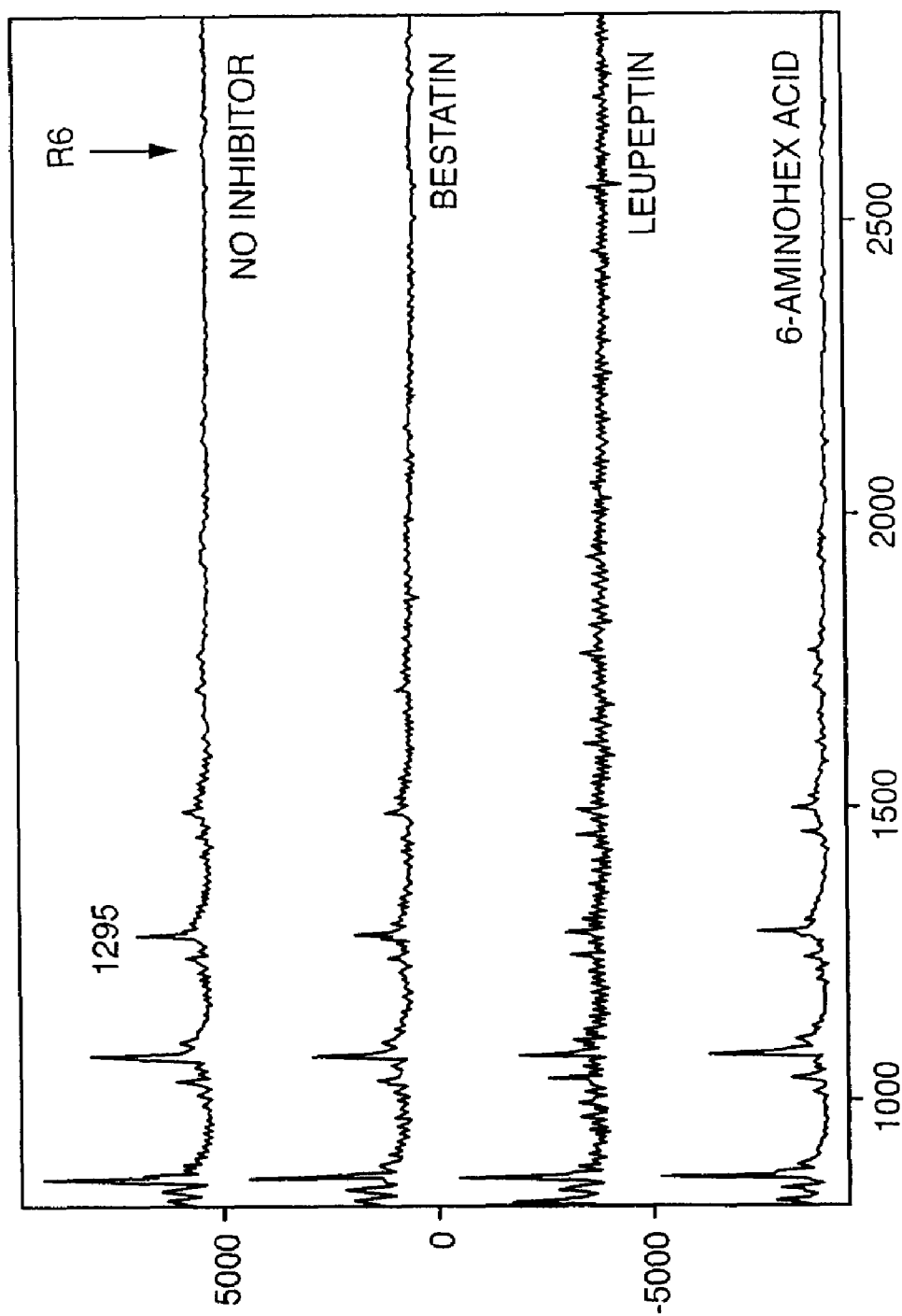

FIG. 24 is a four-panel readout of mass spec data showing that inhibiting the proteases in RR extracts (as measured by use of the reference peptide) could not be done with a single compound to a degree necessary for mass spec analysis.

Figure 25:
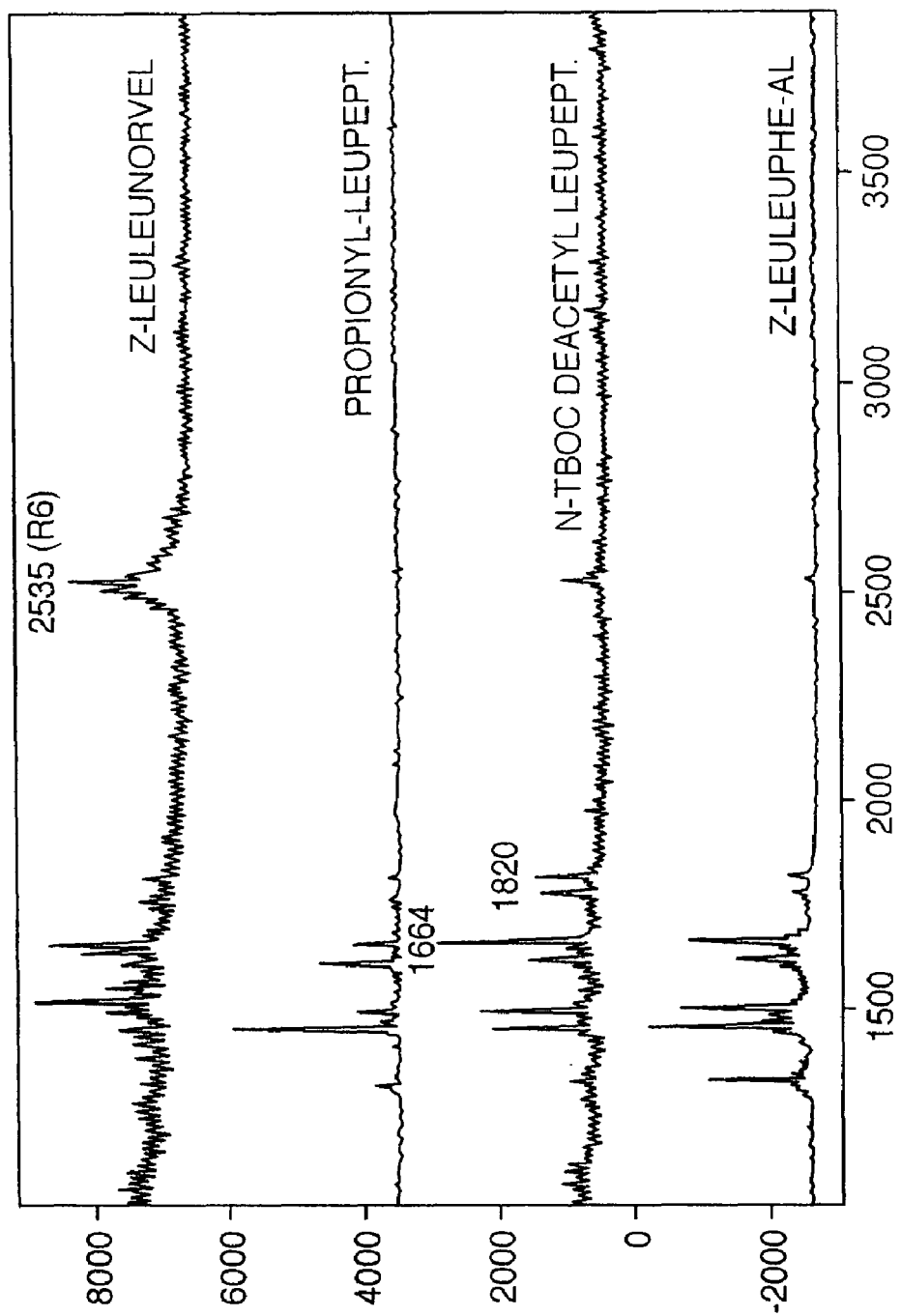

FIG. 25 is a four-panel readout of mass spec data showing that inhibiting the proteases in RR extracts (as measured by use of the reference peptide) could not be done with a single compound to a degree necessary for mass spec analysis, although some inhibition can be measured with one inhibitor (top panel).

Figure 26:
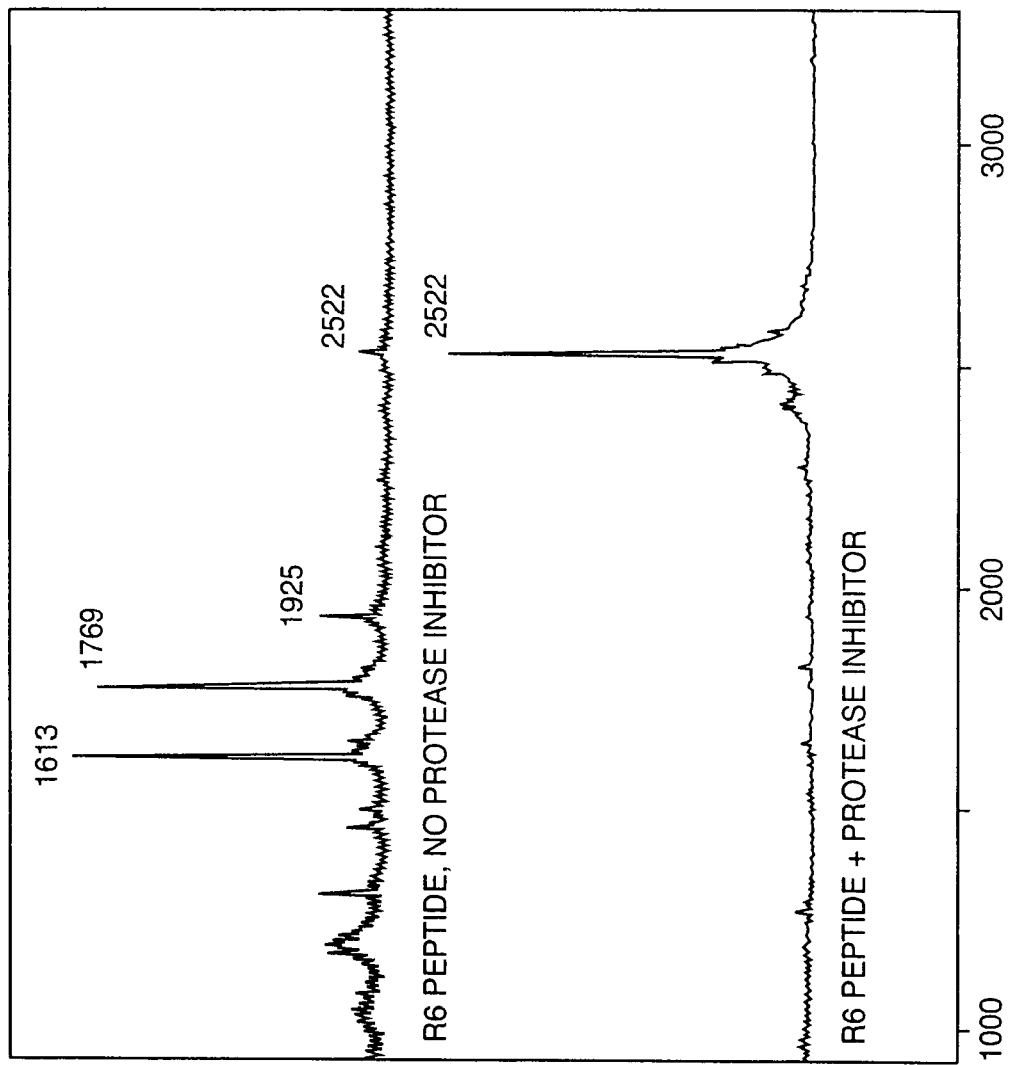

FIG. 26 is a two-panel readout of mass spec data showing that inhibiting the proteases in RR extracts (as measured by use of the reference peptide) could be done with a combination of inhibitors comprising antipain, aprotinin, calpastatin and α-BOC deacetylleupeptin (the "four inhibitor cocktail").

FIG. 27 is a five-panel readout of mass spec data comparing the inhibition of the proteases in RR extracts (as measured by use of the reference peptide) achieved with the combination of the four inhibitor cocktail (bottom) against three inhibitor cocktails. Other combinations were tested (FIG. 27) and they were either less effective (compare top panel to bottom panel) or completely ineffective (middle three panels).

Figure 28A:
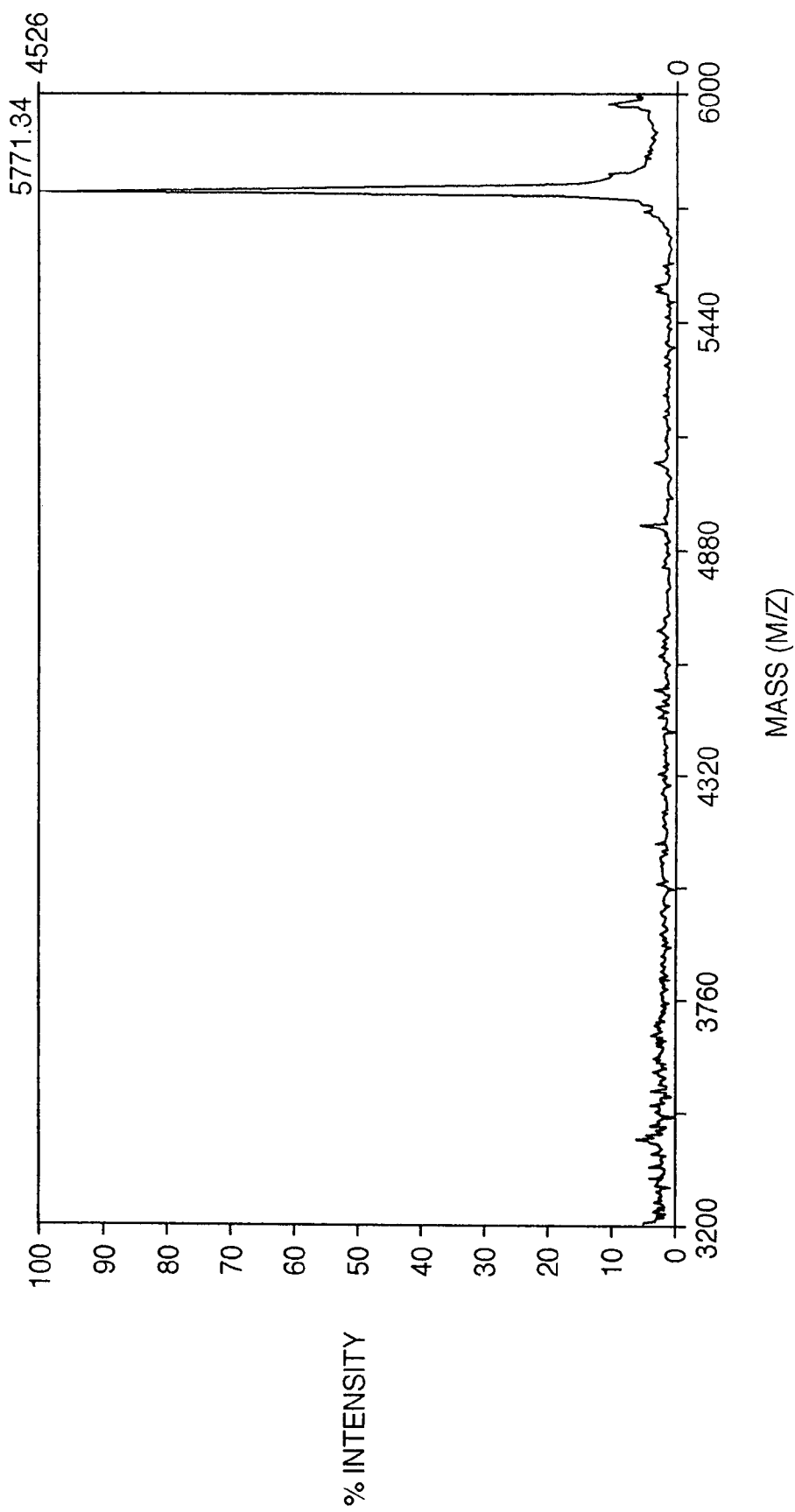
Figure 28B:
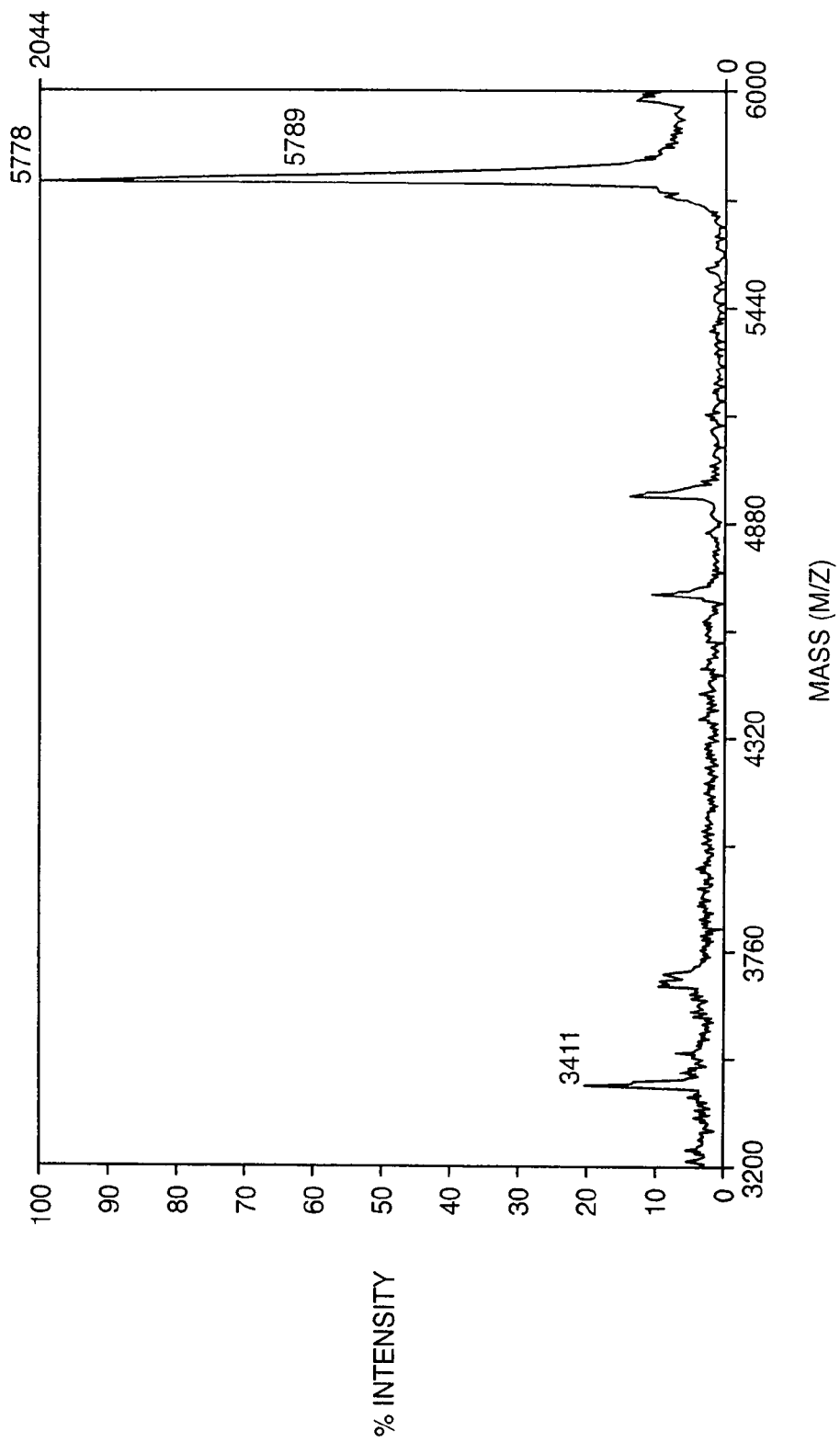

FIG. 28 is a readout of mass spec data comparing results with a commercially available reconstituted translation system that has been treated so as to deplete proteases (FIG. 28B) with the same system that has not been treated to deplete proteases (FIG. 28A).

Figure 29A:
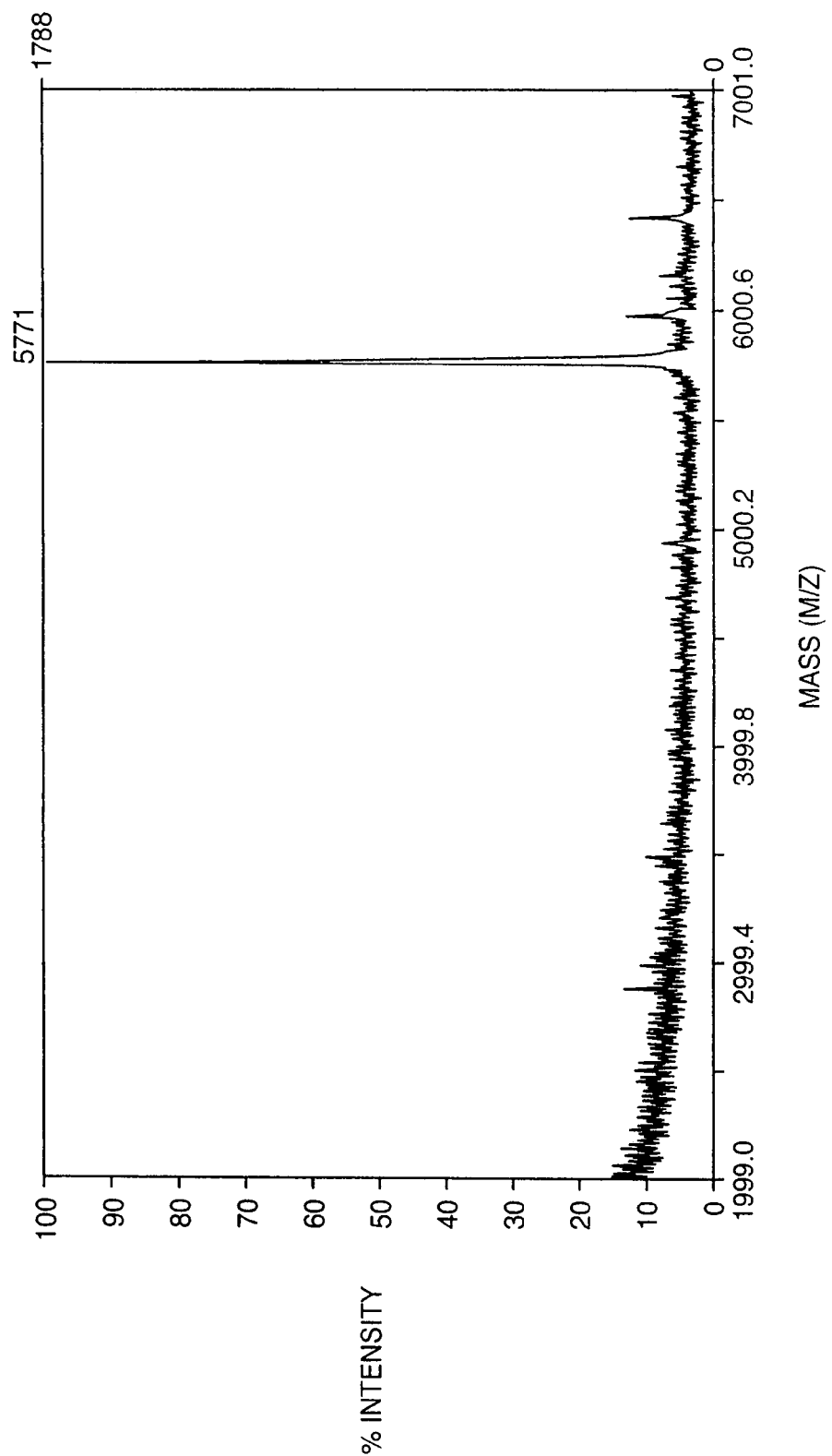
Figure 29B:
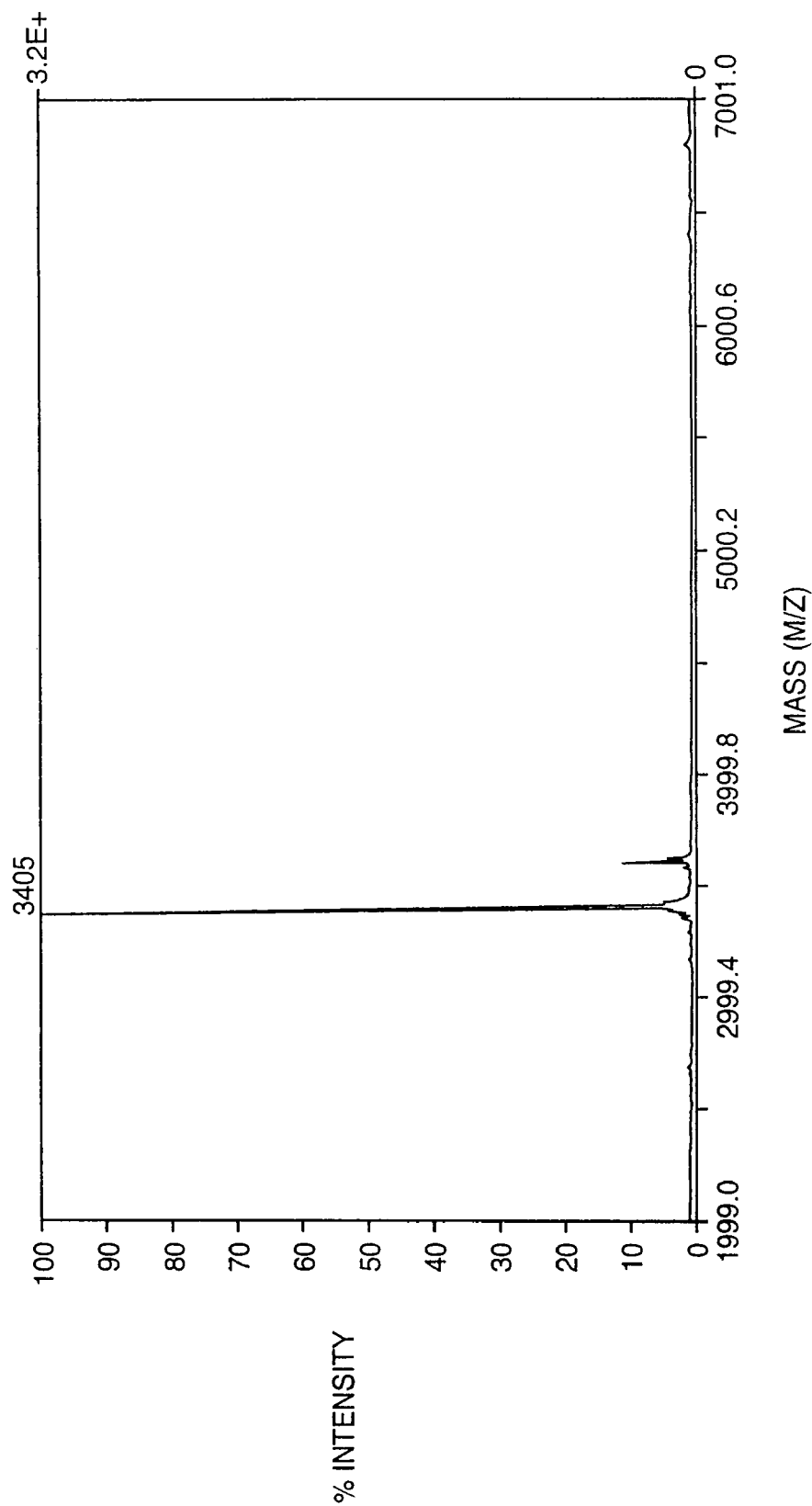
Figure 29C:
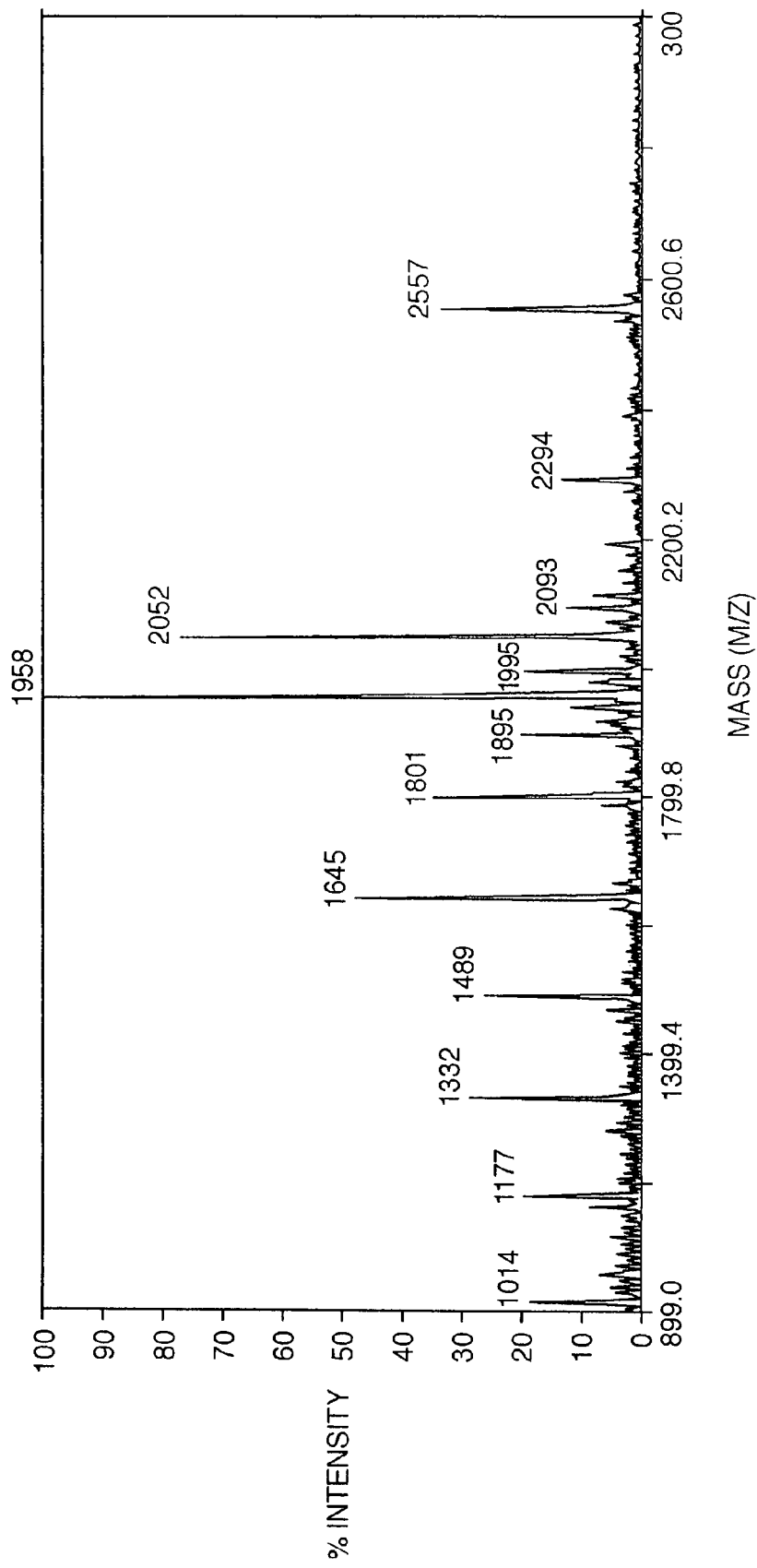
Figure 29D:
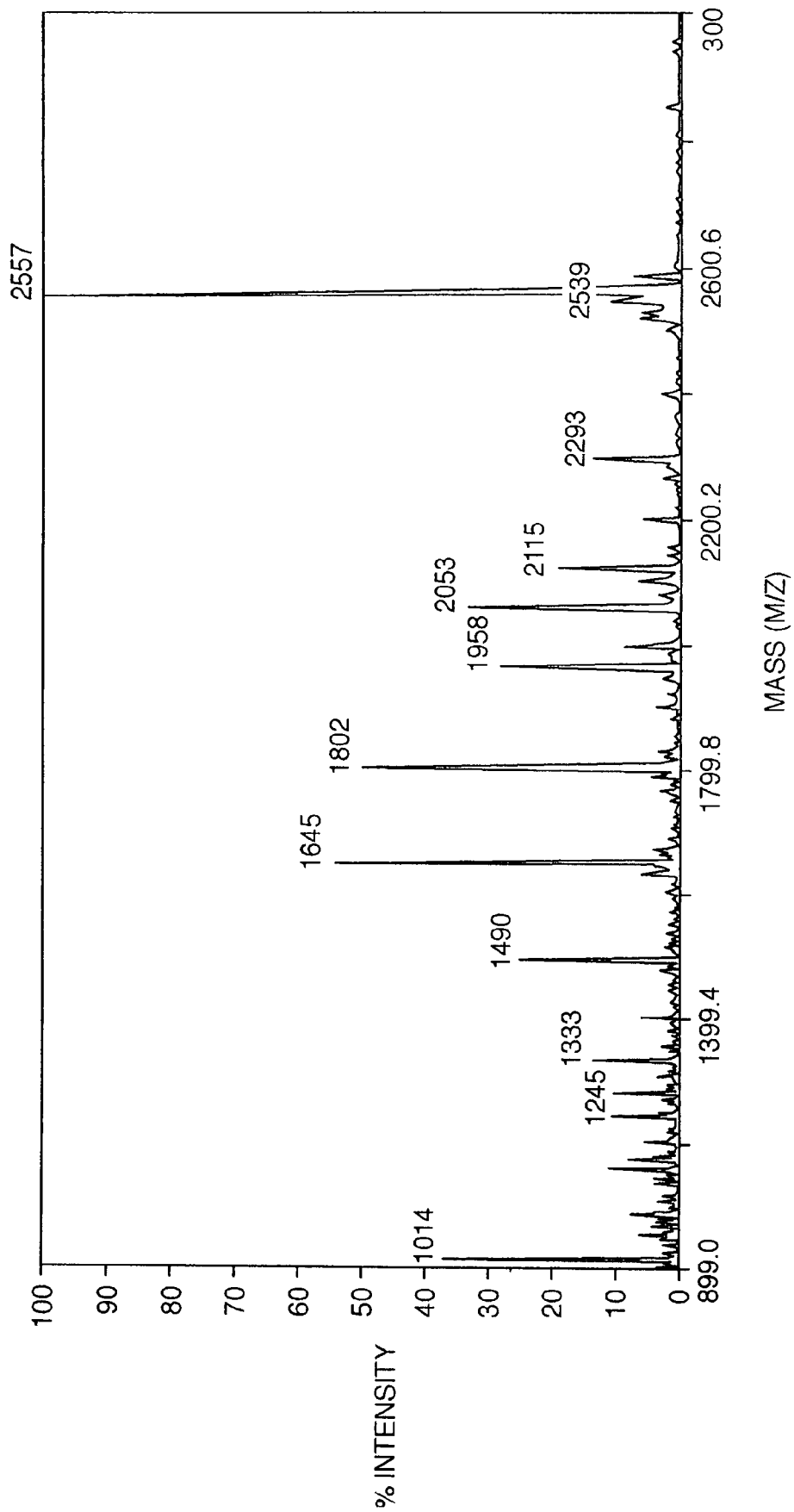

FIG. 29 is a readout of mass spec data comparing results wherein wild-type sequences are made together with truncated sequences in an in vitro translation system and are either removed by affinity chromatography comprising a ligand to the C-terminal epitope on the wild-type sequences (FIG. 29D) or not removed (FIG. 29C). FIGS. 29A and B are controls wherein wild-type sequences are made alone and truncated sequences are made alone, respectively.

Figure 30A:
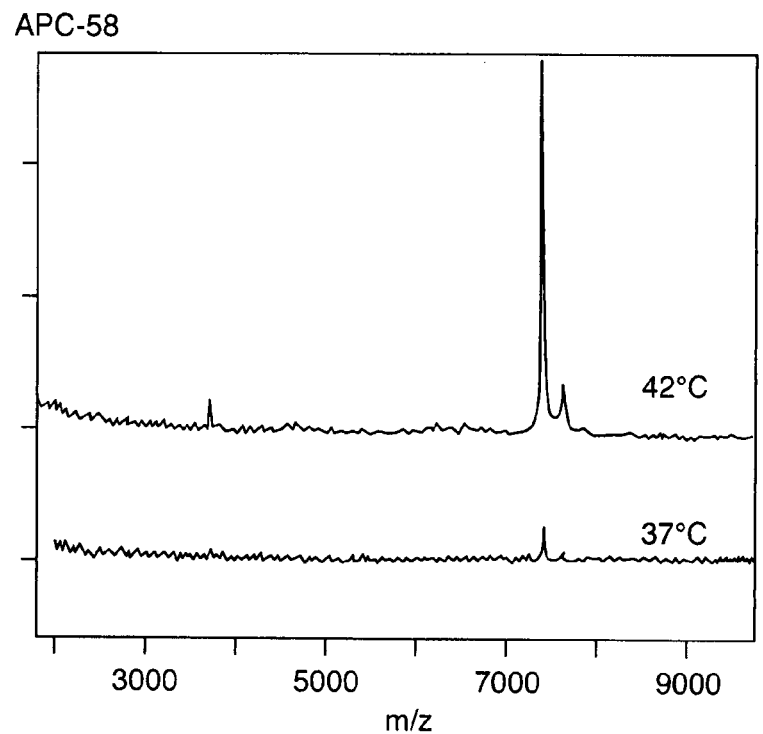

FIG. 30A is a readout of mass spec data comparing results of translation carried out at two different temperatures.

Figure 30B:
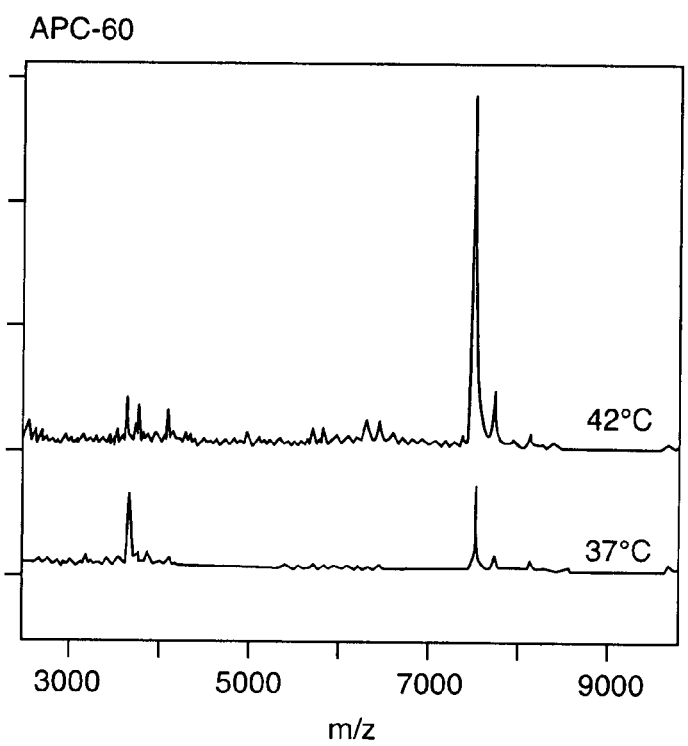

FIG. 30B is a readout of mass spec data comparing results of translation carried out at two different temperatures.

Figure 30C:
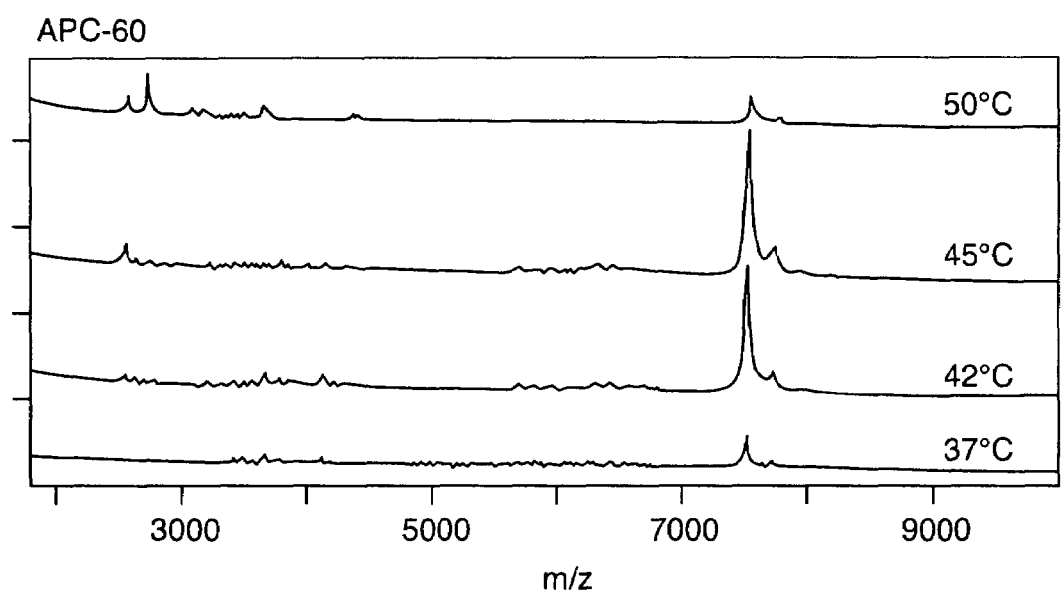

FIG. 30C is a readout of mass spec data comparing results of translation carried out at various temperatures.

Figure 31A:
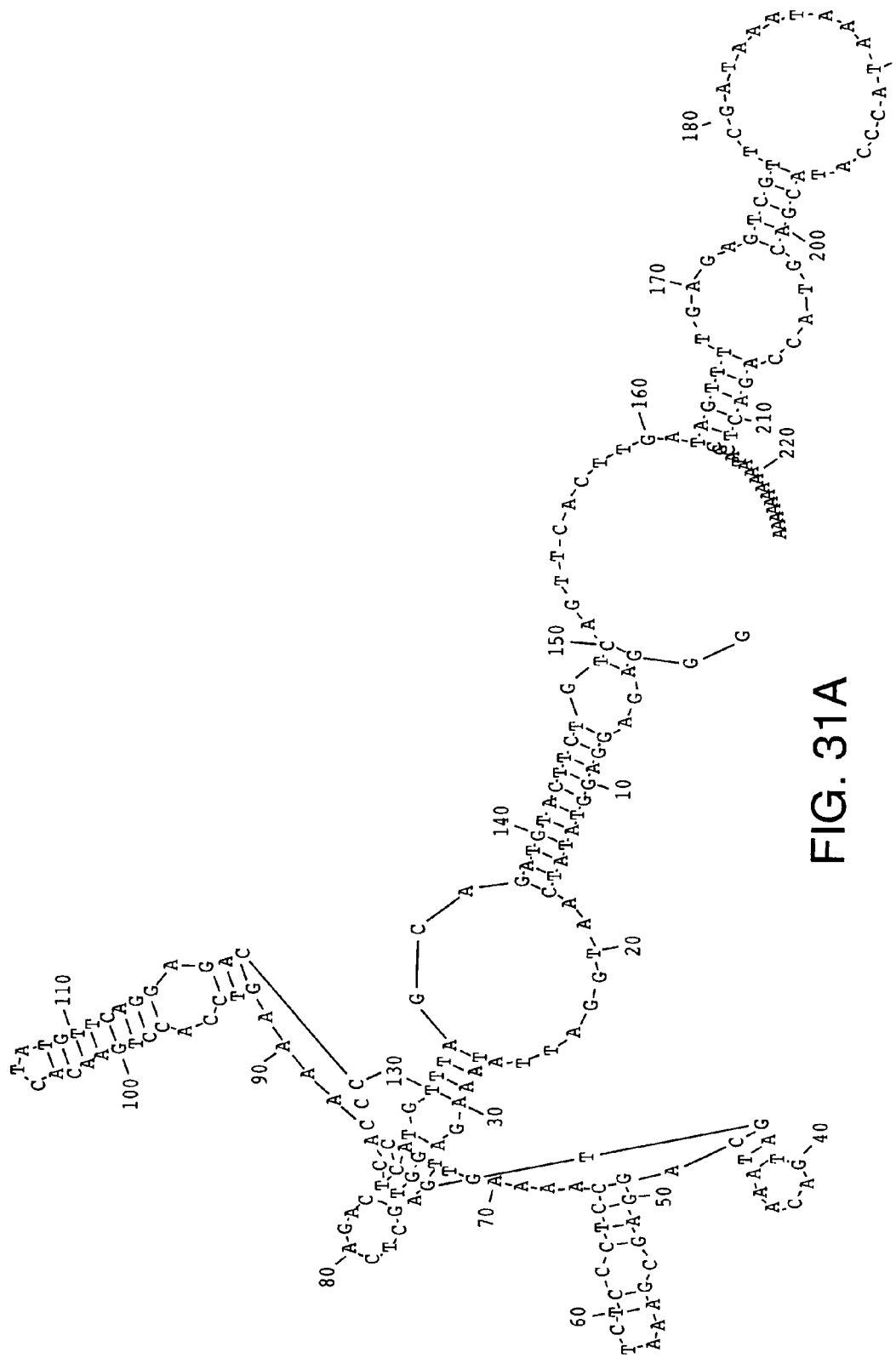

FIG. 31A is a schematic providing predicted mRNA structure.

Figure 31B:
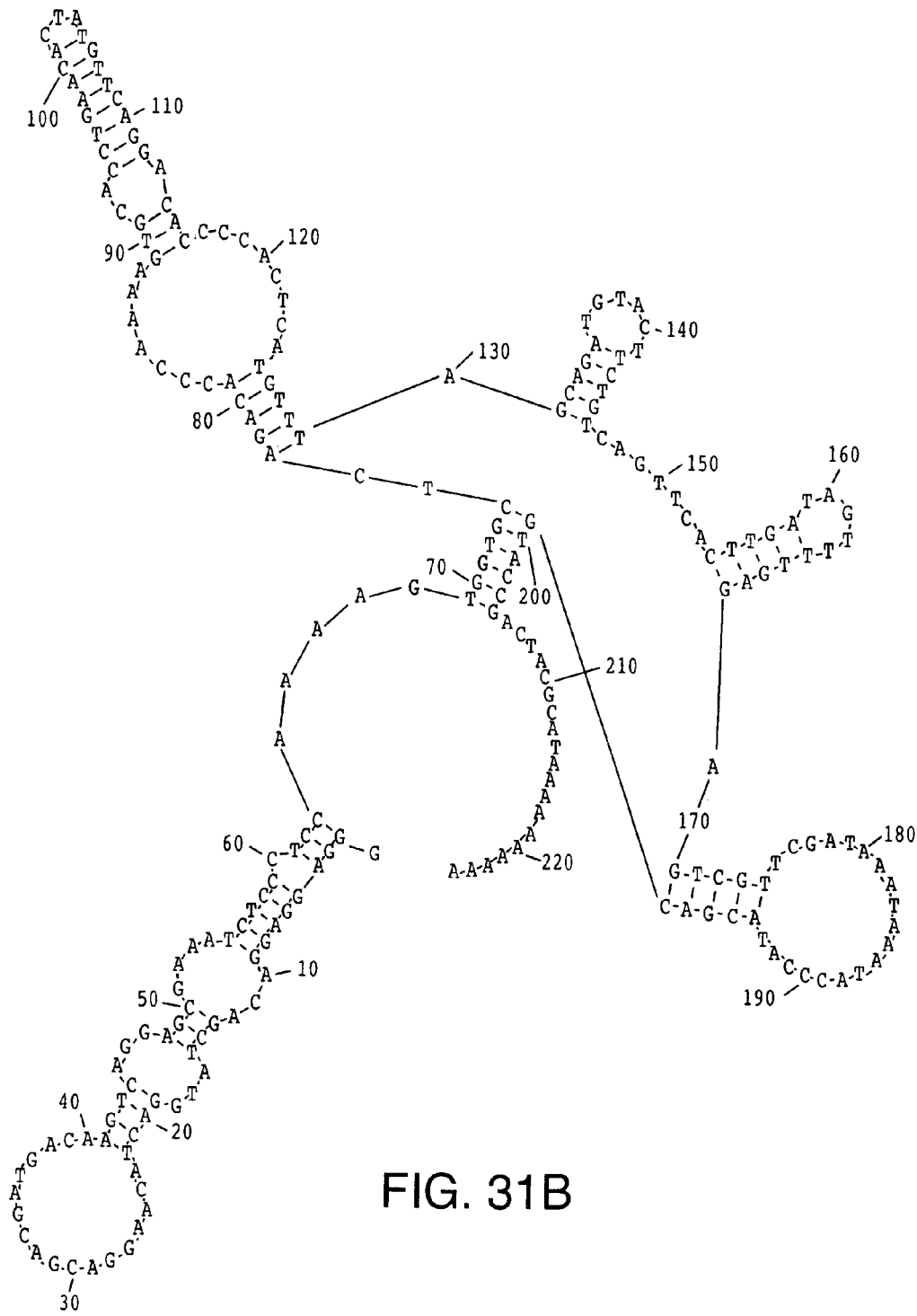

FIG. 31B is a schematic providing predicted mRNA structure.

Figure 31C:
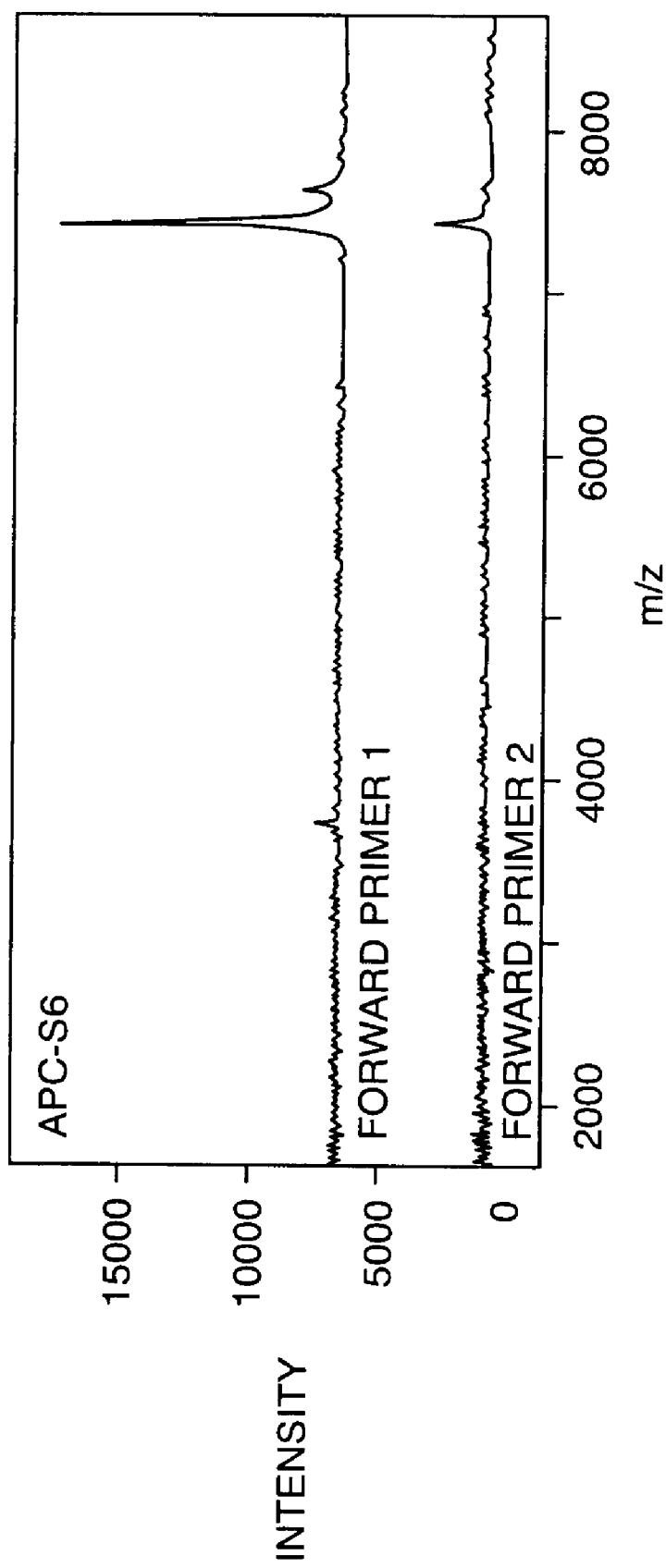

FIG. 31C is a readout of mass spec data comparing results with two different primers.

Figure 31D:
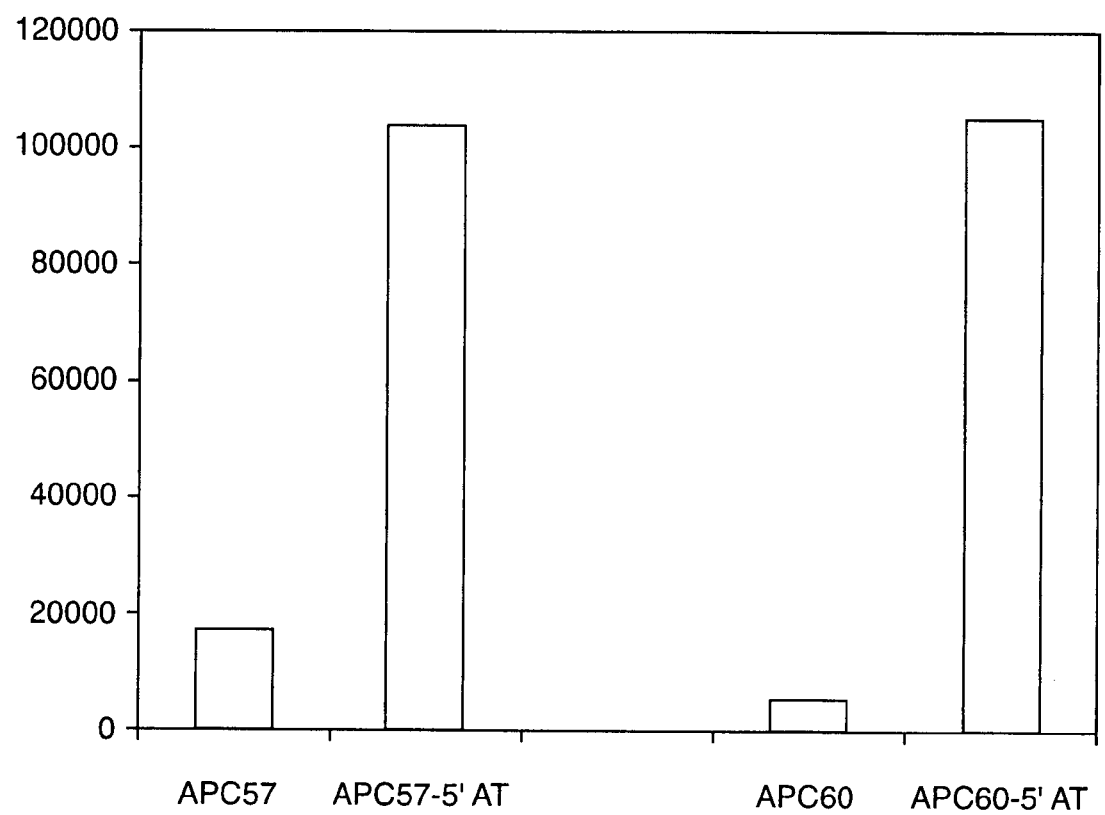

FIG. 31D is a bar graph providing a relationship of yield with secondary structure.

Figure 32:
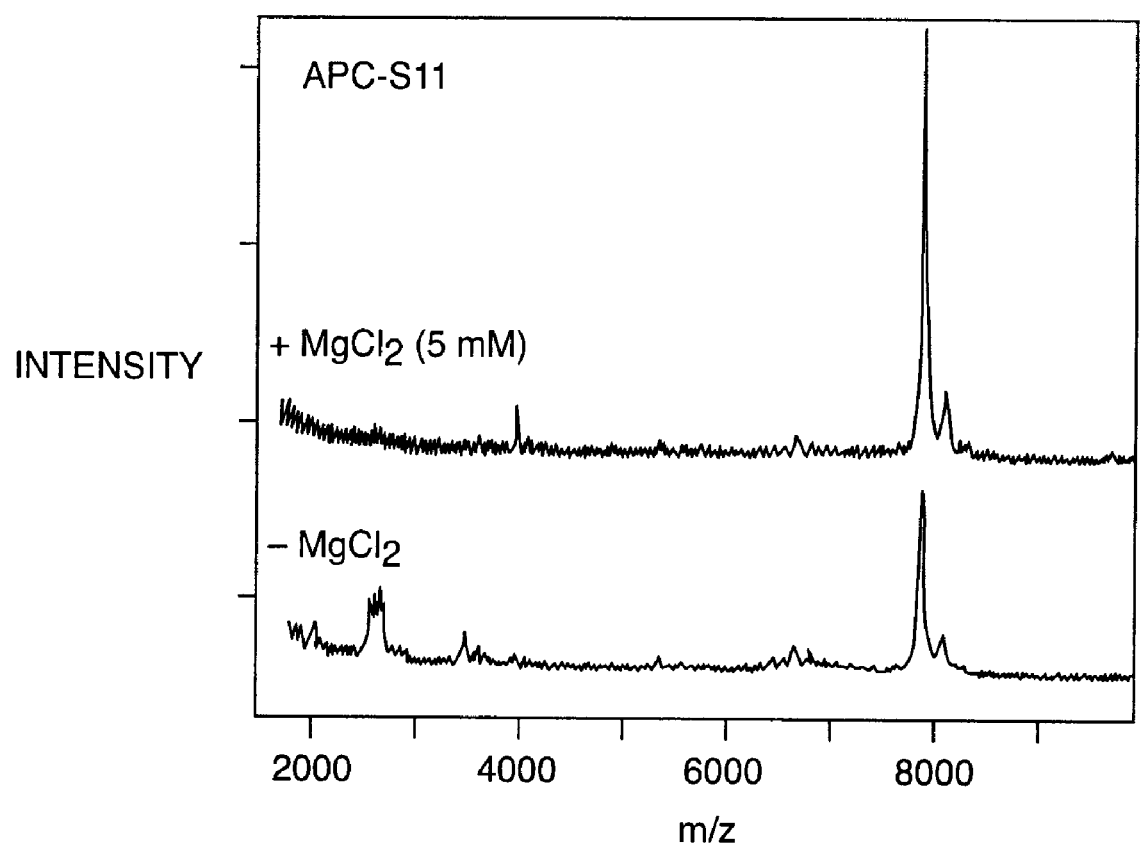

FIG. 32 is a readout of mass spec data showing results with and without added magnesium.

Figure 33:
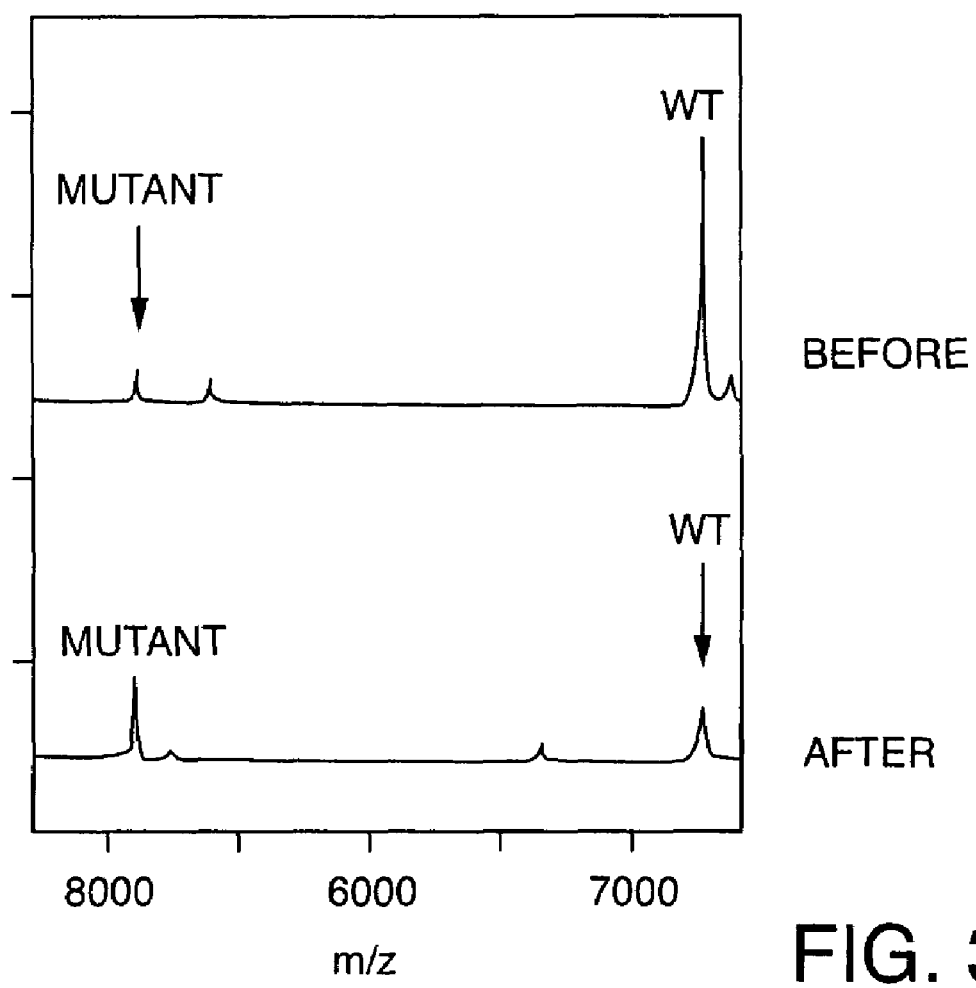

FIG. 33 is a readout of mass spec data comparing results with and without wild type depletion.

Figure 34:
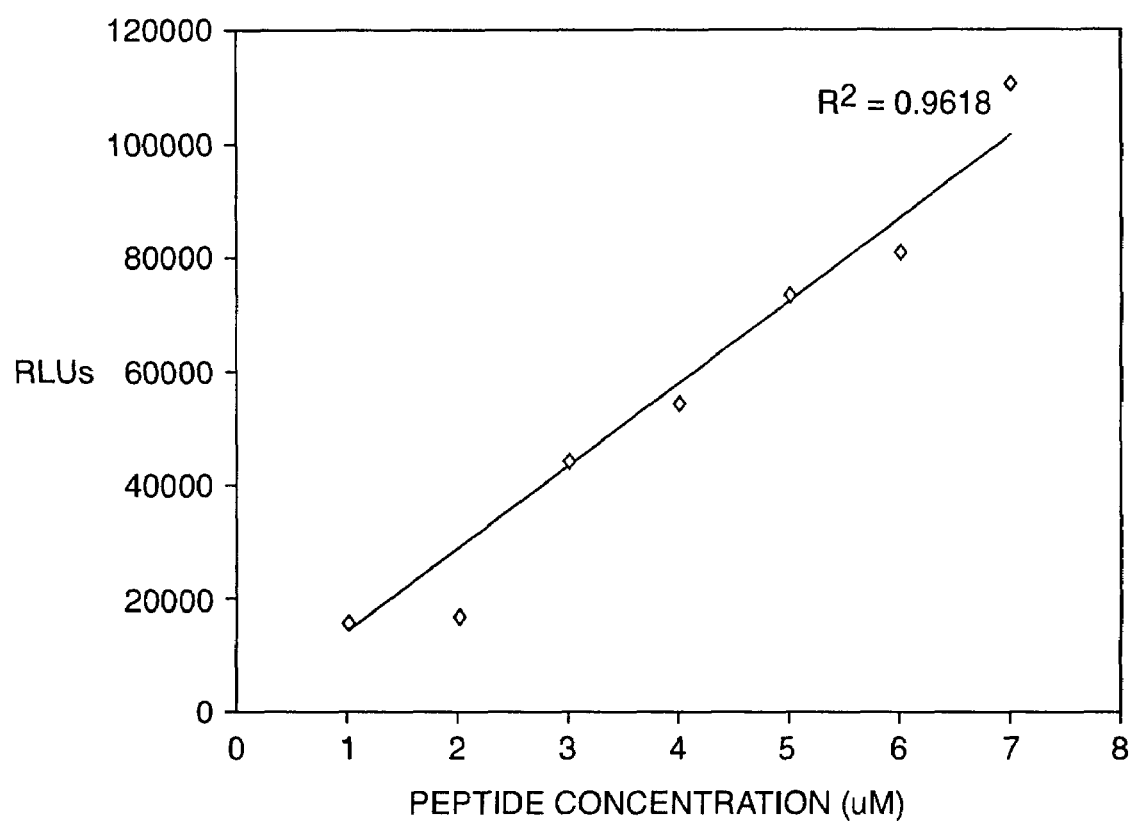

FIG. 34 is graph showing quantitation by ELISA.

Figure 35:
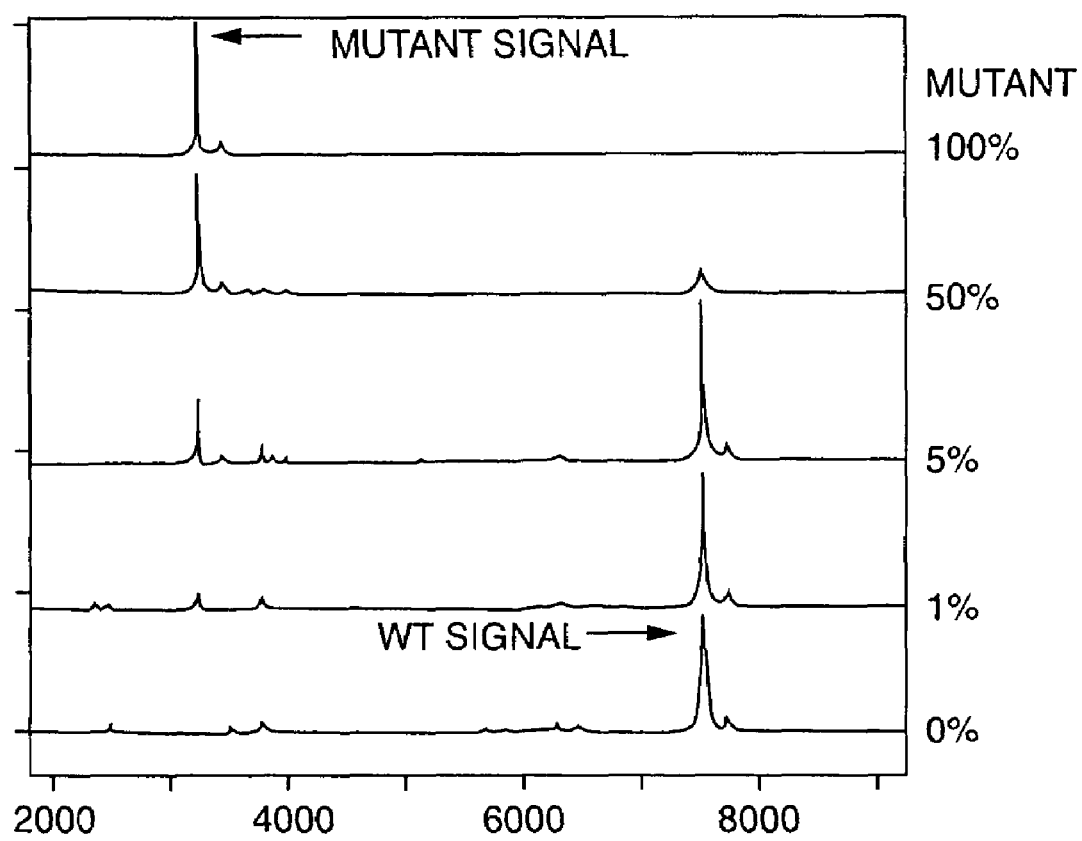

FIG. 35 is a readout of mass spec data comparing results with different mutant/WT ratios, using a 3'-primer that contains a stop codon.

Figure 36:
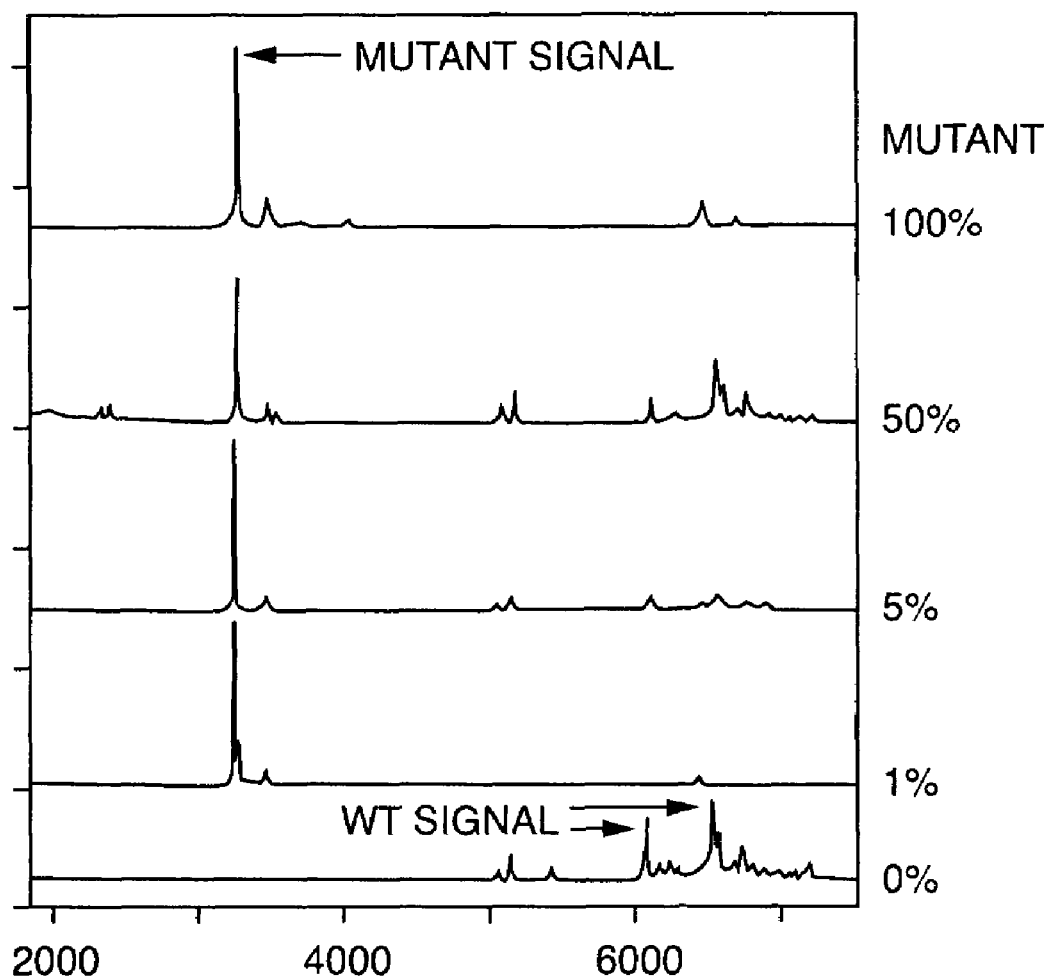

FIG. 36 is a readout of mass spec data comparing results with different mutant/WT ratios, using a 3'-primer that lacks a stop codon.

Figure 37:
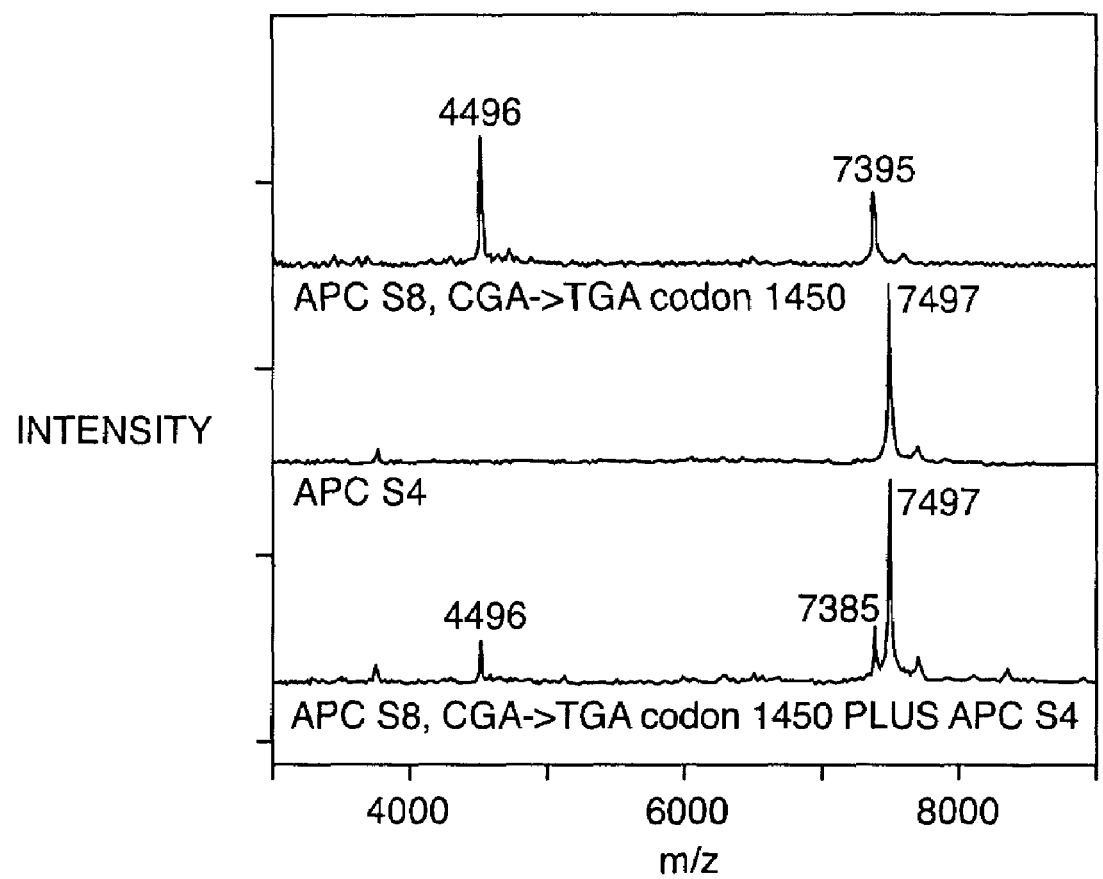

FIG. 37 is a readout of mass spec data. The top trace represents single-plex mass spectrum of the heterozygous mutant CGA→TGA in codon 1450 in the segment S8. The middle trace represents single-plex mass spectrum of the wild type APC segment S4. The bottom trace corresponds to multiplex spectrum obtained from the single translation reaction containing DNA mixture (1:1) for segments S4 and S8. Peaks from both wild-type and mutant APC S8 as well as S4 are evident.

Figure 38:
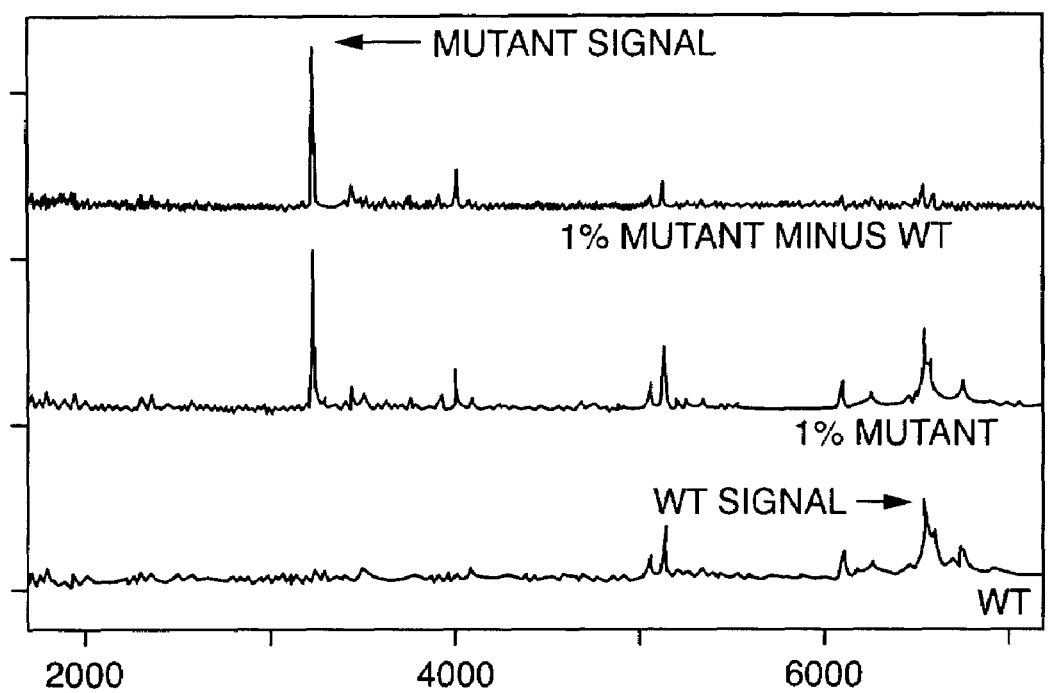

FIG. 38 is a readout of mass spec data. The bottom trace represents WT sample mass spectrum; the middle trace: 1% mutant sample mass spectrum; and the top trace: background subtracted 1% mutant sample spectrum.

Figure 39A:
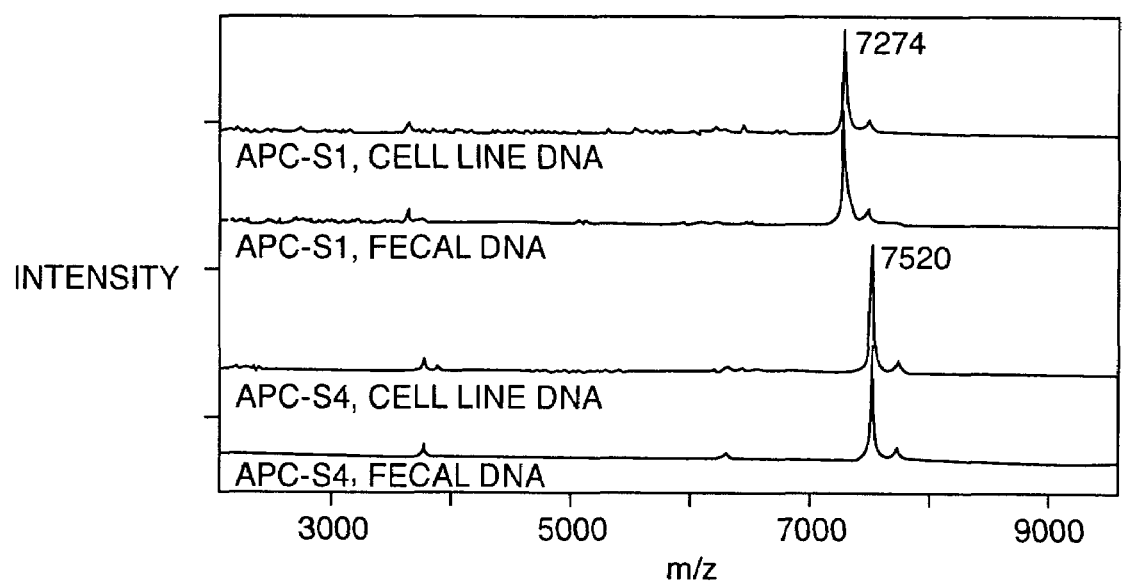
Figure 39B:
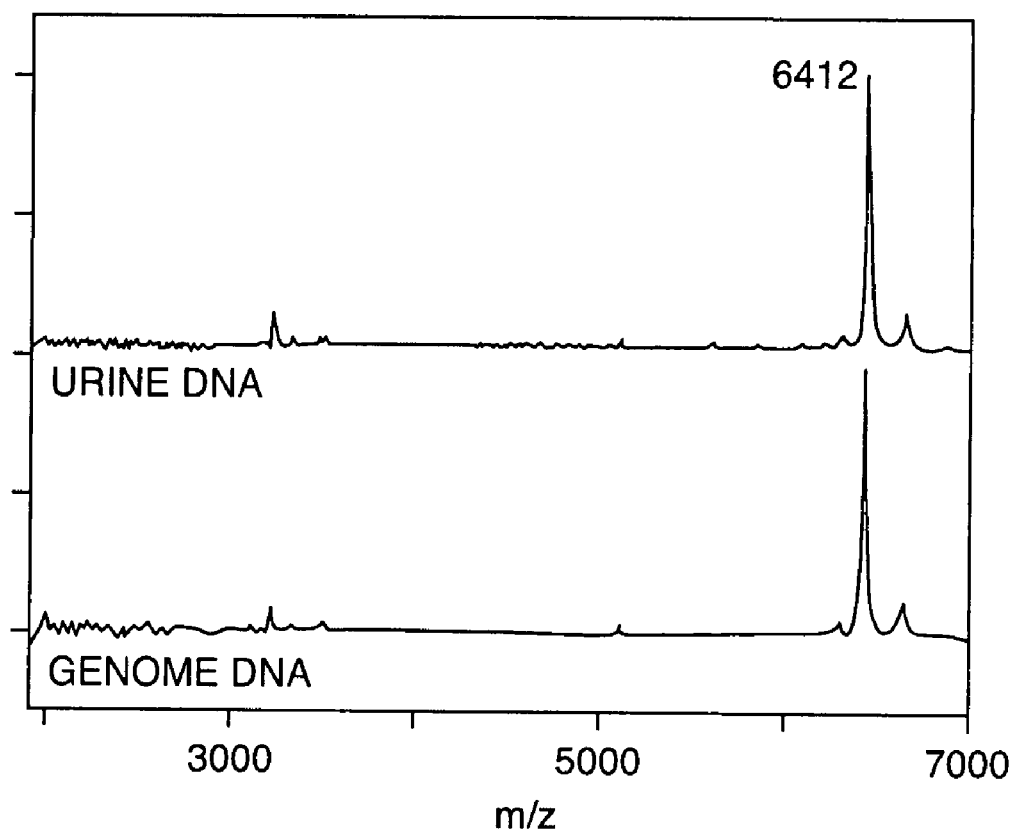
Figure 39C:
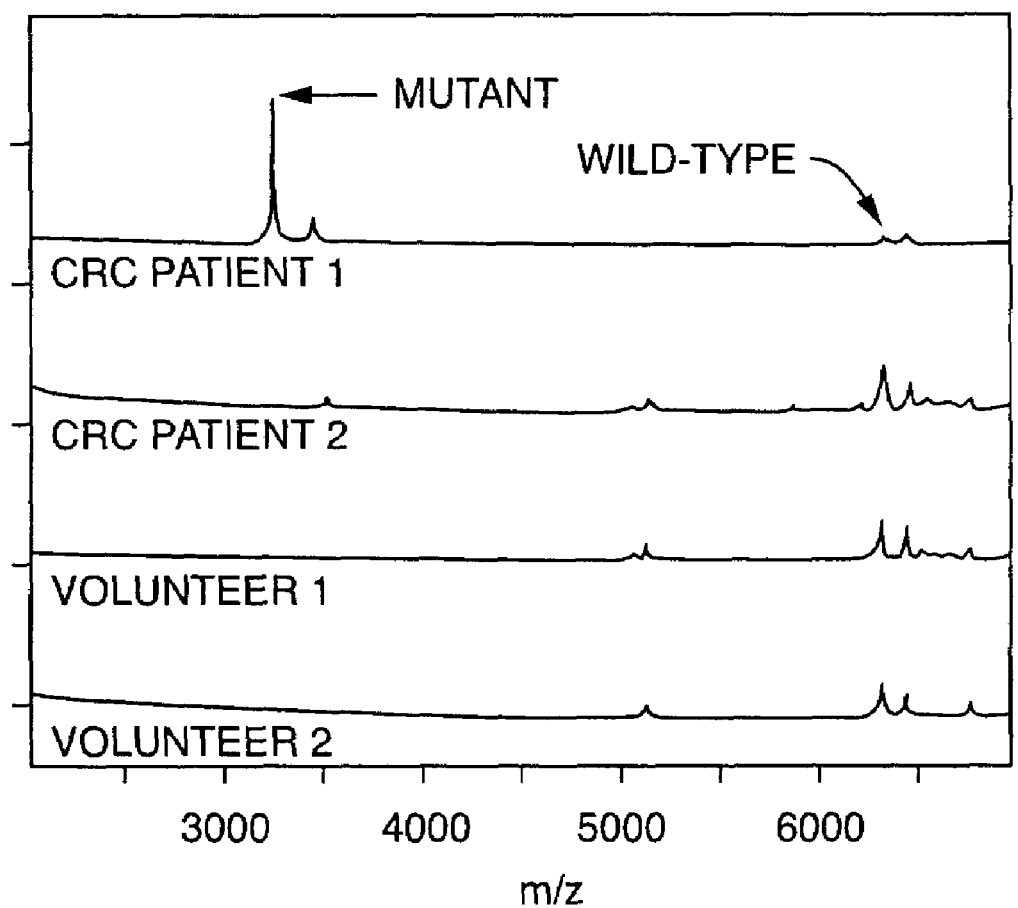

FIG. 39A shows the results of one embodiment of MASSIVE-PRO for S1 & S4 APC segments (see FIG. 44) using PCR amplicons derived from cell-line DNA and stool DNA. FIG. 39B shows the results of one embodiment of MASSIVE-PRO for S4 APC segment using PCR amplicons derived from human genomic DNA and urine DNA. FIG. 39C shows the results of one embodiment of MASSIVE-PRO for S4 APC segment using PCR amplicons derived from DNA isolated from stool of healthy volunteers and colorectal cancer (CRC) patients.

Figure 40:
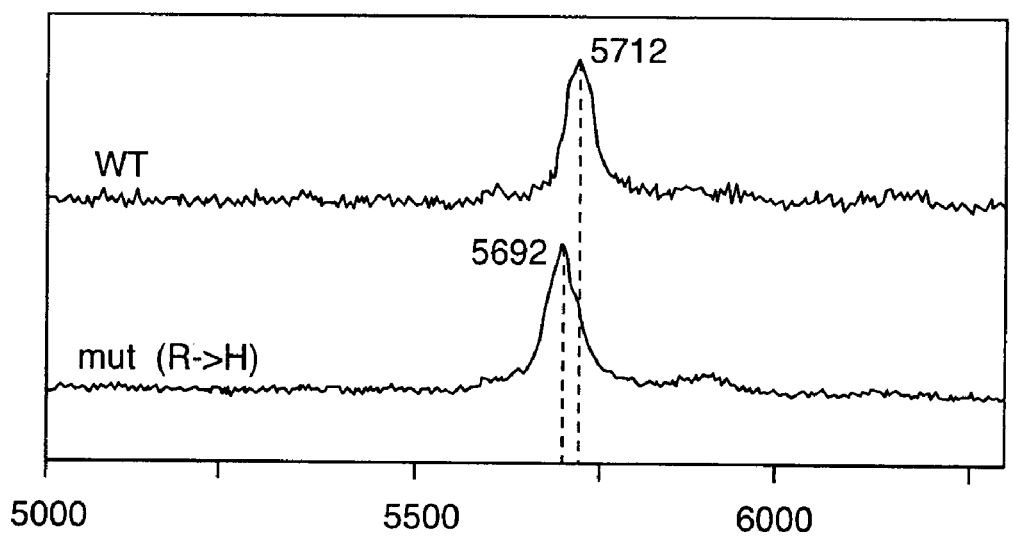

FIG. 40 is a readout of mass spec data comparing results of one embodiment of MASSIVE-PRO for mutation detection in P53 gene (Exon 5: Codons 158-186) using MALDI-TOF. The top trace shows the WT and the bottom trace shows an R→H mutation at codon 175 producing the predicted 20 Daltons shift.

Figure 41:
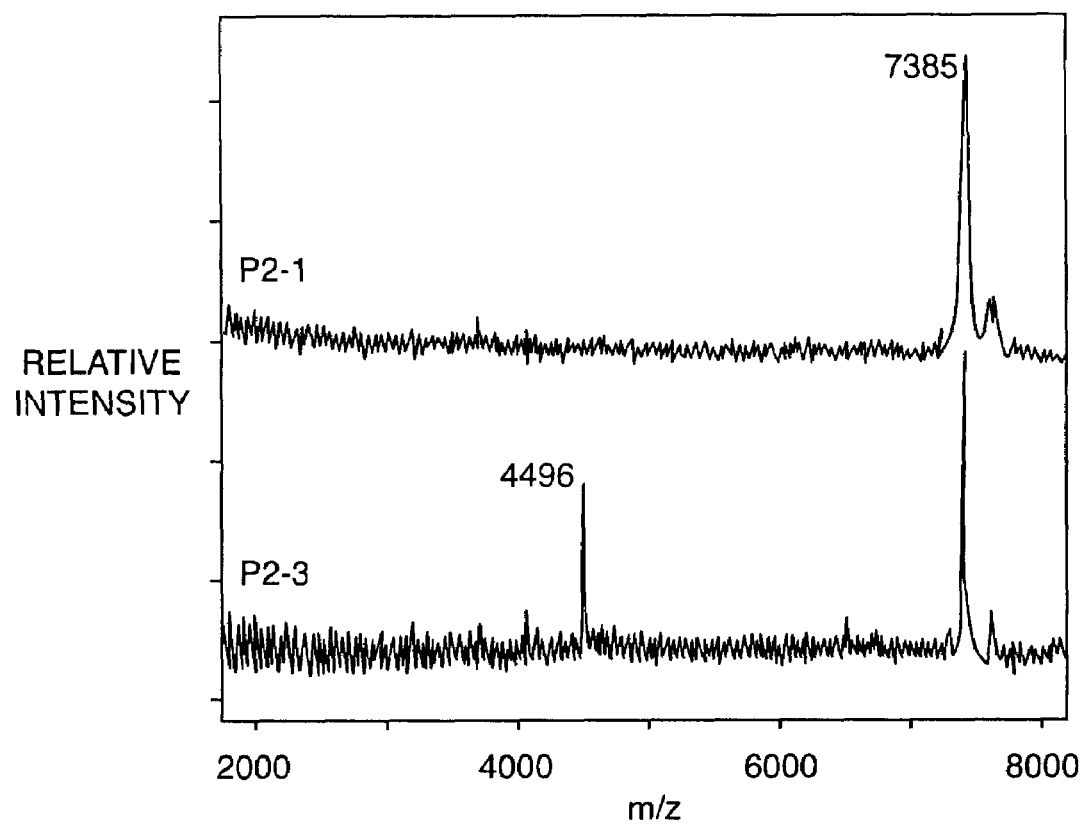

FIG. 41 is a readout of mass spec data comparing results of one embodiment of MASSIVE-PRO for mutation detection in APC gene using the DNA isolated from polyps. P2-1 is WT and P2-3 is mutant sample. Top: P2-1 is WT sample & bottom: P2-2 is a polyps sample with CGA->TGA mutation at codon 1450 in APC gene which gives the truncated product of predicted mass of 4496 Da.

Figure 42:
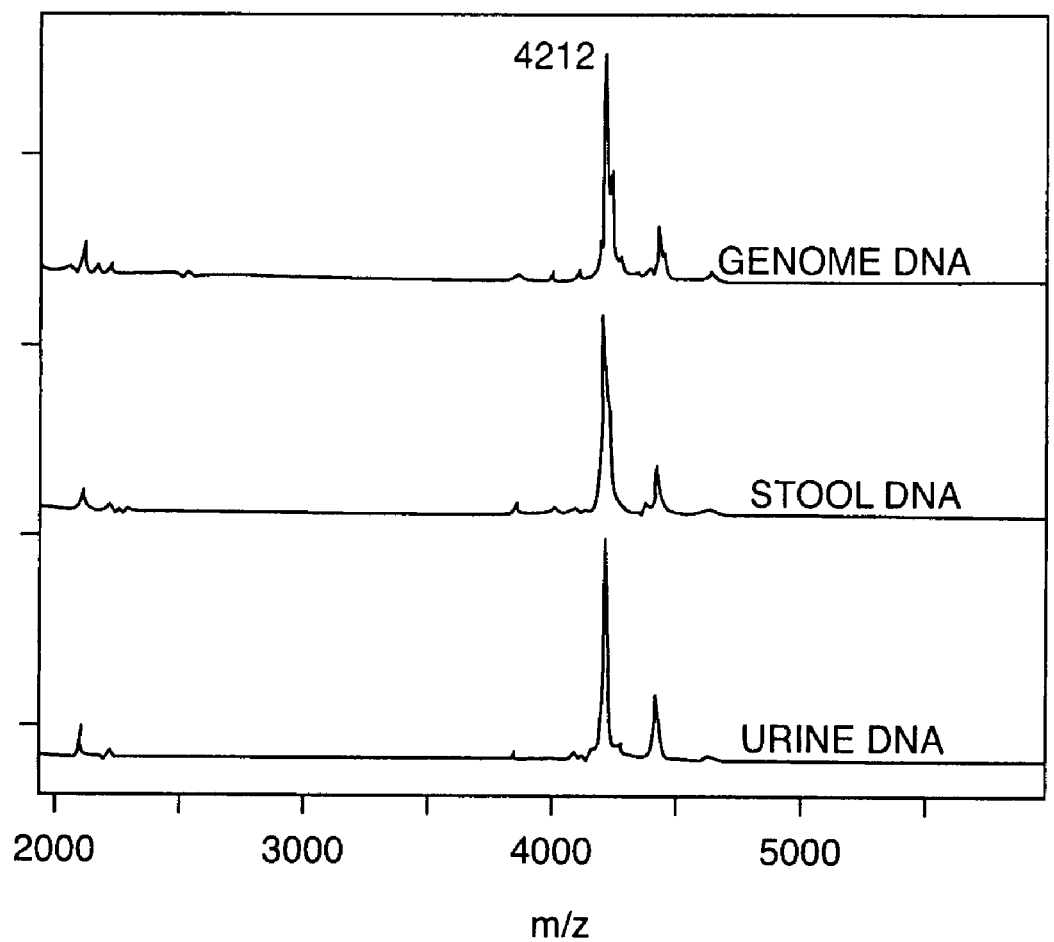

FIG. 42 is a readout of mass spec data comparing results of one embodiment of MASSIVE-PRO for mutation detection in K-RAS gene using the DNA isolated from normal human blood, stool and urine samples. All the samples show WT K-RAS peak at 4212 Da.

Figure 43:
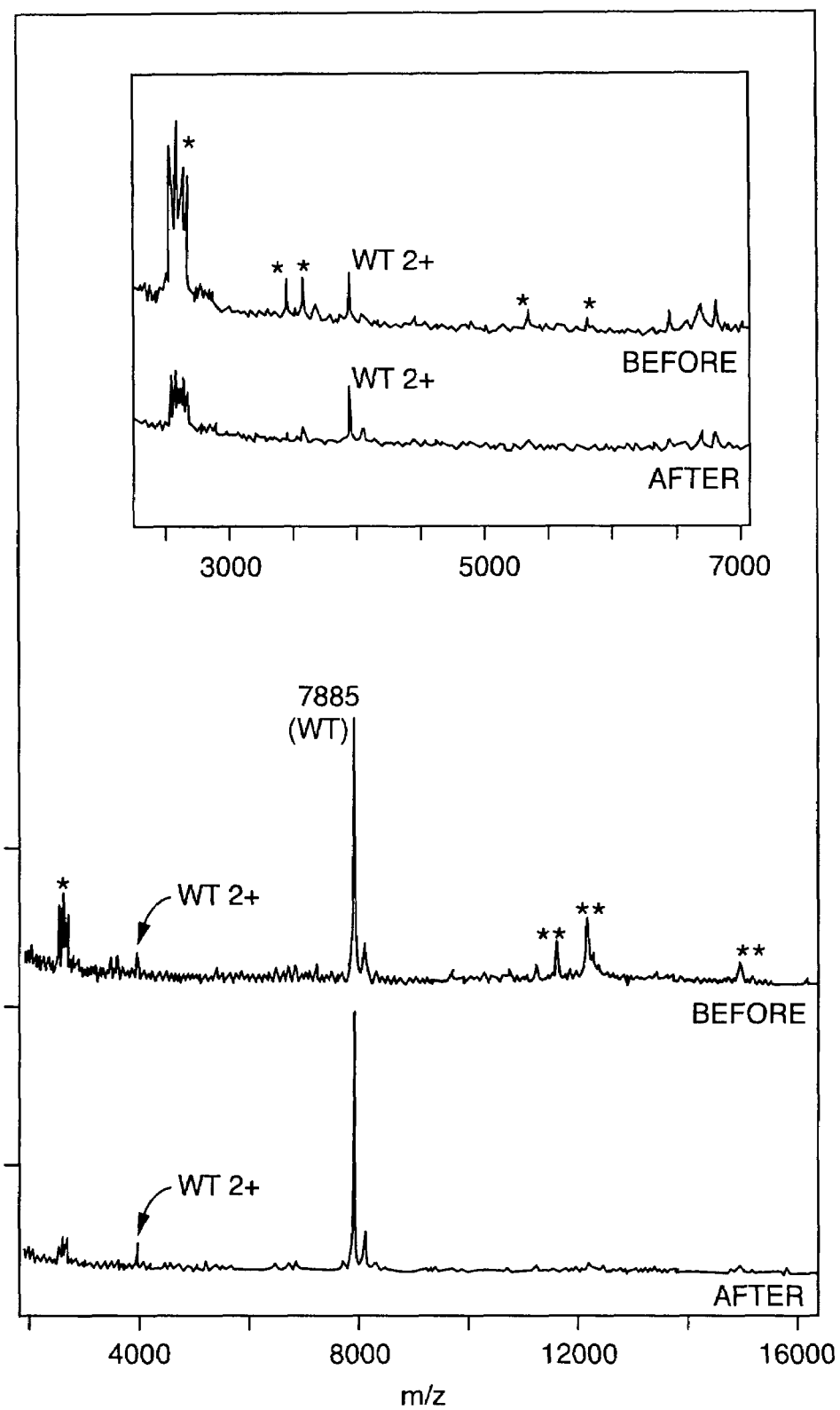

FIG. 43 is a readout of mass spec data showing the removal of background peaks by ribosome depletion prior to FLAG purification. Top spectrum: FLAG purification without ribosome depletion. Bottom spectrum is FLAG purification after ribosome depletion using YM-100 membrane filtration. Inset: Magnified spectrums from 3000-7000 Da.

Figure 44:
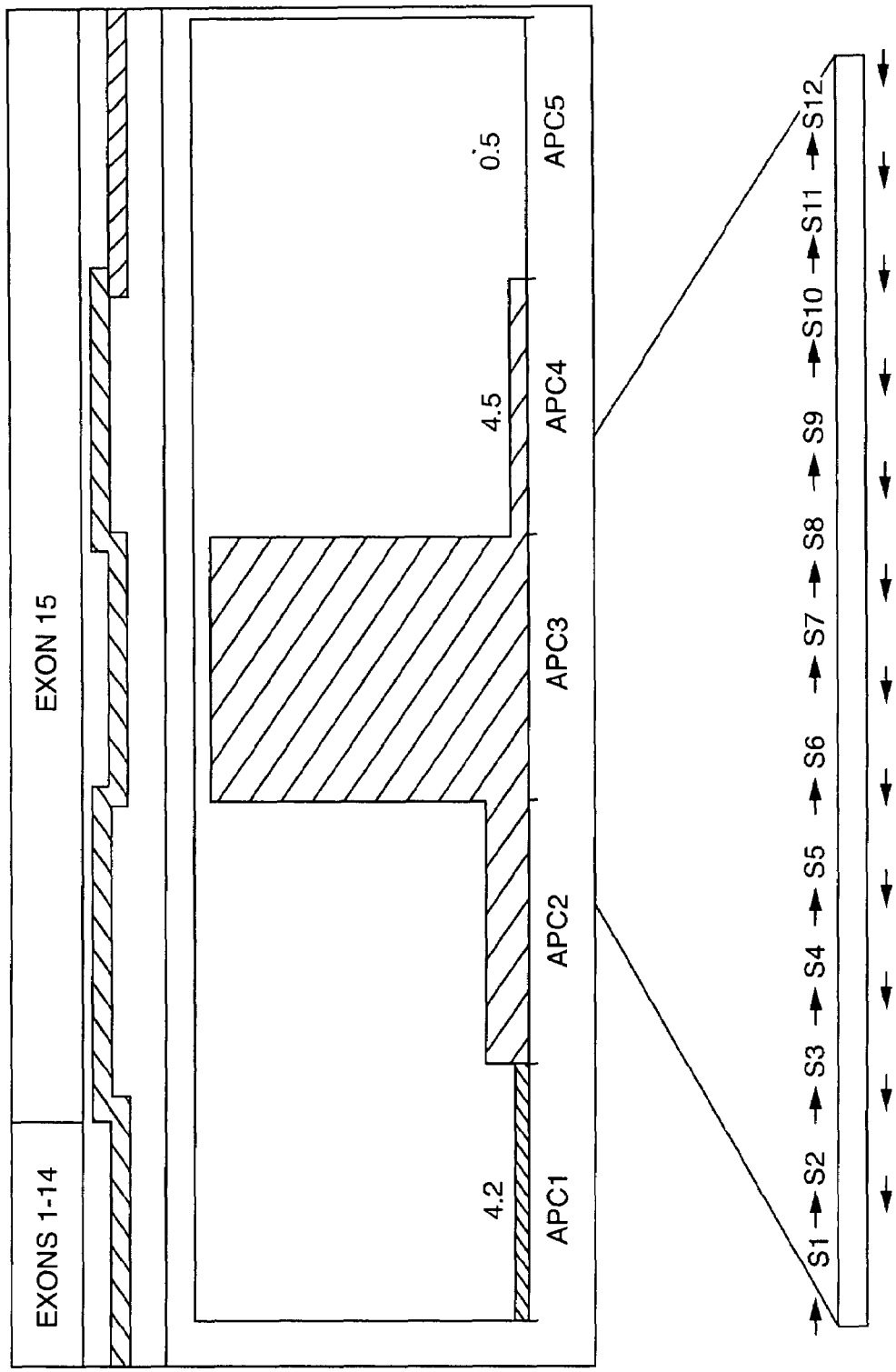

FIG. 44 is a schematic of primer design for APC gene showing Mutation Cluster Region (MCR) which is divided into 12 segments for one embodiment of the MASSIVE-PRO assay.

DESCRIPTION OF THE INVENTION

Nonsense or frameshift mutations, which result in a truncated gene product, are prevalent in a variety of disease-related genes. Den Dunnen et al., *The Protein Truncation Test: A Review*. Hum Mutat 14:95-102 (1999). Specifically, these diseases include: i) APC (colorectal cancer), Powell et aL, *Molecular Diagnosis Of Familial Adenomatous Polyposis*. N Engl J Med 329:1982-1987 (1993); van der Luijt et al., *Rapid Detection Of Translation-Terminating Mutations At The Adenomatous Polyposis Coli (APC) Gene By Direct Protein Truncation Test*. Genomics 20:1-4 (1994); Traverso et al., *Detection Of APC Mutations In Fecal DNA From Patients With Colorectal Tumors*. N Engl J Med 346:311-320 (2002); Kinzler et al., *Identification Of A Gene Located At Chromosome 5q21 That Is Mutated In Colorectal Cancers*. Science 251:1366-1370 (1991); and Groden et al., *Identification And Characterization Of The Familial Adenomatous Polyposis Coli Gene*. Cell 66:589-600 (1991); ii) BRCA1 and BRCA2 (breast and ovarian cancer), Hogervosrt et al., *Rapid Detection Of BRCA1 Mutations By The Protein Truncation Test*. Nat Genet 10:208-212 (1995); Garvin et al., *A Complete Protein Truncation Test For BRAC1 and BRAC2*. Eur J Hum Genet 6:226-234 (1998); Futreal et al., *BRAC1 Mutations In Primary Breast And Ovarian Carcinomas*. Science 266:120-122 (1994); iii) polycystic kidney disease, Peral et al., *Identification Of Mutations In the Duplicated Region Of The Polycystic Kidney Disease 1 Gene (PKD1) By A Novel Approach*. Am J. Hum Genet 60:1399-1410 (1997); iv) neurofibromatosis (NF1 and NF2), Hein et al., *Distribution Of 13 Truncating Mutations In The Neurofibromatosis 1 Gene*. Hum Mol Genet 4:975-981 (1995); Parry et al., *Germ-line Mutations In The Neurofibromatosis 2 Gene: Correlations With Disease Severity And Retinal Abnormalities*. Am J Hum Genet 59:529-539 (1996).; and v) Duchenne muscular dystrophy (DMD), Roest et al., *Protein Truncation Test (PTT) To Rapidly Screen The DMD gene For Translation Terminating Mutations*. Neuromuscul Disord 3:391-394 (1993). Such chain truncating mutations can be detected using the protein truncation test (PTT). This test is based on cell-free coupled transcription-translation of PCR (RT-PCR) amplified portions of the target gene (target mRNA) followed by analysis of the translated product(s) for shortened polypeptide fragments. However, conventional PTT is not easily adaptable to high throughput applications since it involves SDS-PAGE followed by autoradiography or Western blot. It is also subject to human error since it relies on visual inspection to detect mobility shifted bands.

To overcome these limitations, we have developed the first high throughput and high sensitivity truncation test utilizing mass spectrometry. This approach uses specially designed PCR primers, which introduce N- and C-terminal markers (e.g. epitopes). After translation of the protein fragments, capture and detection is accomplished using a ligand which binds the N-terminal epitope. The C-terminal epitope can be used to deplete wild-type sequence. Thereafter, wild-type and truncated products are detected by mass spectrometry.

It was previously not appreciated that small truncation products would be difficult to assess by mass spectrometry because of susceptibility to proteolysis during translation. Even with a reconstituted translation system, polypeptides in the 5 to 150 amino acid size range (and in particular, polypeptides in the 10 to 60 amino acid size range) are quickly degraded, complicating (if not completely preventing) analysis. Since the problem was not recognized, no solutions were explored. Moreover, solving the problem with protease inhibitors is not straightforward in that a) many inhibitors do not inhibit, and b) some inhibitors that inhibit proteolysis also inhibit translation. In one embodiment, the present invention provides, on the other hand, protease inhibitors (single compounds for the reconstituted systems and combinations for other systems) which do not significantly interfere with translation at the levels needed to inhibit proteolysis. In another embodiment, components in the reconstituted system are manipulated so as to reduce proteases in the mixture. In another embodiment, combinations of these approaches can be utilized.

Thus, in one embodiment where one or more components are manipulated, the present invention contemplates a method, comprising: a) providing i) a cell-free translation system comprising a first preparation comprising first ribosomes in solution, and ii) second ribosomes; b) removing at least a portion of said first ribosomes from said solution (e.g. by filtration, centrifugation, precipitation, etc.) so as to create a depleted solution; c) adding second ribosomes to said depleted solution so as to create a second preparation, wherein the protease activity of said first preparation is greater than the protease activity of said second preparation. In a preferred embodiment, said second ribosomes are ribosomes purified by zonal centrifugation. It is particularly preferred that protease activity of said first and second preparations is measured using mass spectrometry, such as the mass spec-based protease assay described herein which employs a (non-naturally occurring) protease-sensitive peptide.

Regardless of the approach, the present invention contemplates in one embodiment a method, comprising: providing: i) a nucleic acid sequence encoding a polypeptide, said polypeptide being between 10 and 150 amino acids in length (and more preferably between 10 and 100 amino acids in length, and still more preferably between 10 and 80 amino acids in length); and ii) an in vitro translation system; and introducing said nucleic acid into said translation system under conditions such that said polypeptide is produced, wherein said polypeptide is degraded by less than 50% (and more preferably by less than 30%) by proteolysis following exposure to said translation system for approximately 10 minutes (and more preferably, for 20 minutes) at approximately 37° C. In one embodiment, the present invention contemplates that proteolysis is measured by mass spectrometry. In one embodiment, said nucleic is DNA; in another embodiment, it is RNA (e.g. RNA made by in vitro transcription from a PCR product, such as a PCR product amplified from genomic DNA obtained from a whole organism, including humans). In a preferred embodiment, said nucleic acid sequence comprises a portion complementary to a portion of a disease-related gene (e.g. the APC gene).

Regardless of the approach, the present invention contemplates in another embodiment a method, comprising: providing: i) a nucleic acid sequence encoding a polypeptide, said polypeptide being between 10 and 150 amino acids in length (and more preferably between 10 and 100 amino acids in length, and still more preferably between 10 and 80 amino acids in length); and ii) an in vitro translation system that has been treated to reduce protease activity such that a protease-sensitive reference peptide is degraded by less than 50% (and more preferably by less than 30%) by proteolysis following exposure to said translation system for approximately 10 minutes (and more preferably, for 20 minutes) at approximately 37° C.; and introducing said nucleic acid into said translation system under conditions such that said polypeptide is produced. In one embodiment, the present invention contemplates that proteolysis is measured by mass spectrometry. In one embodiment, said nucleic acid is DNA; in another embodiment, it is RNA (e.g. RNA made by in vitro transcription from a PCR product, such as a PCR product amplified from genomic DNA obtained from a whole organism, including humans). In a preferred embodiment, said nucleic acid sequence comprises a portion complementary to a portion of a disease-related gene (e.g. the APC gene).

Regardless of the approach, the present invention contemplates in yet another embodiment a method, comprising: providing a preparation comprising polypeptides, said polypeptides being between 10 and 150 amino acids in length (and more preferrably, between 10 and 100 amino acids in length, and still more preferrably, between 10 and 80 amino acids in length) and comprising a C-terminal epitope; and determining the molecular mass of said polypeptides by mass spectrometry. In a particularly preferred embodiment, said polypeptides further comprise an N-terminal epitope. In a preferred embodiment, said wild type polypeptides were made by in vitro translation (e.g. using a cell-free translation system), and in particular, a translation system that has been treated under conditions such that the protease activity is reduced (e.g. to a level such that there is less than 50% degradation of nascent polypeptides of the stated size range after exposure for 10 minutes at 37 degrees). Moreover, while a variety of proteins can be evaluated in this manner, the present invention contemplates a preferred embodiment wherein at least a portion of each of said polypeptides is identical to a portion of the disease related gene product (e.g. APC gene product).

The mass spectrometry approach is generally applicable and is herein demonstrated for the detection of chain truncation mutations in the APC gene. It is readily applied to the DNA of individuals pre-diagnosed with familial adenomatous polyposis (FAP). This mass spec approach provides a high throughput method for non-invasive colorectal cancer screening. Importantly, there is no need to enrich for low-abundance mutant DNA (although in preferred embodiment, one may enrich for low abundance truncated polypeptides by depleting wild-type sequences).

As embodied and described herein, the present invention comprises methods for the labeling the products of new or nascent protein synthesis, and methods for the isolation of these nascent proteins from preexisting proteins in a cellular or cell-free translation system so that detection can be performed by mass spectrometry.

While the preferred use of the invention is to detect truncation mutations, any proteins that can be expressed by translation in a cellular or cell-free translation system can be evaluated as nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Less than 10 nanoliters of a commercially available *E. coli* extract (*E. coli* T7 translation system, Promega, Madison, Wisc.) are needed for analysis corresponding to less than 1 ng of synthesized protein. Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3, elongation factor T (EF-Tu), or termination factors.

A preferred translation system is a reconstituted system available from Post Genome Institute Co., Ltd. (Japan) called PURESYSTEM. The systems was originally developed at the University of Tokyo and comprises approximately 30 purified enzymes necessary for transcription and translation. Because all the components are tagged with a hexahistidine, the preferred N-terminal and C-terminal epitopes for the wild-type and truncated polypeptides (discussed in various embodiments of the method below) are preferably not Histags. The system is advertised as "essentially free of protease," however, there is significant protease activity that interferes with detection of small polypeptides by mass spectrometry. In one embodiment, the present invention contemplates supplementing a reconstituted system with a protease inhibitor. For example, in one embodiment, the present invention contemplates a cell-free translation system comprising a) ribosomes; b) recombinantly produced proteins, said proteins comprising one or more initiation factors, one or more elongation factors, one or more release factors, a plurality of aminoacyl-tRNA synthetases, and methionyl-tRNA transformylase; and c) one or more protease inhibitors. In one embodiment, said protease inhibitor is aprotinin. In a preferred embodiment, said protease inhibitor is used at a concentration that inhibits proteolysis but does not significantly interfere with translation (e.g. yield of nascent protein is reduced by less than 50% in a 20 minute reaction at 37 degrees, and more preferrably, reduced by less than 30%). In a particularly preferred embodiment, said protease inhibitor is AEBSF.

In one embodiment, the present invention contemplates a cell-free translation system comprising a) ribosomes; b) recombinantly produced proteins, said proteins comprising one or more initiation factors, one or more elongation factors, one or more release factors, a plurality of aminoacyl-tRNA synthetases, and methionyl-tRNA transformylase; and c) a protease-sensitive peptide. In one embodiment, the protease-sensitive peptide is chemically synthesized. However, in another embodiment, the protease-sensitive peptide is made by the translation system. In one embodiment, the present invention contemplates a kit, comprising: a) ribosomes; b) recombinantly produced proteins comprising one or more initiation factors, one or more elongation factors, one or more release factors, a plurality of aminoacyl-tRNA synthetases, and methionyl-tRNA transformylase; and c) a chemically synthesized, protease-sensitive peptide. In another embodiment, the present invention contemplates a kit, comprising: a) ribosomes; b) recombinantly produced proteins comprising one or more initiation factors, one or more elongation factors, one or more release factors, a plurality of aminoacyl-tRNA synthetases, and methionyl-tRNA transformylase; and c) a nucleic acid encoding a protease-sensitive peptide.

In one embodiment, the present invention contemplates a method, comprising: a) providing: i) a nucleic acid sequence encoding a polypeptide, said polypeptide being between 10 and 150 amino acids in length (and more preferably between 10 and 100 amino acids in length, and even more preferably between 10 and 80 amino acids in length); and ii) a reconstituted in vitro translation system comprising recombinant proteins (e.g. purified proteins necessary for in vitro transcription and translation); b) introducing said nucleic acid into said reconstituted translation system under conditions such that said polypeptide is produced; and c) determining the molecular mass of said polypeptide by mass spectrometry. In another embodiment, the present invention contemplates a method, comprising: a) providing: i) a nucleic acid sequence encoding a polypeptide, said polypeptide being between 10 and 150 amino acids in length (and more preferably between 10 and 100 amino acids in length, and even more preferably between 10 and 80 amino acids in length); and ii) a reconstituted in vitro translation system comprising recombinant proteins and isotopically-depleted amino acids; b) introducing said nucleic acid into said reconstituted translation system under conditions such that said polypeptide is produced, said polypeptide comprising isotopically-depleted amino acids; and determining the molecular mass of said polypeptide by mass spectrometry. By "isotopically-depleted" it is not intended that the present invention be limited to complete depletion or completely monoisotopic amino acids. It is enough that there is depletion such that the natural occurrence of isotopes such as $C^{13}$ and $N^{15}$ is reduced. In one embodiment said isotopically-depleted amino acids are $C^{13}$-depleted. In another embodiment, said isotopically-depleted amino acids are $N^{15}$-depleted. In a preferred embodiment said isotopically-depleted amino acids are $C^{13}$- and $N^{15}$-depleted. It is preferred that, with respect to the isotopes of carbon and nitrogen, the amino acids consist primarily of $C^{12}$ and $N^{14}$ (e.g. greater than 99%, and more preferably greater than 99.9%). Media depleted of $C^{13}$ and $N^{15}$ is commercially available from Cambridge Isotope Labs., Inc. under the name "Mono-Express." Such media can be used with bacterial expression systems. The present invention contemplates that this approach will avoid broad peaks, simplify the mass spectrum, and make the mass determination more sensitive and precise.

In one embodiment, said nucleic acid is DNA; in another embodiment, it is RNA (e.g. RNA made by in vitro transcription from a PCR product, such as a PCR product amplified from genomic DNA obtained from a whole organism, including humans). In a preferred embodiment, said nucleic acid sequence comprises a portion complementary to a portion of a disease-related gene (e.g. the APC gene). In one embodiment, the reconstituted translation system has been supplemented with a protease inhibitor. In another embodiment, the reconstituted translation system has been treated to deplete proteases (e.g. by filtering and/or replacing with highly purified ribosomes). In one embodiment, the polypeptide produced has both an N-terminal and C-terminal epitope and is separated (e.g. prior to step c) from said translation system by a ligand to one of the epitopes (or ligands to both epitopes). In a preferred embodiment, the polypeptide is separated by a ligand to the N-terminal epitope.

Regardless of the approach, the present invention contemplates in one embodiment a cell-free translation system comprising a) ribosomes; and b) recombinantly produced proteins, said proteins comprising one or more initiation factors, one or more elongation factors, one or more release factors, a plurality of aminoacyl-tRNA synthetases, and methionyl-tRNA transformylase, wherein said ribosomes and said recombinantly produced proteins in a mixture exhibit protease activity at a level such that a protease-sensitive reference peptide of between 10 and 30 amino acids in length is degraded by less than 50% (and preferably less than 40%, and more preferably less than 30%, and still more preferrably less than 20%) following exposure to said mixture for approximately 20 minutes at approximately 37° C. While desirable, it is not required that all protease activity be eliminated or inhibited.

The present invention further contemplates in one embodiment a cell-free translation system comprising a) a protease inhibitor, b) ribosomes; and c) recombinantly produced proteins, said proteins comprising one or more initiation factors, one or more elongation factors, one or more release factors, a plurality of aminoacyl-tRNA synthetases, and methionyl-tRNA transformylase, wherein said ribosomes and said recombinantly produced proteins in a mixture with said protease inhibitor exhibit protease activity at a level such that a protease-sensitive reference peptide of between 10 and 30 amino acids in length is degraded by less than 50% (and preferably less than 40%, and more preferably less than 30%, and still more preferrably less than 20%) following exposure to said mixture for approximately 20 minutes at approximately 37° C. While desirable, it is not required that all protease activity be eliminated or inhibited.

In one embodiment, the present invention contemplates a method, comprising: a) providing: i) a nucleic acid sequence encoding a protease-sensitive reference polypeptide, said polypeptide being between 5 and 50 amino acids in length (and more preferrably between 10 and 30 amino acids in length, and even more preferably between 15 and 25 amino acids in length); and ii) a reconstituted in vitro translation system comprising recombinant proteins (e.g. purified proteins necessary for in vitro transcription and translation); and b) introducing said nucleic acid into said reconstituted translation system under conditions such that said polypeptide is produced. In a preferred embodiment, the method further comprises c) detecting the polypeptide by mass spectrometry. In a particularly preferred embodiment, the method further comprises c) detecting the proteolytic degradation of said polypeptide by mass spectrometry. In one embodiment, n the protease-sensitive peptide comprises an N-terminal epitope (for convenient capture and purification from the mixture). In a preferred embodiment, the protease-sensitive peptide further comprises a region of positively charged amino acids selected from the group consisting of arginine, lysine or histidine. In a more preferred embodiment, the protease-sensitive peptide further comprises a C-terminal region comprising hydrophobic amino acids (e.g. phenylalanine). Optionally, the N-terminus can have other amino acids (e.g. methionine) or protecting groups (FMOC, etc.). In one embodiment, the protease-sensitive reference polypeptide is selected from the polypeptides set forth in Table 2.

The PURESYSTEM lacks tRNAs to rare codons. In one embodiment, the present invention contemplates supplementing a reconstituted system with tRNAs to rare codons For example, in one embodiment, the present invention contemplates a cell-free translation system comprising a) ribosomes; b) recombinantly produced proteins, said proteins comprising one or more initiation factors, one or more elongation factors, and one or more release factors, a plurality of aminoacyl-tRNA synthetases, and methionyl-tRNA transformylase; and c) a plurality of tRNAs, said tRNAs comprising tRNAs for one or more codons selected from the group consisting of AGG, AGA, AUA, CUA, CCC and GGA. In one embodiment, the present invention contemplates a kit, comprising a) ribosomes; b) recombinantly produced proteins, said proteins comprising one or more initiation factors, one or more elongation factors, one or more release factors, a plurality of aminoacyl-tRNA synthetases, and methionyl-tRNA transformylase; and c) a plurality of tRNAs, said tRNAs comprising tRNAs for one or more codons selected from the group consisting of AGG, AGA, AUA, CUA, CCC and GGA. Such a kit may further comprise instructions for carrying out translation.

Cell-free systems may also be coupled transcription/translation systems wherein DNA is introduced to the system, transcribed into mRNA and the mRNA translated as described in Current Protocols in Molecular Biology (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), can be used but are not required in all embodiments.

Site-directed incorporation of the nonnative analogs into the protein during translation is also not required. Incorporation of markers can occur anywhere in the polypeptide and can also occur at multiple locations. This eliminates the need for prior information about the genetic sequence of the translated mRNA or the need for modifying this genetic sequence.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wisc.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example tRNA$^{fMet}$, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334-338, 1987). Run-off transcription allows for the production of any specific tRNA in high purity, but its applications can be limited due to lack of post-transcriptional modifications (Bruce and Uhlenbeck, Biochemistry 21:3921, 1982).

In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4° C. to −70° C. The method of preparing such reaction mixtures is described by J. M. Pratt (*Transcription and Translation*, B. D. Hames and S. J. Higgins, Editors, p. 209, IRL Press, Oxford, 1984) which is hereby incorporated by reference. Many different translation systems are commercially available from a number of manufacturers.

Translations in cell-free systems generally require incubation of the ingredients for a period of time. Incubation times range from about 5 minutes to many hours, but is preferably between about ten and thirty minutes and more preferably between about ten to twenty minutes. Incubation may also be performed in a continuous manner whereby reagents are flowed into the system and nascent proteins removed or left to accumulate using a continuous flow system (A. S. Spirin et al., Sci. 242:1162-64, 1988). This process may be desirable for large scale production of nascent proteins. Incubations may also be performed using a dialysis system where consumable reagents are available for the translation system in an outer reservoir which is separated from larger components of the translation system by a dialysis membrane [Kim, D., and Choi, C. (1996) *Biotechnol Prog* 12, 645-649]. Incubation times vary significantly with the volume of the translation mix and the temperature of the incubation.

Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. On the other hand, it is possible that mRNA secondary structure interferes with efficient cell-free protein expression yields. While not limiting the present invention to any particular mechanism, it is believed that one approach to this problem is to increase the temperature of the translation reaction from 37° C. to between 39° C. and 45° C. more preferably to approximately 42° C. or 43° C. In another embodiment, components are added that create favorable reaction conditions. For example, in one embodiment, magnesium (e.g. in the form of a salt such as $MgCl_2$) in the millimolar range is added and the conventional temperature of 37° C. is maintained (or the higher preferred temperature of 42-43° C. is used). In another embodiment, betaine (trimethylglycine) is added in the submolar range to the translation mixture and the conventional temperature of 37° C. is maintained (or the higher preferred temperature of 42-43° C. is used). In some embodiments, the temperature is not constant throughout the time period of the reaction. In other embodiments, the temperature is maintained within 1 degree throughout the time period of the reaction.

It is not intended that the present invention be limited only to the addition of betaine. In some embodiments, the present invention contemplates improving the in vitro nucleic acid conformation and stability with buffer solutions containing any of a number of natural and synthetic osmoprotectant compounds, including polysaccharides such as trehalose (Caminci, P., et al., Proc. Natl. Acad Sci. USA 95:520-524 (1998)), certain co-solvents such as glycerol and dimethylsulfoxide (Varadaraj, K., and Skinner, D. M., Gene 140:1 (1994)); glycine and derivatives thereof (Buche, A., et al., FEBS Lett. 247(2):367 (1989); low molecular weight amines such as beta-alanine, asparagine and cystamine (Kondakova, N. V., et al., Mol. Biol. (Moscow) 9(5):742 (1975), Aslanian, V. M., et al., Biofizika 29(4)564 (1984)); and other nitrogen-containing compounds and amino acids such as proline and ectoine (Rees, W. A., et al., Biochemistry 32:137-144 (1993); Henke, W., et al., Nucl. Acids Res. 25(19):3957 (1997)).

In the context of the present invention, preferred embodiments utilize these additives in concentrations that do not significantly interfere with the transcription/translation reaction. For example, in preferred embodiments, betaine is used in concentrations between 10 and 100 mM. In preferred embodiments, glycerol is used in concentrations between 0.08% and 1.6%. In preferred embodiments, DMSO is used between 0.1% and 1%.

Other approaches to secondary structure involve changes in primer design. In one embodiment, silent substitutions in the 5' and/or 3' primers are made in order to avoid undesirable base paring. In one embodiment, forward primers contained several different nucleotides both in the 5'-UTR and in the FLAG tag sequence immediately downstream of the initiation codon. In another embodiment, only the 5'-UTR nucleotides are changed. In another embodiment, only the codons encoding the FLAG epitope are optimized. Regardless of where the substitutions are placed, the present invention contemplates using codon degeneracy so that the resulting amino acid sequence is not changed. Importantly, the above-described changes can be combined with other approaches to avoiding secondary structure. For example, the primer design approach can be combined with the higher temperature embodiments (e.g. 42-43° C.) discussed above.

The present invention also contemplates, in one embodiment, another change in primer design. In order to increase the sensitivity of the mass spec assay to detect small levels of chain truncating mutants, a WT translation suppression assay was developed. While not limiting the present invention to any particular mechanism, it is believed that this approach involves enriching the mutant fraction by (at least partially) arresting the full-length mRNA/polypeptides on the ribosomes during the translation. In one embodiment, arrest of most of the full-length polypeptide on ribosome is achieved using the amplicons without the stop codon at 3'-end. In other words, in one embodiment, the 3'-primer is designed without a stop codon at the end. Thus, any of the 3'-primers described herein can optionally lack the stop codon that is shown.

Translation mixes will typically comprise buffers such as Tris-HCl, Hepes or another suitable buffering agent to maintain the pH of the solution between about 6 to 8, and preferably at about 7. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In one embodiment, the present invention contemplates the filtration of the translation mix (after translation but prior to purification, e.g. purification using the epitope such as FLAG), which presumably removes the ribosome fraction, thereby significantly improving (i.e. reducing) the background. While not intending to limit the invention to any particular mechanism, it is believed that these background peaks are due to incomplete translation products since these peptides remain bound to the ribosomes. It is not intended that the present invention be limited to the precise filtering approach. However, it is convenient to use membrane filters with a particular size cut-off, e.g. YM-100 membrane filters (Millipore, Mass.).

In cellular protein synthesis, it is necessary to introduce RNA or DNA into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner et al., Proc. Natl. Acad. Sci. USA 84:7413-17, 1987), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, preferably between about 0.1 nM to about 0.01 mM, and more preferably about 1 nM. Permeabilized cells allow markers to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker, could be introduced to cells and incorporated into translated products.

It will be understood by those skilled in the area of molecular biology and biochemistry that the N-terminal marker, affinity marker and C-terminal marker can all consist of epitopes that can be incorporated into the nascent protein by designing the message or DNA coding for the nascent protein to have a nucleic acid sequence corresponding to the particular epitope. This can be accomplished using known methods such as the design of primers that incorporate the desired nucleic acid sequence into the DNA coding for the nascent protein using the polymerase chain reaction (PCR).

For optimal effectiveness, the N-terminal marker and affinity marker should be placed as close as possible to the N-terminal end of the protein. For example, if an N-terminal marker is incorporated using a misaminoacylated initiator, it will be located at the N-terminal amino acid. In this case, the affinity marker should be located immediately adjacent to the N-terminal marker. For optimal effectiveness, the C-terminal marker should be placed as close as possible to the C-terminal end of protein. For example, if a His-x6 tag is utilized, the protein sequence would terminate with 6 His. In some cases, an epitope may be located several residues before the C-terminal end of the protein in order to optimize the properties of the nascent protein. This might occur for example, if a specific amino acid sequence is necessary in order to modify specific properties of the nascent protein that are desirable such as its solubility, hydrophobicity and ability to ionize.

There are several unique advantages of this method compared to existing techniques for detecting chain terminating or out-of-frame mutations. Normally, such mutations are detected by analyzing the entire sequence of the suspect gene using conventional DNA sequencing methods. However, such methods are time consuming, expensive and not suitable for rapid throughput assays of large number of samples. An alternative method is to utilize mass spec, which is able to detect changes from the expected size of a nascent protein.

Detecting a protein with an epitope located near the C-terminal end of the protein provides information about the presence of either a frameshift or chain terminating mutation since the presence of either would result in an incorrect sequence. The measurement of the N-terminal marker provides an internal control to which measurement of the C-terminal marker can be normalized. Separating the protein from the translation mixture using an affinity marker located at or close to the N-terminal end of the protein eliminates the occurrence of false starts which can occur when the protein is initiated during translation from an internal AUG in the coding region of the message. A false start can lead to erroneous results since it can occurs after the chain terminating or out-of-frame mutation. This is especially true if the internal AUG is in-frame with the message. In this case, the peptide C-terminal marker will still be present even if message contains a mutation.

DETAILED DESCRIPTION

Mass spectrometry measures the mass of a molecule. The use of mass spectrometry in biology is continuing to advance rapidly, finding applications in diverse areas including the analysis of carbohydrates, proteins, nucleic acids and biomolecular complexes. For example, the development of matrix assisted laser desorption ionization (MALDI) mass spectrometry (MS) has provided an important tool for the analysis of biomolecules, including proteins, oligonucleotides, and oligosacharrides. Thus far, it has been found applicable in diverse areas of biology and medicine including the rapid sequencing of DNA, screening for bioactive peptides and analysis of membrane proteins.

Markers introduced into nascent proteins, especially at a specific position such at the N-terminal, can be used to isolate the protein prior to the detection by mass spectrometry. Without such a marker, it can be very difficult to detect a peak because a nascent protein synthesized in the presence of a cellular or cell-free extract is in the presence of many other molecules of similar mass in the extract. For example, in some cases less than 0.01% of the total protein mass of the extract may comprise the nascent protein(s). Furthermore, molecules with similar molecular weight as the nascent protein may be present in the mixture. Such molecules will overlap with peaks due to the nascent protein. This problem is particularly severe if the nascent protein is a transcription or translation factor already present in the cell-free or cellular protein synthesis. The synthesis of additional amounts of this protein in the protein synthesis system would be difficult to detect using known methods in mass spectrometry since peak intensities are not correlated in a linear manner with protein concentration.

The sensitivity of mass spec creates unique issues. While the protease concentration in commercially available translation systems may not be problematic for some applications, the presence of protease in the context of mass spectrometry can completely obscure detection. Consequently, preferred embodiments of the invention employ means to reduce and/or eliminate proteolysis of in vitro (cell-free) expressed proteins and protein fragments which are used specifically for diagnostic purposes such as described herein. These means can include but are not limited to the addition of compounds to the in vitro protein expression system which inhibit the proteolytic processes, the elimination of factors from the mixture which are involved in proteolysis, the inactivation of factors through physical means including heating, light and physical binding to other molecules, the design of expressed polypeptide sequences which are resistant to proteolysis and the incorporation into the polypeptide of non-native amino acids which increase resistance to proteolysis including modifications on the N-terminal and C-terminal end of the polypeptide.

Although, up to now the role that proteolysis may play in using in vitro expressed proteins for diagnostic purposes has not been emphasized, we have performed experiments that demonstrate that such proteolytic processes can hinder the use of in vitro expressed proteins and protein fragments for such purposes. For example, many of the methods described herein involve the in vitro expression of a protein or protein fragment from a DNA or mRNA template followed by its isolation and/or detection using specific epitopes which are recognized by specific antibodies or by the incorporation of non-native amino acids through the use of mis-aminoacylated tRNAs that subsequently react with a binding molecule such as a combination of biotin and streptavidin. In all of the above cases, proteolysis of the protein or protein fragment can interfere with isolation and/or detection steps.

DESCRIPTION OF PREFERRED EMBODIMENTS

Colorectal Cancer Detection

The present invention contemplates the isolation, detection and identification of expressed proteins having an altered primary amino acid sequence. One example of an altered primary sequence is a protein chain truncation. A protein chain truncation is most easily explained by a frameshift mutation that generates a stop codon (i.e., AUG) within the open reading frame. The resulting translation of the MRNA from this mutated gene synthesizes a nonfunctional or malfunctional protein. One example of such a truncated protein is derived from the APC gene, and is known to be a diagnostic marker for colorectal cancer.

Many attempts have been reported to detect and analyze biological samples using a noninvasive diagnostic marker of colorectal cancer. Currently, the most reliable method to identify and treat colorectal cancer requires a colonoscopy. While colonoscopy is not a high risk procedure, except for the associated general anesthesia, it is expensive and there is a serious problem regarding obtaining compliance for one time or repeated testing due to the invasive nature of the examination and the extensive bowel preparation required. One possible non-invasive source of diagnostic markers is fecal matter.

The Protein Truncation Test (PTT) was first reported by Roest et al., *Protein Truncation Test (PTT) For Rapid Detection Of Translation-Terminating Mutations*. Hum Mol Genet 2:1719-1721 (1993), and applied to the detection of truncating mutations in the APC gene by Powell et al., *Molecular Diagnosis Of Familial Adenomatous Polyposis*. N. Engl J Med 329:1982-1987 (1993). In traditional PTT, the region of the gene to be analyzed is amplified by PCR (or RT-PCR for an mRNA template) using a primer pair that incorporates additional sequences into the PCR amplicons required for efficient cell-free translation. The amplified DNA is then added to a cell-free transcription-translation extract along with radioactive amino acids ($^{35}$S-methionine or $^{14}$C-leucine). The expressed protein is analyzed by SDS-PAGE and autoradiography. Chain truncation mutations are detected by the presence of a lower molecular weight (increased mobility) species relative to the wild-type (WT) protein band. Non-radioactive Western blot-based PTT-methods utilizing a combination of N-terminal and C-terminal epitopes have also been reported. Rowan et al., *Introduction Of A myc Reporter Tag To Improve The Quality Of Mutation Detection Using The*

*Protein Truncation Test.* Hum Mutat 9:172-176 (1997); de Koning Gans et al., *A Protein Truncation Test For Emery-Dreifuss Muscular Dystrophy (EMU): Detection Of N-Terminal Truncating Mutations.* Neuromuscul Disord 9:247-250 (1999); and Kahamnn et al., *A Non-Radioactive Protein Truncation Test For The Sensitive Detection Of All Stop And Frameshift Mutations.* Hum Mutat 19:165-172 (2002). However, these approaches still involve lengthy steps of SDS-PAGE, electroblotting and membrane-based immunoassay.

As an alternative to SDS-PAGE based PTT, the present invention contemplates a high throughput mass spec approach. Amplified DNA corresponding to the region of interest in the target gene is first generated using PCR with primers that incorporate, in one embodiment, N- and C-terminal epitope tags as well as a T7 promoter, Kozak sequence and start codon (ATG) in the amplicons. The resulting amplified DNA is subsequently added to a cell-free protein expression system (preferably a reconstituted system, including but not limited to a reconstituted system that has been further treated or modified to reduce protease activity). The N-terminal epitope is used to capture the translated protein from the cell-free expression mixture onto a solid surface. The C-terminal epitope tag can be used to deplete wild-type sequences.

As an initial evaluation, this mass spec approach was used to detect truncating mutations in a region of the APC gene (segment 3; amino acids 1098-1696) using genomic DNA as a PCR template. While various epitope tag sequences including His-6, c-myc, P53 (derived from the P53 sequence), VSV-G, Fil-16 (filamin derived) and StrepTag can be used, FLAG and HA were chosen (in one embodiment) as the N- and C-terminal epitopes, respectively. In order to enhance throughput, the nascent fragment of APC segment 3 was selectively captured from the reaction mixture via the N-terminal tag, thereby conveniently separating the nascent protein from the translation system. To enhance sensitivity, wild-type sequences with a C-terminal epitope can be depleted (prior to mass spec) by exposure to a ligand having affinity for the C-terminal epitope.

DNA derived from patients with familial adenomatous polyposis (FAP) as well as cell-line DNA with known mutations in segment 3 can be analyzed.

While heterozygous mutations in germ-line cells are expected to comprise 50% of the total DNA in a sample, sporadic mutations are often present in significantly lower abundance, such as the case of stool samples from individuals with colorectal cancer. Traverso et al., *Detection Of APC Mutations In Fecal DNA From Patients With Colorectal Tumors.* N Engl J. Med 346:311-320 (2002); Deuter et al., *Detection Of APC Mutations In Stool DNA Of Patients With Colorectal Cancer By HD-PCR.* Hum Mutat, 11:84-89 (1998); and Doolittle et al., *Detection Of The Mutated K-Ras Biomarker In Colorectal Carcinoma.* Exp Mol Pathol 70:289-301 (2001). One approach, termed digital PTT, has been utilized to overcome this problem. However, the mass spec approach described here does not require such serial dilution of DNA prior to PCR amplification.

Using the mass spectrometry approach described herein, detection of a mutation can be made wherein the mutated copies of the gene are present in a ratio of 1:250 (vis-à-vis the wild type sequences). At the polypeptide level, detection of a truncated polypeptide can be made in a ratio of 1:100 (but more routinely in a ratio of 1:50, as still more routinely in a ration of 1:10, vis-à-vis the wild type polypeptide).

The present invention contemplates the isolation, detection and identification of mutated genes by methods that do not require extensive and expensive purification, isolation and sequencing procedures. Furthermore, the present invention contemplates the use of nucleic acid material from any tissue or fluid sample, and is not restricted to fecal samples. Specifically, sample DNA from a patient suspected of having cancer is amplified by PCR using primers comprising sequences encoding a N-terminal and C-terminal epitope. The epitope-containing sample DNA is placed in a translation system (i.e., resulting in the production of mRNA followed by protein synthesis).

EXPERIMENTAL

The following examples illustrate embodiments of the invention, but should not be viewed as limiting the scope of the invention. In some of the examples below, particular reagents and methods were employed as follows:

Reagents: tRNA$^{fmet}$, aminoacyl-tRNA synthetase, amino acids, buffer salts, and RNase free water were purchased from Sigma (St. Louis, Mo.). Many of the fluorescent dyes were obtained from Molecular Probes (Eugene, Oreg.). The translation supplies including routine kits were purchased from Promega (Madison, Wis.). Sephadex G-25 was from Amersham-Pharmacia Biotech (Piscataway, N.J.). The in vitro translation kits and plasmid DNAs coding for CAT (PinPoint™) and Luciferase (pBESTluc™) were from Promega (Wisconsin-Madison, Wis.) while DHFR plasmid DNA (pQE16-DHFR) was obtained from Qiagen (Valencia, Calif.). The plasmid DNA for alpha-hemolysin, pT7-WT-H6-HL was kindly supplied by Prof. Hagan Bayley (Texas A&M University) and large scale preparation of alpha-HL DNA was carried out using Qiagen plasmid isolation kit. The bacterioopsin plasmid DNA (pKKbop) was from the laboratory stock.

Preparation of FluoroTag tRNAs: The purified tRNA$^{fmet}$ was first aminoacylated with the methionine. In a typical reaction, 1500 picomoles (~1.0 OD$_{260}$) of tRNA were incubated for 45 mm at 37° C. in aminoacylation mix using an excess of aminoacyl tRNA-synthetases. After incubation, the mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μL). The coupling of NHS-derivatives of fluorescent molecules to the alpha-amino group of methionine was carried out in 50 mM sodium carbonate, pH 8.5 by incubating the aminoacylated tRNA$^{met}$ (25 μL) with fluorescent reagent (final concentration=2 mM) for 10 mm at 0° C. and the reaction was quenched by the addition of lysine (final concentration=100 mM). The modified tRNA was precipitated with ethanol and passed through a Sephadex G-25 gel filtration column (0.5×5 cm) to remove any free fluorescent reagent, if present. The modified tRNA was stored frozen (–70° C.) in small aliquots in order to avoid free-thaws. The modification extent of the aminoacylated-tRNA was assessed by acid-urea gel electrophoresis. This tRNA was found to be stable for at least 6 months if stored properly.

Cell free synthesis of proteins and their detection: The in vitro translation reactions were typically carried out using *E. coli* T7 transcription-translation system (Promega) with optimized premix. The typical translation reaction mixture (10 μl) contained 3 μL of extract, 4 μL of premix, 1 μL of complete amino acid mix, 30 picomoles of fluorescent-methionyl-tRNA and 0.5 μg of appropriate plasmid DNA. The optimized premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. The translation reaction was allowed to proceed for 45 mm at 37° C. For SDS-PAGE, a 4-10 μL aliquot of the reaction mix was precipitated with 5-volume acetone and the precipitated proteins were collected by centrifugation. The pellet was dissolved in 1× loading buffer and subjected to SDS-PAGE after boiling for 5 mm SDS-PAGE was carried out according to Laemmli and the gel was scanned using a Molecular Dynamics FluorImager 595 using argon as the excitation source. Alternatively, the nascent proteins in polyacrylamide gels were also detected using an UV-transilluminator and the photographs were carried out using a Polaroid camera fitted with a green filter (Tiffen green #58, Polaroid DS34 Camera filter kit).

For visualization of BODIPY-FL labeled protein, 488 nm as excitation source was used along with a 530+/−30 narrow band excitation filter. The gel was scanned using PMT voltage 1000 volts and either 100 or 200 micron pixel size.

Enzyme/Protein activities: Biological activity of alpha-hemolysin was carried out as follows. Briefly, various aliquots (0.5-2 ul) of in vitro translation reaction mixture were added to 500 ul of TBSA (Tris-buffered saline containing 1 mg/ml BSA, pH 7.5). To this, 25 ul of 10% solution of rabbit red blood cells (rRBCs) was added and incubated at room temperature for 20 min. After incubation, the assay mix was centrifuged for 1 min and the absorbance of supernatant was measured at 415 nm (release of hemoglobin). The equal amount of rRBCs incubated in 500 ul of TBSA is taken as control while rRBCs incubated with 500 ul of water as taken 100% lysis. The DHFR activity was measured spectrophotometrically. Luciferase activity was determined using luciferase assay system (Promega) and luminescence was measures using Packard Lumi-96 luminometer.

Purification of Alpha-HL and Measurement BODIPY-FL Incorporation into Alpha-HL:

The translation of plasmid coding for alpha-HL ($His_6$) was carried out at 100 ul scale and the alpha-HL produced was purified using Talon-Sepharose (ClonTech) according manufacturer instructions. The fluorescence incorporated into alpha-HL was then measured on Molecular Dynamics FluorImager along with the several known concentration of free BODIPY-FL (used as standard). The amount of protein in the same sample was measured using a standard Bradford assay using Pierce Protein Assay kit (Pierce, Rockford, Ill.).

FLAG Capture Assay

Biotinylation of FLAG Antibody

A 4.4 mg/mL stock of FLAG M2 monoclonal antibody (SIGMA Chemical, St. Louis, Mo.) is diluted with equal volume of 100 mM sodium bicarbonate (~15 mM final antibody concentration). Subsequently, NHS-LC-Biotin (Pierce Chemical, Rockford, Ill.) is added from a 2 mM stock (in DMF) to a final 150 mM. The reaction is incubated for 2 hours on ice. The mixture is then clarified by centrifugation in a microcentrifuge (14,000 R.P.M.) for 2.5 minutes. Unreacted labeling reagent is removed by gel filtration chromatography.

Preparation of FLAG Antibody Coated ELISA Plates

NeutrAvidin™ biotin binding protein (Pierce Chemical, Rockford, Ill.) is diluted to a final concentration of 50 mg/mL in 100 mM sodium bicarbonate and used to coat Microlite (2+ white opaque 96-well ELISA plates (Dynex Technologies, Chantilly, Va.). Plates are washed with TBS-T and coated using a solution of 5 mg/mL biotinylated FLAG M2 antibody in TBS-T. Plates are washed with TBS-T and blocked in Translation Dilution Buffer (TDB) [4.5% Teleostean Gelatin, 2% non-fat milk powder, 10 mM EDTA, 0.1% Tween-20, 1.25 mg/mL pre-immune mouse IgG, 2.5 mM d-biotin, in TBS, pH 7.5.].

Binding and Detection of Target Protein

Triple-epitope-tagged target proteins produced by in vitro translation using rabbit reticulocyte extract are diluted 1/25-1/75 in TDB and added to the antibody coated ELISA plates. Following capture of the target protein, plates are washed with TBS-T. Detection of c-myc is performed using a polyclonal antibody (Santa Cruz Biotechnology, Santa Cruz, Calif.) followed by a peroxidase labeled secondary antibody, whereas detection of the $His_6$ tag is achieved with a peroxidase labeled nickel chelate-based probe (India (His Probe-HRP, Pierce, Rockford, Ill.). Antibodies are diluted in TDB and the India (His Probe-HRP is diluted in TBS-T supplemented with 5 mg/mL pre-immune mouse IgG. In all cases, signal is generated using a chemiluminescent substrate system.

His-Tag Metal Affinity Capture ELISA Assay

Binding and Detection of Target Protein

Triple-epitope-tagged target proteins produced by in vitro translation using rabbit reticulocyte extract are diluted 1/25-1/75 in 1% BSA/TBS-T and added to nickel chelate coated ELISA plates (Pierce Chemical, Rockford, Ill.). Following capture of the target protein, plates are washed with TBS-T and blocked with 1% BSA/TBS-T. Detection of epitope tags on the bound target protein is achieved using a monoclonal FLAG M2 antibody (SIGMA Chemical, St. Louis, Mo.) or a polyclonal c-myc antibody (Santa Cruz Biotechnology, Santa Cruz, Calif.) in conjunction with the appropriate peroxidase labeled secondary antibody. Detection of biotin incorporated into the target protein via Biotin-lysyl-tRNA$^{lys}$ is achieved using NeutrAvidin™ biotin binding protein conjugated to peroxidase (Pierce Chemical, Rockford, Ill.). The NeutrAvidin™ conjugate and all antibodies are diluted in 1% BSA/TBS-T. In all cases, signal is generated using a chemiluminescent substrate system.

Mass Spectrometry-Based Protease Assay 100 picomoles of the synthetic R6 peptide in 1 microliter of water is added to 5 ul of a test solution and incubated for 20 minutes (or 10 minutes) at 37 degrees. 50 ul of PBS is then added to the test mixture and the resulting solution is passed over a 1 microliter anti-FLAG microcolumn (which recognizes the epitope sequence at the N terminus of the R6 peptide). The column is washed with 50 ul of deionized water and the bound peptides are eluted directly onto the maldi plate using 1 microliter of CHCA matrix in 50% acetonitrile/0.2% TFA/49.8% deionized water. The intact R6 peptide and degradation products are detected by Maldi-Tof mass spectrometry in positive ion linear mode.

Sample Preparation

Many methods using fecal DNA analysis are based on a home collection device such as a toilet insert which allows an entire stool or portion of stool to be obtained without addition of buffers or other preservatives (whole stool method). Although this approach is compatible with a MASSIVE-PRO CRC assay, we have experimented with a second novel approach which is similar to the "slide" method of collection normally employed to obtain FOBT samples at home for standard laboratory analysis. One advantage of such an approach is that several million FOBT assays are already performed each year and are well accepted both by patients and the medical community. For example, the use of slides greatly simplifies the sending of the sample to a central testing laboratory. In contrast, the Pre-Gen plus test requires whole stool samples to be collected, packaged at home and then shipped in a large box with a cooling insert. Finally, the use of standard FOBT slides opens the possibility of performing both a molecular DNA analysis and FOBT test simultaneously on the same home-collected sample, an approach which is likely to raise the overall sensitivity of the CRC assay.

A key question is whether the small samples collected using FOBT slides is sufficient to perform molecular analysis by MASSIVE-PRO. The first step for processing a stool sample is the isolation of the fecal DNA. In preliminary experiments, we have isolated DNA from various amount of stool ranging from 5-200 mg using the QIAamp DNA Stool Mini Kit (Qiagen, Valencia, Calif.) in order to determine minimum quantity that can be processed and utilized for subsequent amplification of specific regions of the APC gene. The isolated DNA was then analyzed on an agarose gel (not shown), where high molecular weight bacterial DNA and human DNA are separated. The DNA obtained was then quantitated using Molecular Probes PicoGreen DNA quantitation kit (Molecular Probes, Eugene, Oreg.). The results (not shown) indicate that detectable levels of DNA can be easily isolated by this method even when the starting material is 5 mg of stool. The quantitation of total DNA for 5-200 mg stool ranged from 400 ng to 24 μg on a linear scale (not shown).

The isolated fecal DNA was then subjected to PCR analysis using various primer sets including primers which spanned 200 bases of specific segments the APC gene. The results show that an APC segment of approximately 200 bases can be successfully PCR amplified using these test primers even for the lowest amount (5 mg) of stool tested. In addition, we have also used primer pairs which would result in larger PCR amplicons (e.g. 400 base pairs and 600 base pairs) using these DNA samples. The authenticity of APC PCR amplicons obtained is verified using hybridization based probe assays like Invader.

In a second experiment, PCR amplification was performed to see if from stool samples collected using a standard FOBT kit produce amplicons. A small amount of stool sample was smeared on two standard FOBT slides (Hemoccult or Hemoccult SENSA, Beckman Coulter, Fullerton, Calif.) using the provided applicator stick. Note that these slides consist of a type of Guianiac coating which is used solely for the purpose of the FOBT measurement. The quantity of stool sample deposited was found to vary between 1-3 mg. Immediately after collection FOBT slides were sealed using the attached match book covers and placed in an envelope which was stored in a laminar hood at room temperature until further use. Generally, the storage period ranged from 1-4 days. Just prior to DNA isolation, the FOBT slides were cut from the FOBT holder and placed into a 2.0 mL eppendorf tube. To this tube, 1.6 mL of ASL Buffer (QiaAmp kit) was added and the slide insert soaked for 20-30 minutes. The tube was mixed by vortexing to dislodge sample from slide paper. Stool DNA isolation was then performed using the QIAamp DNA Stool Mini Kit. The quantitation of total DNA isolated from FOBT strips ranged from 100-200 ng. When the DNA isolated from FOBT strips is subjected to PCR using APC gene specific primers, a PCR product corresponding to 200 base pairs of APC gene is clearly seen (not shown). These results indicate that the DNA isolated using very small fecal samples or even the FOBT strip smears yield enough DNA for downstream PCR application which is primary step in MASSIVE-PRO assay. These results clearly indicate the feasibility of using FOBT strips for sample collection. Also, we have also used the standard microscope glass slide for sample collection purpose and similar results were obtained (Data not shown). In addition, studies were also carryout using the STAR buffer developed by Roche Applied Sciences which is used to stabilize the stool nucleic acid material during the transport of the sample.

Example 1

Protecting Groups

As discussed above, the present invention contemplates protease-sensitive peptides in order to monitor for complicating protease activity. In some embodiments, the peptide contains a protecting group on the N-terminus, in order to restrict exodigestion to the C-terminus. A variety of protecting groups can be used. In this example, Fmoc is attached to a modified amino acid. Coumarin amino acid (1.14 mmol) was reacted with Fluorenylmethyloxycarbonyl N-hydroxysuccininmidyl ester (Fmoc-NHS ester) 1.08 mmol) in the presence of 1.14 mmol of triethylamine for 30 minutes at room temperature. The reaction mixture was acidified and the precipitate washed with 1 N HCl and dried.

Example 2

Preparation of Extract and Template

Preparation of extract: Wheat germ embryo extract was prepared by floatation of wheat germs to enrich for embryos using a mixture of cyclohexane and carbon tetrachloride (1:6), followed by drying overnight (about 14 hours). Floated wheat germ embryos (5 g) were ground in a mortar with 5 grams of powdered glass to obtain a fine powder. Extraction medium (Buffer I: 10 mM trisacetate buffer, pH 7.6, 1 nM magnesium acetate, 90 mM potassium acetate, and 1 mM DTT) was added to small portions until a smooth paste was obtained. The homogenate containing disrupted embryos and 25 ml of extraction medium was centrifuged twice at 23,000× g. The extract was applied to a Sephadex G-25 fine column and eluted in Buffer II (10 mM trisacetate buffer, pH 7.6, 3 mM magnesium acetate, 50 mM potassium acetate, and 1 mM DTT). A bright yellow band migrating in void volume and was collected (S-23) as one ml fractions which were frozen in liquid nitrogen.

Preparation of template: Template DNA was prepared by linearizing plasmid pSP72-bop with EcoRI. Restricted linear template DNA was purified by phenol extraction and DNA precipitation. Large scale mRNA synthesis was carried out by in vitro transcription using the SP6-ribomax system (Promega; Madison, Wis.). Purified mRNA was denatured at 67° C. for 10 minutes immediately prior to use.

Example 3

Cell-Free Translation Reactions

The incorporation mixture (100 μL) contained 50 μl of S-23 extract, 5 mM magnesium acetate, 5 mM Tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 μg /ml creatine kinase, and 100 μg /ml mRNA containing the genetic sequence which codes for bacterioopsin. Misaminoacylated PCB-lysine or coumarin amino acid-tRNA$^{lys}$ molecules were added at 170 μg /ml and concentrations of magnesium ions and ATP were optimized. The mixture was incubated at 25° C. for one hour.

Example 4

Isolation of Nascent Proteins Containing PCB-Lysine

Streptavidin coated magnetic Dynabeads M-280 (Dynal; Oslo, Norway), having a binding capacity of 10 ug of biotinylated protein per mg of bead. Beads at concentrations of 2 mg/ml, were washed at least 3 times to remove stabilizing BSA. The translation mixture containing PCB-lysine incorporated into nascent protein was mixed with streptavidin coated beads and incubated at room temperature for 30 minutes. A magnetic field was applied using a magnetic particle concentrator (MPC)(Dynal; Oslo, Norway) for 0.5-1.0 minute and the supernatant removed with pipettes. The reaction mixture was washed 3 times and the magnetic beads suspended in 50 ul of water.

Photolysis was carried out in a quartz cuvette using a Black-Ray longwave UV lamp, Model B-100 (UV Products, Inc.; San Gabriel, Calif.). The emission peak intensity was approximately 1100 uW/cm$^2$ at 365 nm. Magnetic capture was repeated to remove the beads. Nascent proteins obtained were quantitated and yields estimated at 70-95%.

Example 5

One Triple Marker Embodiment

In this example, a three marker system is employed to detect nascent proteins, i.e. an N-terminus marker, a C-terminus marker, and an affinity marker (the latter being an endogenous affinity marker). The experiment involves 1) preparation of a tRNA with a marker, so that a marker can be introduced (during translation) at the N-terminus of the protein; 2) translation of hemolysin with nucleic acid coding for wild type and mutant hemolysin; and 4) quantitation of the markers.

1. Preparation of Biotin-Methionyl-tRNA$^{fmet}$

The purified tRNA$^{fmet}$ (Sigma Chemicals, St. Louis, Mo.) was first aminoacylated with methionine. The typical aminoacylation reaction contained 1500 picomoles (~1.0 OD$_{260}$) of tRNA, 20 mM imidazole-HCl buffer, pH 7.5, 10 mM MgCl$_2$, 1 mM methionine, 2 mM ATP, 150 mM NaCl and excess of aminoacyl tRNA-synth-etases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 ul). The coupling of NHS-biotin to the _-amino group of methionine was carried out in 50 mM sodium bicarbonate buffer, pH 8.0 by incubating the aminoacylated tRNA$^{fmet}$ (25 ul) with NHS-biotin (final concentration=2 mM) for 10 min at 0° C. and the reaction was quenched by the addition of free lysine (final concentration=100 mM). The modified tRNA was precipitated with ethanol and passed through Sephadex G-25 gel filtration column (0.5×5 cm) to remove any free reagent, if present.

2. In Vitro Translation of Alpha-HL DNA

A WT and Amber (at position 135) mutant plasmid DNA was using coding for alpha-hemolysin (alpha-HL), a 32 kDa protein bearing amino acid sequence His-His-His-His-His-His (His-6) (SEQ ID NO: 120) at its C-terminal. In vitro translation of WT and amber mutant alpha-HL gene (Amb 135) was carried out using *E. coli* T7 circular transcription/translation system (Promega Corp., Wisconsin, WI) in presence of Biotin-methionyl-tRNA$^{fmet}$ (AmberGen, Inc.). The translation reaction of 100 ul contained 30 ul *E. coli* extract (Promega Corp., Wisconsin, WI), 40 ul premix without amino acids, 10 ul amino acid mixture (1 mM), 5 ug of plasmid DNA coding for WT and mutant alpha-HL, 150 picomoles of biotin-methionyl-tRNA$^{fmet}$ and RNase-free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control. After the translation reaction mixture was diluted with equal volume of TBS (Tris-buffered saline, pH 7.5). Each sample was divided into two aliquots and processed individually as described below.

3. Preparation of Anti-Alpha-HL Antibody Microtiter Plate

Anti-rabbit-IgG coated microtiter plate (Pierce Chemicals, Rockford, Ill.) was washed with Superblock buffer solution (Pierce) and incubated with 100 ug/ml of anti-alpha-HL polyclonal antibody solution (Sigma Chemicals, St. Louis, Mo.) prepared in Superblock buffer on microtiter plate shaker for 1 hour at room temperature. The plate was then washed (3 times×200 ul) with Superblock buffer and stored at 4° C. till further use.

4. Quantitation of N-Terminal (Biotin) Marker

The translation reaction mixture (50 ul) for the control, WT and amber alpha-HL DNA were incubated in different wells of anti-alpha-HL microtiter plate for 30 minutes on the shaker at room temperature. After incubation, the wells were washed 5 times (5-10 min each) with 200 ul Superblock buffer and the supernatant were discarded. To these wells, 100 ul of 1:1000 diluted streptavidin-horse radish peroxidase (Streptavidin-HRP; 0.25 mg/ml; Promega) was added and the plate was incubated at room temperature for 20 min under shaking conditions. After the incubation, excess streptavidin-HRP was removed by extensive washing with Superblock buffer (5 times×5 min each). Finally, 200 ul of substrate for HRP (OPD in HRP buffer; Pierce) was added and the HRP activity was determined using spectrophotometer by measuring absorbance at 441 nm.

5. Quantitation of C-Terminal (His-6-taq) Marker

Translation reaction mixture (50 ull) from example 2 for control, WT and Amber alpha-HL DNA were incubated in different wells of anti-alpha-HL microtiter plate for 30 min on the shaker at room temperature. After incubation, the wells were washed 5 times (5-10 min each) with 200 ul Superblock buffer and the supernatant were discarded. To these wells, 100 ul of 1:1000 diluted anti-His-6 antibody (ClonTech, Palo Alto, Calif.) was added to the well and incubated at room temperature for 20 min under shaking conditions. After the incubation, excess antibodies were removed with extensive washing with Superblock buffer (5 times×5 min each). Subsequently, the wells were incubated with secondary antibody (anti-mouse IgG-HRP, Roche-BM, Indianapolis, Ind.) for 20 min at room temperature. After washing excess 2$^{nd}$ antibodies, HRP activity was determined as described above.

6. Gel-Free Quantitation of N- and C-Terminal Markers

Figure 1A:
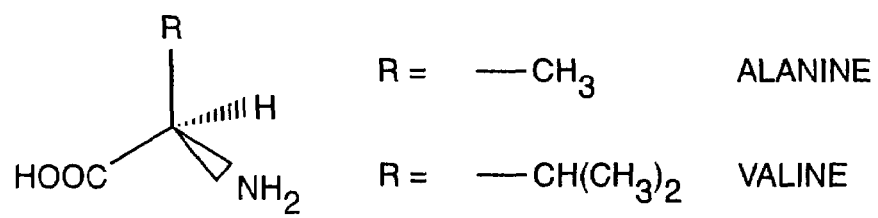
Figure 1B:
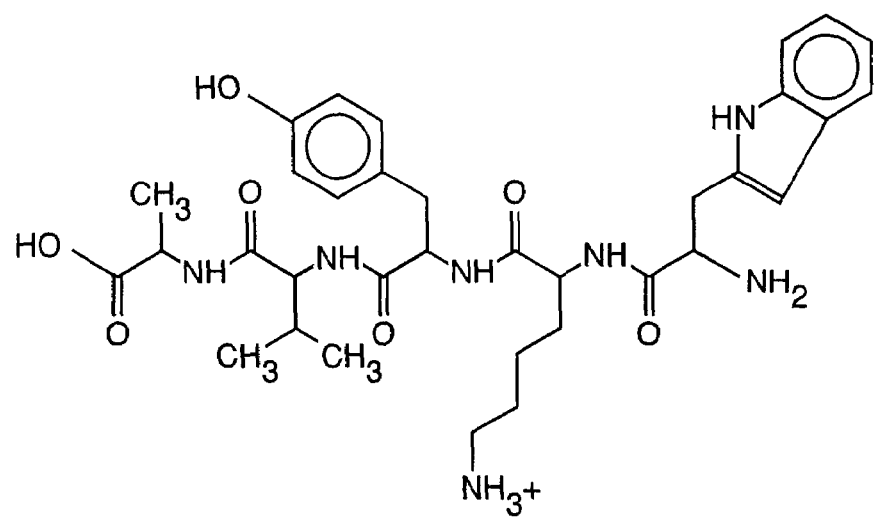
Figure 2:
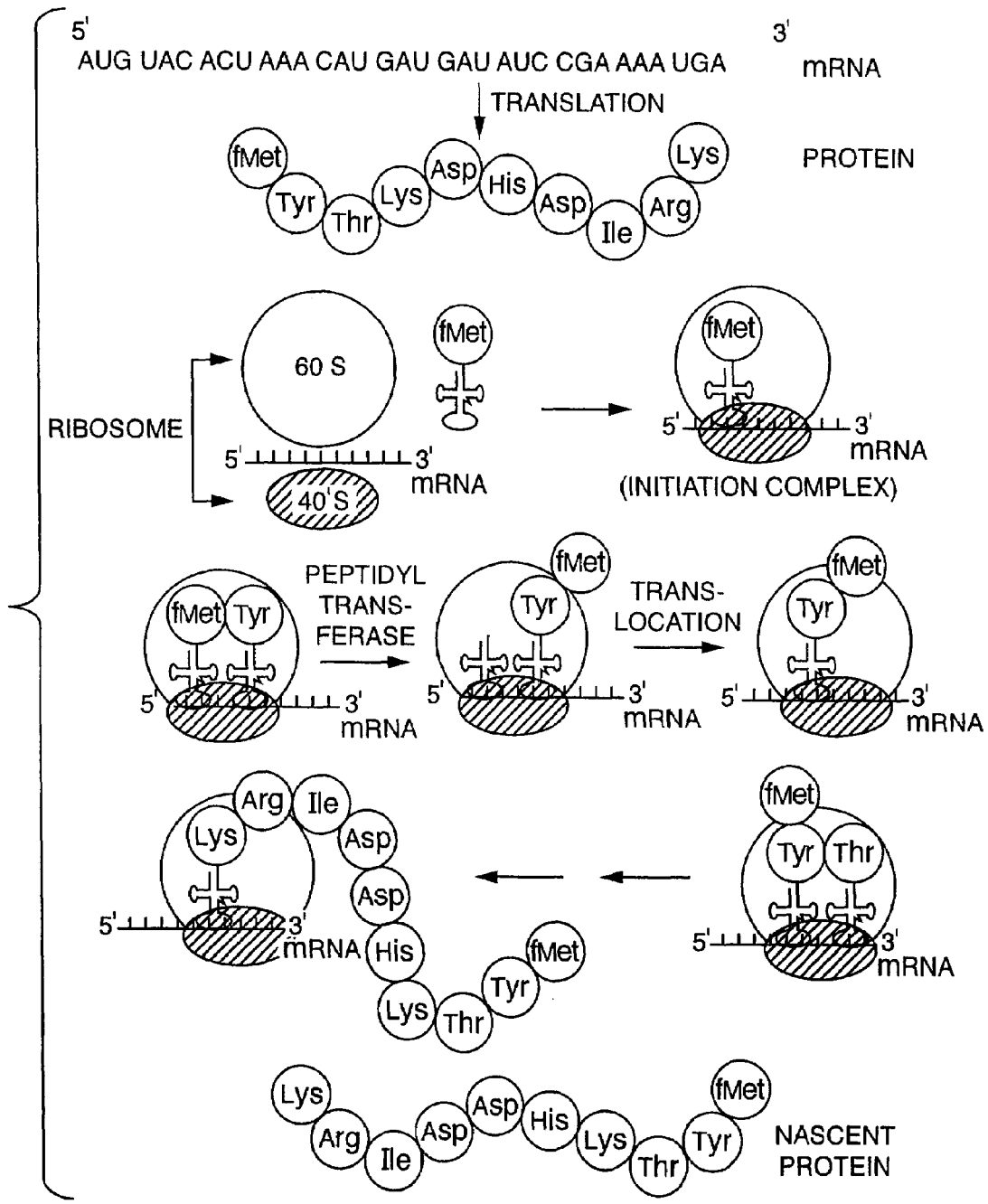
Figure 3A:
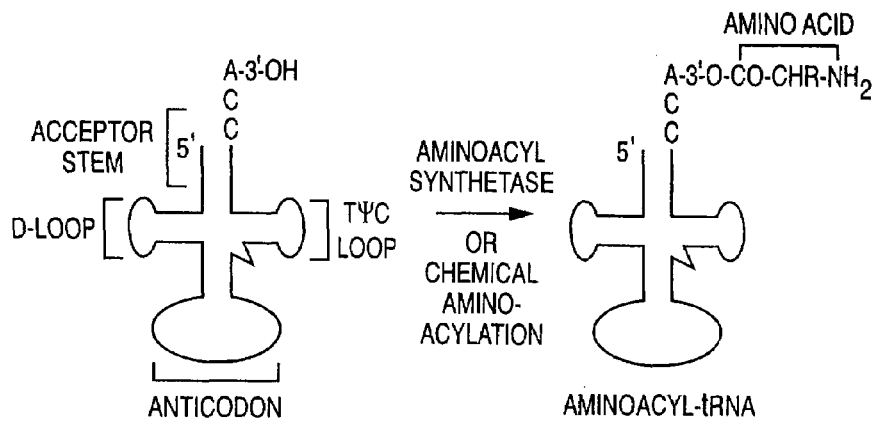
FIG. 3 shows a structure of (A) a tRNA molecule and (B) approaches involved in the aminoacylation of tRNAs.
Figure 3B:
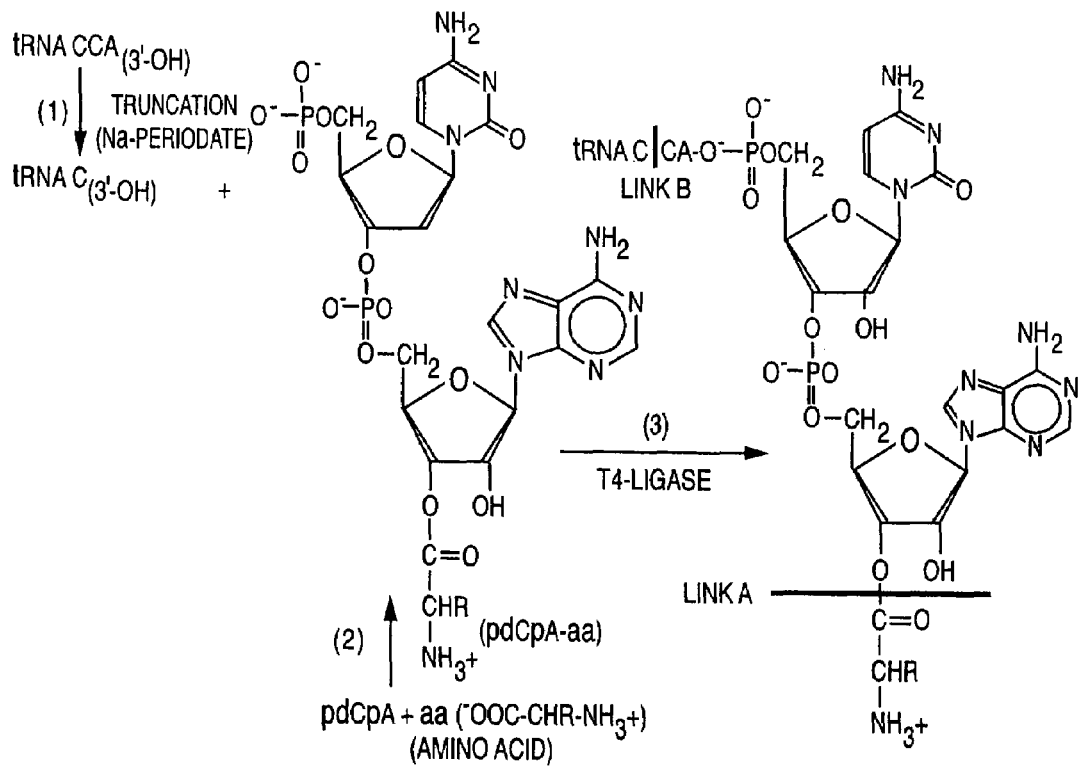
Figure 4:
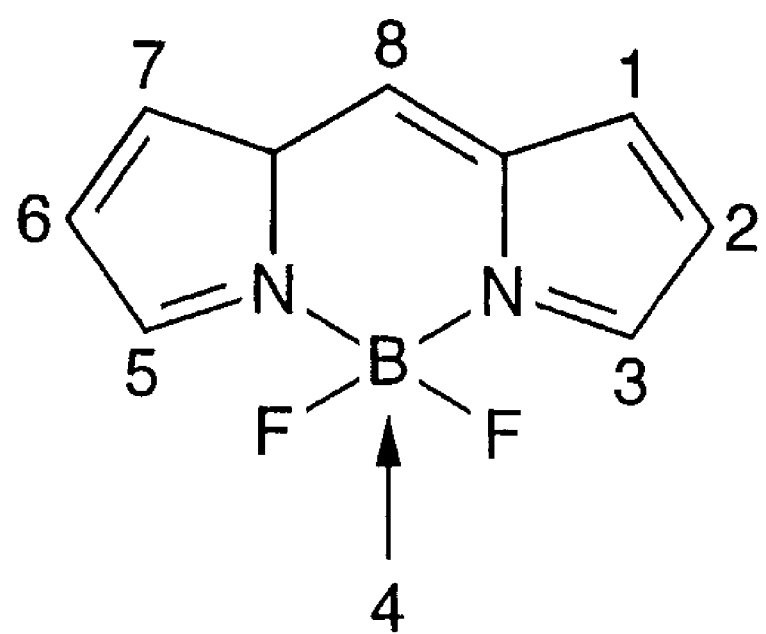
FIG. 4 shows the structure of dipyrrometheneboron difluoride (4,4-difluoro-4-bora-3a,4a-diaza-s-indacene) dyes.
Figure 5A:
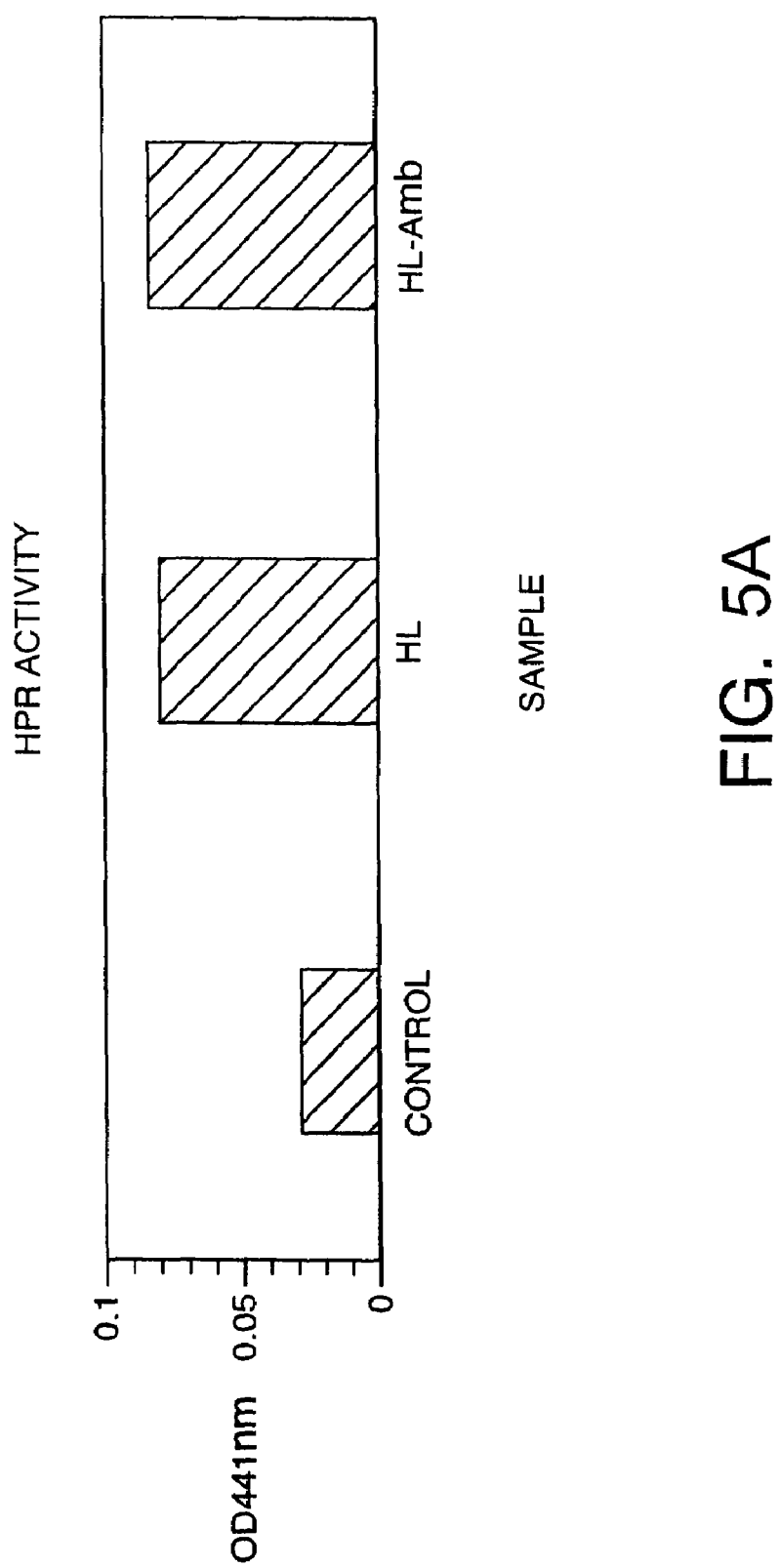
FIG. 5A is a bar graph showing gel-free quantitation of an N-terminal marker introduced into a nascent protein in accordance with one embodiment of the present invention.
Figure 5B:
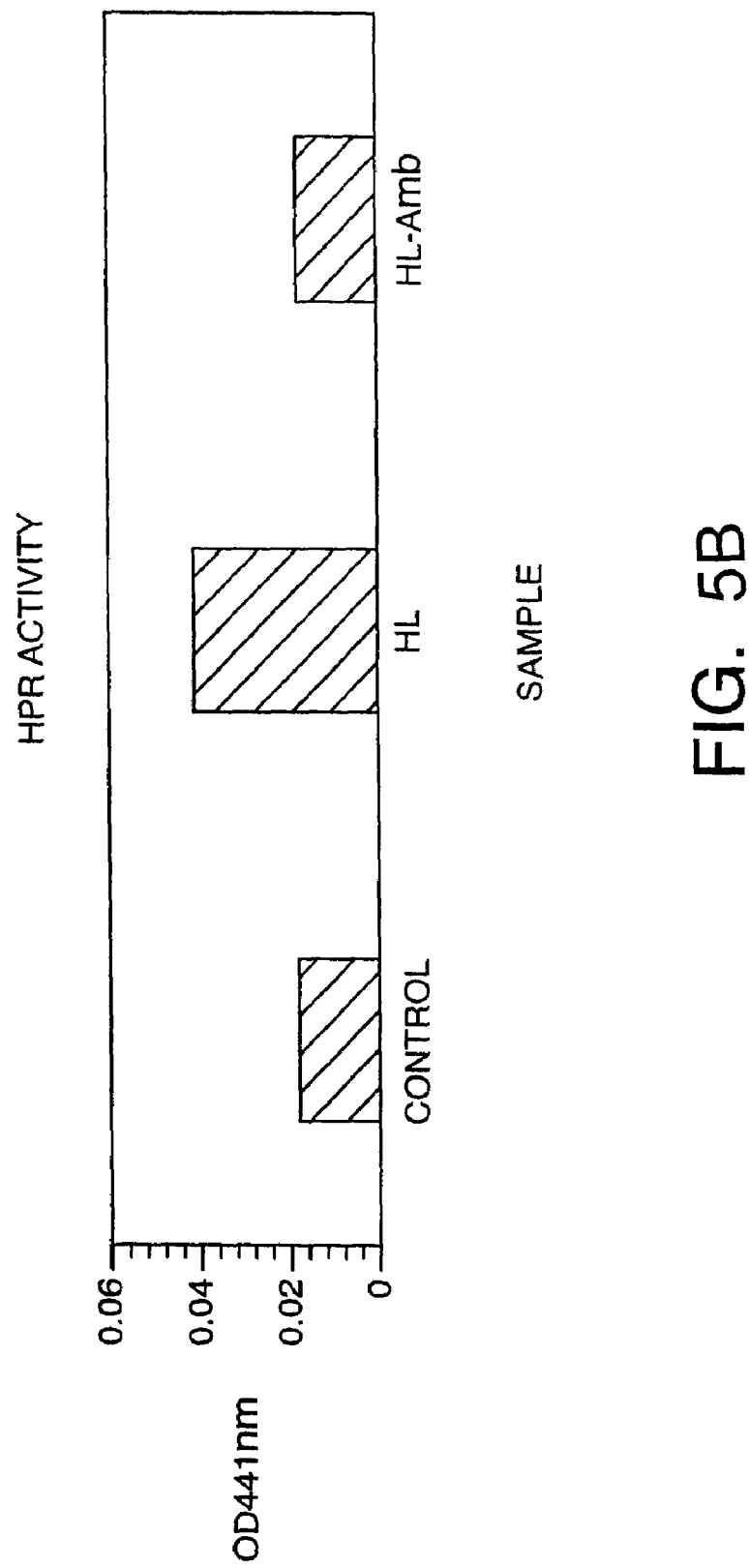
FIG. 5B is a bar graph showing gel-free quantitation of an C-terminal marker of a nascent protein quantitated in accordance with one embodiment of the present invention.

The results of the above-described quantitation are shown in FIG. 5A (quantitation of N-terminal, Biotin marker) and FIG. 5B (quantitation of C-terminal, His-6 marker). In case of in vitro transcription/translation of WT alpha-HL DNA in presence of biotin-methionyl-tRNA, the protein synthesized will have translated His-6 tag at the C-terminal of the protein and some of the alpha-HL molecules will also carry biotin at their N-terminus which has been incorporated using biotinylated-methionine-tRNA. When the total translation reaction mixture containing alpha-HL was incubated on anti-alpha-HL antibody plate, selectively all the alpha-HL will bind to the plate via interaction of the antibody with the endogenous affinity marker. The unbound proteins can be washed away and the N- and C-terminal of the bound protein can be quantitated using Streptavidin-HRP and anti-His-6 antibodies, respectively. In case of WT alpha-HL, the protein will carry both the N-terminal (biotin) and C-terminal (His-6) tags and hence it will produce HRP signal in both the cases where streptavidin-HRP and secondary antibody-HRP conjugates against His-6 antibody used (HL, FIG. 5A). On the other hand, in case of amber mutant alpha-HL, only N-terminal fragment of alpha-HL (first 134 amino acids) will be produced and will have only N-terminal marker, biotin, but will not have His-6 marker due to amber mutation at codon number 135. As a result of this mutation, the protein produced using amber alpha-HL DNA will bind to the antibody plate but will only produce a signal in the case of strepavidin-HRP (HL-AMB, FIG. 5A) and not for anti-His×6 antibodies (HL-AMB, FIG. 5B).

Example 6

Incorporation of Three Markers into Hemolysin

This is an example wherein a protein is generated in vitro under conditions where N- and C-terminal markers are incorporated along with a marker incorporated using a misaminoacylated tRNA. The Example involves 1) PCR with primers harboring N-terminal and C-terminal detectable markers, 2) preparation of the tRNA, 3) in vitro translation, 4) detection of nascent protein.

1. PCR of Alpha-Hemolysin DNA

Plasmid DNA for alpha-hemolysin, pT7-WT-H6-HL, was amplified by PCR using following primers. The forward primer (HL-5) was: 5'-GAATTC-TAATACGACTCACTATAGGGTTAACTTTAAGAAGGAGATATACATATG GAACAAAAATTAATCTCGGAAGAGGATTTGGCAG ATTCTGATATTAATATTAAAACC-3' (SEQ ID NO: 136) and the reverse primer (HL-3) was: 5'-AGCTTCATTA-ATGATGGTGATGG-TGGTGAC 3' (SEQ ID NO:137). The underlined sequence in forward primer is T7 promoter, the region in bold corresponds to ribosome binding site (Shine-Dalgamo's sequence), the bold and underlined sequences involve the C-myc epitope and nucleotides shown in italics are the complimentary region of alpha-hemolysin sequence. In the reverse primer, the underlined sequence corresponds to that of His×6 epitope. The PCR reaction mixture of 100 ul contained 100 ng template DNA, 0.5 uM each primer, 1 mM MgCl$_2$, 50 ul of PCR master mix (Qiagen, Calif.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 2 min, followed by 35 cycles consisted of 95° C. for 1 min, 61° C. for 1 min and 72° C. for 2 min and the final extension at 72° C. for 7 min. The PCR product was then purified using Qiagen PCR clean-up kit (Qiagen, Calif.). The purified PCR DNA was used in the translation reaction.

2. Preparation of BODIPY-FL-lysyl-tRNA$^{lys}$

The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 ul). To this solution 5 ul of 0.5 M CAPS buffer, pH 10.5 was added (50 mM final conc.) followed by 10 ul of 10 mM solution of BODIPY-FL-SSE. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. Varshney et al., *J Biol. Chem.* 266:24712-24718 (1991).

3. Cell-Free Synthesis of Proteins in Eukaryotic (Wheat Germ) Translation Extracts.

The typical translation reaction mixture (20 ul) contained 10 ul of TnT wheat germ extract (Promega Corp., Wisconsin-Madison, Wis.), 0.8 ul of TnT reaction buffer, 2 ul of amino acid mix (1 mM), 0.4 ul of T7 RNA polymerase, 30 picomoles of BODIPY-FL-lysyl-tRNA$^{lys}$, 1-2 ug plasmid or PCR DNA (Example 1) and RNase-free water. The translation reaction was allowed to proceed for 60 min at 30° C. and reaction mixture was centrifuged for 5 min to remove insoluble material. The clarified extract was then precipitated with 5-volumes of acetone and the precipitated proteins were collected by centrifugation. The pellet was dissolved in 1× loading buffer and subjected to SDS-PAGE after boiling for 5 min. SDS-PAGE was carried out according to Laemmli, *Nature*, 227:680-685.

4. Detection of Nascent Protein

After the electrophoresis, gel was scanned using Fluorlmager 595 (Molecular Dyrnanics, Sunnyvale, Calif.) equipped with argon laser as excitation source. For visualization of BODIPY-FL labeled nascent protein, we have used 488 nm as the excitation source as it is the closest to its excitation maximum and for emission, we have used 530+/−30 filter. The gel was scanned using PMT voltage 1000 volts and either 100 or 200 micron pixel size.

Figure 6:
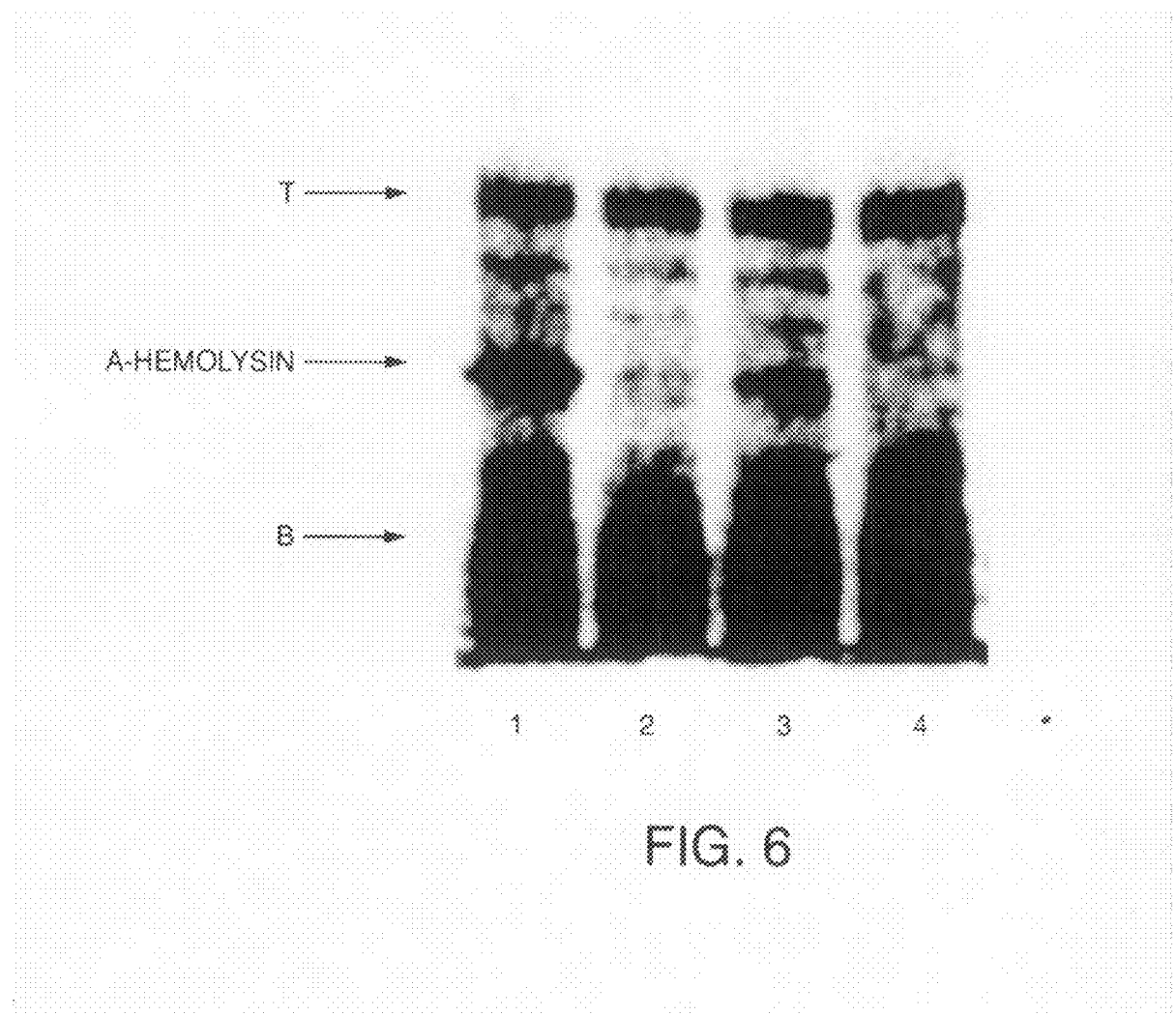
FIG. 6 are gel results of in vitro translation results wherein three markers were introduced into a nascent protein.

The results are shown in FIG. 6. It can be seen from the Figure that one can in vitro produce the protein from the PCR DNA containing desired marker(s) present. In the present case, the protein (alpha-hemolysin) has a C-myc epitope at N-terminal and His×6 epitope at C-terminal. In addition, BODIPY-FL, a fluorescent reporter molecule is incorporated into the protein. Lane 1: alpha-Hemolysin plasmid DNA control; lane 2: no DNA control; lane 3: PCR alpha-hemolysin DNA and lane 4: hemolysin amber 135 DNA. The top (T) and bottom (B) bands in all the lane are from the non-specific binding of fluorescent tRNA to some proteins in wheat germ extract and free fluorescent-tRNA present in the translation reaction, respectively.

Example 7

Primer Design

It is not intended that the present invention be limited to particular primers. A variety of primers are contemplated for use in the present invention to ultimately incorporate markers in the nascent protein (as explained above). The Example involves 1) PCR with primers harboring markers, 2) in vitro translation, and 3) detection of nascent protein.

For PCR the following primers were used: forward primer: 5'GGATCC <u>TAATACGACTCACTATAGGG</u>AGACCACCATG GAACAAAAATTAATATCGGAAGAGGATTTGAATGT TTCTCCATACAGGTCACGGGGA-3' (SEQ ID NO:138). Reverse Primer: 5'-TTATTAATGATGGTGATGGTGGTG-TTCTGTAGGAATGGTATCTCGTTTTTC-3' (SEQ ID NO:139) The underlined sequence in the forward primer is T7 promoter, the bold and underlined sequences involve the C-myc epitope and nucleotides shown in italics are the complimentary region of alpha-hemolysin sequence. In the reverse primer, the bold sequence corresponds to that of His-6 epitope and the underlined sequence corresponds to the complimentary region of the alpha-hemolysin sequence. In a preferred embodiment, the reverse primer further comprises a sequence which will generate a stop codon if there is a frameshift: TTT-ATT-TAT. An example of such a design for a reverse primer is as follows: 5'-TTATTA-ATGATGGT-GATGGTGGTG-TTTATTTAT-TTCTGTAGGAATGGTATCTCGTTTTTC-3' (SEQ ID NO:140)(wherein the underlined bolded section shows this sequence. A PCR reaction mixture of 100 ul can be used containing 100 ng template DNA, 0.5 uM each primer, 1 mM MgCl$_2$, 50 ul of PCR master mix (Qiagen, Calif.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 2 min, followed by 35 Cycles consisted of 95° C. for 1 min, 61° C. for 1 min and 72° C. for 2 min and the final extension at 72° C. for 7 min. The PCR product can then be purified using Qiagen PCR clean-up kit (Qiagen, Calif.). The purified PCR DNA can then be used in a variety of translation reactions. Detection can be done as described above.

Overall, the present invention contemplates a variety of primer designs based on the particular epitopes desired (see Table 3 for a list of illustrative epitopes). In general, the epitopes can be inserted as the N-terminus or C-terminus. In addition, they can be used to introduce an affinity region (i.e. a region which will bind to antibody or other ligand) into the protein.

Example 8

Antibody Detection of Primer-Encoded Epitopes

This is an example wherein a protein is generated in vitro under conditions where affinity regions are incorporated in a protein and thereafter detected. The Example involves 1) PCR with primers containing sequences that encode epitopes, 2) preparation of the tRNA, 3) in vitro translation, 4) detection of nascent protein.

1. PCR with Primer-Encoded Epitopes

The total RNA from the human colon (Clontech, Palo Alto, Calif.) was subjected to one-step RT-PCR reaction using ClonTech RT-PCR Kit. The forward Primer, PTT-T7-P53, was 5'-GGATCC <u>TAATACGACTCACTATAGGG</u>AGACCACCA-TGGGAC ACCACCATCACCATCACGGAGATTA-CAAAGATGACGATGACAAA-GAGGAGCCGCAGT-CAGATCCTAGCGTCGA-3' (SEQ ID NO:141) and the reverse primer, Myc-P53-3', was 5'-ATTATTA <u>CAAATCCTCTTCCGAGATTAATT</u>-TTTGTTCGTCTGA GTCAGGCCCTTCTGTCTTGAACATG-3' (SEQ ID NO:142). The underlined sequence in forward primer is T7 promoter, the nucleotides shown in italics corresponds to that of His-6 tag while the sequence in bold codes for FLAG-epitope and the rest of primer is the complementary region for P53 DNA. In the reverse primer, the underlined sequence corresponds to that of c-Myc epitope.

The RT-PCR/PCR reaction mixture of 50 μL contained 1 μg total human colon RNA, 0.5 μM each primer, 43.5 μL of RT-PCR master mix (ClonTech) and nuclease free water (Sigma Chemicals, St. Louis, Mo.). The RT-PCR/PCR was carried out in a PTC-150 thermocycler (MJ Research, Waltham, Mass.) using the following conditions: 5° C. for 1 hour, 95° C. for 5 mm followed by 40 Cycles consisting of 95° C. for 45 sec, 60° C. for 1 mm and 70° C. for 2 mm and the final extension at 70° C. for 7 mm. The PCR product was analyzed on 1% agarose gel and the PCR amplified DNA was used in the translation reaction without any further purification. The artificial C-terminal truncated mutant of P53 was prepared using the identical procedure described above except the reverse primer, 3'-P53-Mut, was 5'-CTCAT-TCAGCTCTCGGAACATC-TCGAAGCG-3' (SEQ ID NO:143).

2. tRNA Labelling

Purified tRNA$^{lys}$ (Sigma Chemicals, St. Louis, Mo.) was first amino-acylated with lysine. The typical aminoacylation reaction (100 ul) contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (35 ul). To this solution 5 ul of 0.5M CAPS buffer, pH 10.5 was added (final concentration of 50 mM) followed by 10 ul of 10 mM solution of BODIPY-FL-SSE. The mixture was incubated for 10 minutes at 0° C. and the reaction was quenched by the addition of free lysine (final concentration=100 mM). To the resulting solution 0.1 volumes of 3 M NAOAc (pH=5.0) was added and the modified tRNA was precipitated with 3 volumes of ethanol. Precipitate was dissolved in 50 ul of RNase-free water and passed through Sephadex G-25 gel filtration column (0.5×5 cm) to remove any free fluorescent reagent, if present. The modified tRNA was stored frozen (−70° C.) in small aliquots in order to avoid freeze-thaws. The modification extent of the aminoacylated-tRNA was assessed by acid-urea gel electrophoresis [Varshney, U., Lee, C. P. & RajBhandary, U. L., *J Biol. Chem.* 266, 24712-24718 (1991)] or by HPLC [*Anal. Biochem.* 279:218-225 (2000)].

3. Translation

Translation of P53 DNA (see step 1, above) was carried out in rabbit reticulocyte translation extract in presence of fluorescent-tRNA (step 2, above).

4. Detection

Once the translation was over, an aliquot (5 ul) was subjected to SDS-PAGE and the nascent proteins were visualized using FluorImager SI (Molecular Dynamics, Sunnyvale, Calif.). After visualization, the gel was soaked in the transfer buffer (12 mM Tris, 100 mM glycine and 0.01% SDS, pH 8.5) for 10 min. Proteins from the gels were then transferred to PVDF membrane by standard western blotting protocol using Bio-Rad submersion transfer unit for 1 hr. After the transfer, then membrane was reversibly stained using Ferrozine/ferrous total protein stain for 1 min to check the quality of transfer and then the membrane was blocked using amber blocking solution (4.5% v/v teleostean gelatin, 2% w/v nonfat milk powder, 0.1% w/v Tween-20 in Tris-buffered saline, pH 7.5) for 2 hours followed by overnight incubation (12-15 hours at 4° C. on constant speed shaker) with appropriately diluted antibodies. For Flag detection, we have used 2000-fold diluted anti-Flag M2 Antibody (Sigma), for His-6 detection, we have used 500-fold anti-His6 antibody (Santa-Cruz Biotech, Calif.) and for c-Myc detection, we have used 500-fold diluted anti-C-Myc antibody (Santa-Cruz Biotech, Calif.).

After primary antibody incubation, the membrane was washed with TBST (Tris-buffered saline, pH 7.5 with 0.1% Tween-20) four times (10 min each wash) and incubated with appropriately diluted secondary antibodies (10,000-fold diluted) for 1 hour at room temperature on constant speed shaker. The unbound secondary antibodies were washed with TBST (4 washes/10 min each) and the blot was visualized using an ECL-Plus chemiluminescence detection system (Amersham-Pharmacia Biotech, N.J.).

The results are shown in FIGS. 7A and 7B. FIG. 7A shows the total protein stain of PVDF membranes following protein transfer from the gel for three replicate blots containing a minus DNA negative control and a plus p53 DNA sample respectively. FIG. 7B shows the same blots (total protein staining is reversible) are probed with antibodies against the three epitope tags using standard chemiluminescent Western blotting techniques. Arrows indicate the position of p53.

Example 9

Gel-Free PTT for Cancer Genes

Although the replacement of radioactivity with fluorescent labels represents an improvement in current PTT technology, it still relies on the use of gels, which are not easily adaptable for high-throughput screening applications. For this reason, this example demonstrates a non-gel approach based on the use of chemiluminescent detection. In this approach, a cancer-linked protein or polypeptide fragment from the protein is expressed in vitro from the corresponding gene with different detection and binding tags incorporated at the N-terminal, C-terminal and between the two ends of the protein using a combination of specially designed primers and tRNAs. The detection and binding tags provide a means to quantitate the fraction of protein or protein fragment which is truncated while the tags located between the two ends of the protein can be used to determine the region of truncation. For example, a full-length protein would contain both an N and C-terminal tag, whereas a truncated protein would contain only the N-terminal tag. The signal from a tag incorporated at random lysines between the two ends of the protein (intrachain signal) would be reduced proportional to the size of the truncated fragment. It is important to also capture the protein with a marker located close to the N-terminus in order to avoid interference of chain truncations with binding.

In order to evaluate this method, we performed experiments on the APC and p53 genes containing either a WT sequence or truncating mutations. In both cases, a combination of primers and specially designed tRNAs were used to incorporate a series of markers into the target proteins during their in vitro synthesis in a rabbit reticulocyte system. After in vitro expression, the expressed protein was captured in 96-well ELISA plates using an affinity element bound to the plate. The relative amount of N-terminal, C-terminal and intrachain signal was then determined using separate chemiluminescent-based assays.

1. PCR of Cancer Genes

A. APC Segment 3

First, the genomic DNA (WT and isolated from cell lines harboring mutant APC gene) was amplified by PCR using the following primers. The forward primer, PTT-T7-ALPC3, was 5'-GGATCC <u>TAATACGACTCACTATAGGG</u>AGACCACCATG-CACC ACCATCACCATCACGGAGGAGATTA-CAAAGATGACGATGACAAA-GTTTCTCCATACAGGT-CACGGGGAGCCAAT-3' (SEQ ID NO:144) and the reverse primer, PTT-Myc-APC3, was 5'-ATTATTA <u>CAAATCCTCTTCCGAGATTAA-TTTTTGTTC</u>ACTTCTGCCTTCTGTAGGAATGGTATC TCG-3'-(SEQ ID NO:145). The underlined sequence in the forward primer is T7 promoter, nucleotides shown in italics correspond to that of His-6 tag while the nucleotide sequence shown in the bold codes for FLAG-epitope and the rest of the primer is the complementary region for APC segment 3 DNA. In the reverse primer, the underlined sequence corresponds to that of c-Myc epitope. The PCR/reaction mixture of 50 μL contained 200-500 ng template DNA (either WT or mutant), 0.5 μM of each primer and 25 μL of PCR master mix (Qiagen, Calif.) and nuclease free water (Sigma Chemicals, St. Louis, Mo.) water. The PCR was carried out using a Hybaid Omni-E thermocycler (Hybaid, Franklin, Mass.) fitted with a hot-lid using the following conditions: 95° C. for 3 mm, followed by 40 cycles consisting of 95° C. for 45 sec 55° C. for 1 mm and 72° C. for 2 mm and the final extension at 72° C. for 7 mm. The PCR product was analyzed on 1% agarose gel and the PCR amplified DNA was used in the translation reaction without any further purification.

B. P53

The p53 DNA was prepared as described above.

2. Preparation of the tRNA

The BODIPY-FL-lysyl-tRNA$^{lys}$ was prepared as described above. Preparation of Biotin-lysyl-tRNA$^{lys}$ and PC-Biotin-lysyl-tRNA$^{lys}$ was achieved as follows. The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl-tRNA-synthetases (Sigma Chemicals, St. Louis, Mo.). The reaction mixture was incubated for 45 mm at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 μL). To this solution 5 μL of 0.5 M CAPS buffer, pH 10.5 was added (50 mM final conc.) followed by 10 μL of 10 mM solution of either biotin or photocleavable-biotin. The mixture was incubated for 10 mm at 0° C. and the reaction was quenched by the addition of lysine (final concentration=100 mM). To the resulting solution 0.1 volume of 3 M NaOAc, pH 5.0 was added and the modified tRNA was precipitated with 3 volumes of ethanol. Precipitate was dissolved in 50 µL of water and purified on a Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & Rajbhandary, U. L., 1991, J. Biol. Chem. 266, 2471224718).

3. Translation

The typical translation reaction mixture (20 µl) contained 16 µl of TNT rabbit reticulocyte extract for PCR DNA (Promega, Madison, Wis.), 1 µl of amino acid mix (1 mM), 1-2 µL of PCR DNA (see APC and p53 preparation described above) and RNase-free water. For fluorescence detection, the BODIPY-FL-lysyl-tRNA$^{lys}$ was included into the translation reaction mixture. The translation reaction was allowed to proceed for 60 mm at 30° C.

4. Detection

FIG. 8A shows the results of an initial experiment designed to detect a chain truncation introduced into the p53 protein during RT-PCR In this case an N-terminal FLAG epitope was used for capture (see the description of the capture assay using 96-well ELISA plates at the beginning of the EXPERIMENTAL section), and His$_6$ and c-myc used for the N- and C-terminal markers, respectively. Detection of the N-terminus His-tag was achieved using a peroxidase labeled nickel chelate-based detection probe (India™ His Probe-HRP, Pierce, Rockford, Ill.). Detection of the C-terminus was performed using a rabbit polyclonal antibody directed against the human c-myc epitope followed by a peroxidase labeled mouse anti-[rabbit IgG] secondary antibody. As seen, the ratio of C/N terminal signals is reduced approximately 25-fold for the truncated protein compared to WT. Further optimization of this assay should result in sensitivity sufficient to detect truncating mutations in 1/100 mutant/WT p53 proteins, thus enabling applications to non-invasive colon cancer screening.

In a second experiment (FIG. 8B), capture was facilitated with an N-terminal His$_6$-tag, while FLAG and c-myc were used as N and C-terminal markers, respectively. In addition, an intrachain photocleavable biotin marker was incorporated by adding PC-Biotin-Lys-tRNA to the in vitro mixture. Biotin detection was achieved using peroxidase labeled NeutrAvidin™ (Pierce). The results show a 13-fold reduction in the C/N ratio for truncated p53 Compared to WT. Furthermore, the intrachain biotin signal drops by 75% relative to the N-terminal signal.

A third chemiluminescent protein truncation assay was designed to detect chain truncation in the APC gene of a mutant cell line (FIG. 8C). Capture was facilitated with an N-terminal His$_6$-tag, while FLAG and c-myc were used as N and C-terminal markers, respectively. As seen in FIG. 8C, the truncated APC exhibits a marked drop in the C/N ratio (1/6) again indicating the presence of a chain truncation.

Overall, these experiments demonstrate the ability to detect chain-truncating mutations in cancer-linked proteins using a gel-free chemiluminescent approach.

Example 10

Detection of Protease Activity in Extracts

Genomic DNA and RNA (WT and APC mutant) was isolated from established cell lines CaCo-2 (C1), HCT-8 (C2) and SW480 (C3) as well as from patient blood samples using commercially available kits (Qiagen, Valencia, Calif.). PCR amplification of a selected region of the APC gene (APC segment 3) was carried out using 250-500 ng of genomic DNA, 0.2 uM primer mix (forward and reverse) and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 2 min and a final extension step at 72° C. for 10 min. RT-PCR amplification of APC gene (APC segment 3) was carried out using one-step RT-PCR/PCR kit from ClonTech (Palo Alto, Calif.). RT-PCR reaction contained 500 ng of total RNA, 0.2 uM primer mix (forward and reverse) and 1× RT-PCR master mix. Amplification conditions were the same as above with an additional initial cycle of reverse transcription at 50° C. for 1 hour. The primer pair was: Forward: (SEQ ID NO:146) 5'-GGATC-CTAATACGACTCACTATAGGGAGACCACC-*ATG*-GGC-TACACCGACAT-CGAGATGAACCGCCTGG CAAG-GTTTCTCCATACAGGTCACGGGGAGCC-3'
Reverse: (SEQ ID NO:147) 5'-TTATTACAGCAGCTTGTG-CAGGTCGCTGAAGGTACTTCTGCCTTCTGT-*AG-GAATGTATC*-3'

The italicized nucleotides in the forward primer correspond to the T7 promoter, the underlined ATG is the initiation codon, the boldface nucleotide region codes for the N-terminal tag (VSV-G; YTDIEMNRLGK: SEQ ID NO:148) and the remaining nucleotide sequences correspond to the complementary region of the APC gene. In the reverse primer, the boldface nucleotides code for the C-terminal tag (P53 sequence derived tag; TFSDLHKLL: SEQ ID NO:149) while the rest of the nucleotide sequence is complementary to the APC gene and nucleotides in italics codes for 2 successive stop codons. After amplification, the quality and quantity of the PCR products was analyzed by agarose gel electrophoresis.

The cell-free reaction mixture contained 8 µl of TNT T7 Quick Rabbit Reticulocyte lysate for PCR DNA (Promega, Madison, Wis.), 0.5 µl of a complete amino acid mix and 0.5 µl of DNA (approximately 200 ng) and 1 µl of biotin-lysyl-tRNA. The translation reaction was allowed to proceed for 30 min at 30° C. After the incubation, the reaction mixture was divided into two aliquots and to one, cycloheximide (1 uM) was added and further incubated up to 240 min. Aliquots (10 ul) were taken at 30, 60, 120 and 240 min and the N-terminal and C-terminal signals were determined by ELISA as given below.

After the incubation of translation mixture, the reaction mixture was diluted 30-fold with TBS containing 0.05% Tween-20, 0.1% Triton X-100, 5% BSA, and both antibodies (anti-VSV-G-HRP (Roche Applied Sciences, Indianapolis, Ind.) at 80 ng/mL and anti-p53-alkaline phosphatase (Santa Cruz Biotechnology, Santa Cruz, Calif.) at 100 ng/mL). Subsequently, 100 µl of the diluted reaction mixture was added to each well of a NeutrAvidin™ coated 96-well plate (pre-blocked with 5% BSA) and incubated for 45 min on an orbital shaker. NeutrAvidin™ was obtained from Pierce Chemicals (Rockford, Ill.) and Microlite2+multiwell plates were obtained from Dynex Technologies (Chantilly, Va.). The plate was washed 5× with TBS-T (TBS with 0.05% Tween-20) followed by 2× with TBS and developed using a chemiluminescent alkaline-phosphatase (AP) substrate (Roche Biochemicals, Indianapolis). After the AP readings, plates was washed with 2 times with TBS and HRP signal was measured using chemiluminescent HRP substrate (Supersignal Femto, Pierce Chemicals, Rockford, Ill.).

The results of effect of the addition of cycloheximide (CH) on the translation and N- and C-terminal signal are shown in the FIG. 9. It is clear from the data obtained that the addition of cycloheximide results in the rapid decrease in N- and C-terminal signals (+CH VSV signal and +CH p53 signal) since the protein synthesis is completely inhibited and the nascent protein synthesized before the addition of cycloheximide is degraded by proteases present in the translation extract. On the other hand, when the cycloheximide was not added (i. e. protein synthesis was not inhibited), the decrease in N- and C-terminal signals is much slower (−CH VSV signal and −CH p53 signal) indicating the equilibrium process between synthesis and degradation. These results clearly indicate the presence of protein degrading (proteolytic) activities in the rabbit reticulocyte extract.

Example 11

A Penta-Lysine 5'-Tag

The use of biotin-lysyl-tRNA to incorporate biotin affinity tags at lysine residues would result in no capture if the chain truncation occurs upstream of the first lysine. This problem and the overall efficiency of capture can be improved if an extra lysine sequence are artificially added in the beginning the transcript. This can be achieved by adding 5 extra lysine coding nucleotides in the 5' primer after an ATG codon or after the epitope coding nucleotides. This design of the transcript then can increase the overall number of lysine residues resulting in the increased incorporation of biotin using biotin-tRNA$^{lys}$. It is contemplated that the lysine tag includes, but is not limited to, from between 3-10 lysine residues.

FIG. 10 depicts ELISA data showing increased signal in samples having extra lysine residues using shorter nascent proteins (WT is 70 kD nascent protein while is N3 is a mixture of 70 and 30 kD nascent proteins).

Example 12

MALDI-Mass Spectrometry (MALDI-MS) Mutation Detection

This example utilizes alpha-HL with a C-terminal His6-tag, which was expressed in a S30 reaction mixture using a high-expression plasmid containing the alpha-HL gene under control of the T7 promoter.

For comparison, a mutant of alpha-HL (S302W) was also expressed in E. coli translation extract. In both cases, the proteins were isolated from the translation reaction mixture using Co$^{2+}$-NTA chromatography. The isolated protein was dialyzed, concentrated and deposited on a MALDI substrate. As seen in FIG. 11, a peak is observed at 34,884 Da for WT alpha-HL and 34,982 Da for the mutant alpha-HL, in good agreement with calculated masses (34,890 and 34,989 Da, respectively). This demonstrates the ability of MALDI to detect a mutation in an in vitro expressed protein.

Example 13

Detection of Protease Activity with Epitope Peptides

Two biotinylated peptides, a VSV peptide with an amino aid sequence MYTDIEMNRLGK (SEQ ID NO:150) and P53 peptide with an amino acid sequence TFSDLWKLL (SEQ ID NO:151) were synthesized. These peptides were used to detect the presence of proteolytic activities in the cell-free translation extracts such as rabbit reticulocyte, E. coli and Wheat germ. In one experiment, 3 pmol of biotinylated VSV peptide was incubated at 30° C. in either 100 ul Tris-buffer saline, rabbit reticulocyte extract or heat denatured rabbit reticulocyte extract (by boiling at 100° C. for 5 min in presence of SDS). In other experiment, 10 pmol of biotinylated P53 peptide was incubated at 30° C. in either 100 ul Tris-buffer saline, rabbit reticulocyte extract or heat denatured rabbit reticulocyte extract (by boiling at 100° C. for 5 min in presence of SDS). At a given time interval, 10 ul aliquots were removed and subjected to ELISA assay as described above. The results of these experiments are presented in FIGS. 12 and 13. It can be seen from the FIG. 12 that when the VSV peptide was incubated in buffer only, no loss of peptide signal was observed. On the other hand, when the peptide was incubated in rabbit reticulocyte lysate, complete loss of peptide signal was observed within 10 min of incubation. Similar results were also obtained for p53 peptide (FIG. 13). When the peptide was incubated in denatured rabbit reticulocyte extract, it retains complete peptide signal. These results show that there is significant protein/peptide degrading activity present in the cell-free translation extract.

Example 14

Impact of Protease Inhibitors on Extract Protease Activity

The peptides (VSV and P53) were incubated with rabbit reticulocyte extract treated with protease inhibitor cocktail "PIC" (Roche Applied Sciences, Indianapolis, Ind.). After 30 min of protease cocktail treatment, these peptides were incubated in the treated translation extract for 5-45 minutes and at given time interval 10 ul aliquots were removed. The residual peptide signal was then determined by ELISA as described before. The results of this experiment are presented in FIGS. 14 and 15. It can be seen from the FIG. 14 that when the peptide was incubated in buffer alone, no loss of peptide signal was observed. On the other hand, when the peptide was incubated in rabbit reticulocyte lysate, complete loss of peptide signal was observed within 10 min of incubation. This complete loss of VSV peptide signal can be avoided by pre-treating the rabbit reticulocyte extract with a protease inhibitor cocktail. The P53 peptide required higher amounts of protease cocktail inhibitor (FIG. 15) and was subject to increased degradation over time (even at the higher inhibitor concentration). These results show that there is significant protein/peptide degrading activity present in the cell-free translation extract and this proteolytic activity can be partially inhibited by pre-treating the translation extract with a protease inhibitor cocktail.

Example 15

Protease Inhibitors and Nascent Protein Production

Even if protease inhibitors can reduce degradation from exposure to the extract, there is the concern that such inhibitors will interfere with protein production. PCR product from example 10 was used for the production of nascent protein using rabbit reticulocyte lysate in the presence of various amounts of protease inhibitor cocktail (Roche Applied Sciences, Indianapolis, Ind.). The translation was carried out as described. The translation was allowed to proceed for 45 min and the amount of nascent protein produced was determined by the ELISA assay. Briefly, the biotinylated nascent protein was captured on the neutravidin coated plate and the amount of nascent protein produced was determined by measuring N-terminal (VSV) and C-terminal (P53) signal using anti-VSV-HRP and anti-P53-AP antibody, respectively. The results of the translation reaction in the absence and presence of protease inhibitor are shown in the FIG. 16 (1× refers to the concentration suggested by the vendor). It can be seen from the Figure that the translation efficiency is not significantly inhibited up to the 5× concentration of the inhibitor mix. However, at higher concentrations there is a significant reduction.

Example 16

Protease Activity in a Reconstituted System

As shown above, the various commercially available translation extracts such as rabbit reticulocyte and *E. coli* extract (Promega Corp., Madison, Wis.) contain significant protease activity. In this experiment, the protease activity of a newly available reconstituted system (the "PURE" translation system) is evaluated (Post genome Institute, Japan). In this experiment, 1 pmol of biotinylated VSV peptide was incubated at 30° C. in either 100 μl Tris-buffer saline, rabbit reticulocyte extract or heat denatured rabbit reticulocyte extract (by boiling at 100° C. for 5 min in presence of SDS), *E. coli* or heat denatured *E. coli* translation extracts as well as PURE or denatured PURE translation extract. At a given time interval (5 and 45 min), 10 ul aliquots were removed and subjected to ELISA assay as described above. The results of this experiment are presented in FIG. 17. It can be seen from the Figure that when the peptide was incubated in a buffer alone, no loss of peptide signal was observed. On the other hand, when the peptide was either incubated in rabbit reticulocyte lysate or *E. coli* lysate, complete loss of peptide signal was observed within 5 min of incubation. In addition, PURE system, which is made of purified translation machinery components, shows significant proteolysis for the P53 peptide at 5 min and increased peptide degradation when the incubation was prolonged to 45 min (even though the "PURE" system is advertised to be protease-free). Again, when the peptide was incubated with heat-denatured extracts, it etained complete peptide signal. These results show that even reconstituted systems contain protease activity.

Example 17

Detection of Protease Activity by Mass Spectrometry

In this experiment, the protease-sensitive peptide ("R6") was employed, which has a sequence of MDYKD-DDDKRRRRRRFFF (SEQ ID NO:152). The residues in italics correspond to the FLAG epitope located at the N-terminus. The peptide concentration used was either 1 nmole/μL or 100 pmole/μL. In one experiment, 10 μL of RRL extract was mixed with either 2 μL (2 nmole total peptide amount) or 5 μL (50 pmole) peptide solution and incubated for 30 s, 2 min or 5 min at 30° C. The reaction was terminated by addition of 100 μL of 100 mM EDTA and the solution was immediately applied to the microcolumn containing 1 μL of Sigmna ANTI-FLAG beads. The beads were then washed with 50 μL of 20 mM Tris-HCl, pH 7.2 and the bound peptide was eluted with approximately 4 μL of matrix solution (CHCA/acetonitrile/TFA) directly onto a MALDI plate. In a control experiment, 5 μL (50 pmole) of pure peptide solution was applied to the microcolumn containing ANTI-FLAG beads, washed and eluted as described above.

Incubation of 50 pmole of peptide with the buffer shows a very good mass peak at 2534 (FIG. 18, top panel). The peak at 1268 is doubly charged species of the same peptide. Incubating this peptide in rabbit reticulocyte lysate even for 1 min results in a partial disappearance of the peak corresponding to the intact peptide, which is observed near 2535 in the mass-spectra as well as the appearance of several peptides of smaller masses (FIG. 18, middle panel) which can be identified as the products of exo-proteolysis. In particular, weak bands near 2387 and 2238 are close to the expected peptide fragments, which lack one and two phenylalanines, respectively. The peak corresponding to the peptide fragment with all three Phe groups removed is either very weak or absent. Peptide fragments with three Phe groups and 1, 2, 3 and 4 Arg groups removed give rise to peaks observed at 1934, 1778, 1621 and 1268, respectively. The peak at 1268 is due to the intact peptide ($M^{2+}$). Furthermore, incubation of this peptide in rabbit reticulocyte extract for 5 min results in complete loss of intact peptide (FIG. 18, bottom panel). Since the purification procedure requires the intact FLAG epitope to be present, it was not possible to detect fragments that correspond to N-terminal degradation (if such fragments exist). The results presented here demonstrate that the RRL system is capable of rapidly degrading picomolar amounts of short peptides. The observed peaks indicate that the proteolysis occurs from the C-terminal end and therefore the protease might be a carboxypeptidase.

Example 18

Inhibiting Protease Activity Detected by Mass Spectrometry

In this experiment, protease inhibitors were tested to inhibit the degradation of the peptide R6 (described above). In one experiment, 10 μL of rabbit reticulocyte extract was pre-treated by incubating with a specific protease inhibitor such as ebelactone or 2-LeuLeuNVa-CHO for 10-15 min. Following pretreatment, peptide R6 was added to above translation mix and incubated for 10 min at 30° C. The reaction was terminated by addition of 100 μL of 100 mM EDTA and the solution was immediately applied to the microcolumn containing 1 µL of Sigma ANTI-FLAG beads. The beads were then washed with 50 µL of 20 mM Tris-HCl, pH 7.2 and the bound peptide was eluted with approximately 4 µL of matrix solution (CHCA/acetonitrile/TFA) directly onto a MALDI plate. In the control experiment, extract pre-treated with buffer was used and processed as described above. Similar experiments were carried out using *E. coli* translation extract.

Incubation of 50 pmole of peptide with the rabbit reticulocyte extract treated with buffer (control) shows the disappearance of peptide peak (mass=2535) as a result of proteolysis (FIG. 19, Top panel). On the other hand, peptide incubated in rabbit reticulocyte extract which was pretreated with protease inhibitor (2-LeuLeuNvaCHO) shows a significant reduction in protease activity, which is evident from the detection of a significant peptide peak appearing at its original mass corresponding to an intact R6 peptide (FIG. 19, Bottom panel). Another protease inhibitor, namely, Ebelactone, shows only weak protease inhibition (Figure I, Middle panel). FIG. 20 (upper panel) shows that the commercially available *E. coli* translation extract contains significant protease activity. Such activity in only weakly inhibited by Chymostatin (FIG. 20, Bottom). On the other hand, significant inhibition is achieved with aprotinin (FIG. 20, middle). The results presented here clearly demonstrate that both the RRL system and the *E. coli* system have protease at a level that is capable of rapidly degrading picomolar amounts of short peptides so as to complicate mass spec detection. Such proteolysis activities present in the translation extracts can be significantly inhibited by pre-treating translation reaction mixtures with particular protease inhibitors.

Example 19

Inhibiting Proteolysis in Reconstituted Systems

All conventional translation systems tested (rabbit reticulocyte lysate, wheat germ extract, *E. coli* S30 extract) exhibited strong proteolytic activity that results in a complete degradation of sub-nanomolar amounts of R6 peptide within several minutes after incubation with the translation mixtures. On the other hand, the reconstituted system ("PURE") demonstrates a more specific proteolysis, leading to the accumulation of a dominant truncated product (MDYKDDDDKRRRRR)(SEQ ID NO:153). In this example, inhibition of proteolysis in the reconstituted systems (PURE I and II) is explored in more depth.

A number of protease inhibitor products are available commercially including Complete™ tablets (Roche), Protease Inhibitor Cocktail (Sigma) and BioStab general proteolysis inhibitor (Fluka). These are mixtures of individual compounds with known inhibitory activity against serine, cysteine and metalloproteases. For the BioStab inhibitor the composition and mechanism of inhibition are not described. The intended application for these products is prevention of protein degradation during purification from the whole cell lysates. Neither these products nor the individual protease inhibitors have been previously described as suitable for application in the in-vitro translation systems. There are a number of reasons for this. First, the proteolytic activity in in-vitro translation systems, especially in the purified systems, such as PURE, is expected to be significantly different from those in the whole cell lysates. Second, and more important, is that some of the individual components in the currently available protease inhibitor mixtures also inhibit the protein synthesis. For example, EDTA acts as an ion chelator and causes depletion of $Mg^{2+}$, which is required for the transcription. Furthermore, protease inhibitor cocktails often require DMSO as a solvent, which is not compatible with the transcription/translation reactions. Therefore, the objective of this work was to find a set of compounds that prevent proteolytic degradation of in-vitro produced polypeptides but do not interfere with the transcription and translation mechanisms. The R6 peptide was chosen because it possesses recognition sites for several types of proteases including very common trypsin and chymotrypsin.

The proteolysis in reconstituted *E. coli* translation systems (PURE I and PURE II, Post-Genome Institute, Japan) was assayed as follows: 10 µL of the translation reaction containing all components except the DNA was mixed with 1 µL of the R6 solution (10 pmol/µL) and incubated for 15 min at 37° C. 100 µL of the wash solution (1×PBS, 250 mM EDTA, 0.1% Triton) was added and applied to a microcolumn loaded with 1 µL of the anti-FLAG agarose beads (Sigma). The solution was allowed to pass through the beads (approx. 5 min) and the beads were washed with the wash solution and then 100 µL of dI $H_2O$. The peptide was eluted with the MALDI matrix (10 mg/mL α-hydroxycinnamic acid, 70% acetonitrile, 0.3% trifluoroacetic acid) solution directly onto a MALDI plate and analyzed by mass-spectrometry. To inhibit proteolysis in the reconstituted system, the assay was similar except that 1 µL of a protease inhibitor solution was added to the translation mixture and incubated for 15-30 min prior to the addition of the R6 peptide. More than 30 individual protease inhibitors (as well as combinations) were tested, including the following compounds, which are inhibitors of serine, cysteine, acid and metalloproteases as well as broad range inhibitors: α-macroglobulin, ebelactone B, bestatin, 6-aminohexanoic acid, phosphoramidon, EDTA, E-64, aprotinin, α-BOC deacetylleupeptin, AEBSF (Pefabloc™), ecotin, pepstatin, leupeptin, antipain, chymostatin, benzamidine HCl.

FIG. 21 (top trace) shows the disappearance of the intact R6 peptide with the molecular weight of 2522 Da and appearance of the truncated product (MDYKDDDDKRRRRR) (SEQ ID NO:153) with the molecular weight of 1925 Da after 15 min incubation with PURE I mixture. On the other hand, the inhibitor AEBSF showed excellent inhibition. FIG. 22 shows very similar effect observed in the PURE II system with (bottom) and without (top) the AEBSF inhibitor. The vast majority of compounds tested in the Pure II system were not effective, with the exception of AEBSF and aprotinin (FIG. 23). However, aprotinin was subsequently determined to inhibit protein synthesis. AEBSF could also inhibit protein synthesis if used (as the manufacturer suggests) together with "Pefabloc protector." Therefore, in the experiments described in this example, this "protector" was not used. Unlike the reconstituted *E. coli* results described above, inhibiting the proteases in RR extracts could not be done with a single compound to a degree necessary for mass spec analysis (see FIGS. 24 and 25). Various combinations were tested and several promising ones have been identified. In the data shown in FIG. 26 (lower trace), the combination included antipain (stock concentration 20 mg/mL), aprotinin (1 mg/mL), calpastatin (1 mg/mL) and α-BOC deacetylleupeptin (5 mg/mL). 2 µL of the above protease inhibitor solution was added to 10 µL of the translation mixture. Other combinations were tested (FIG. 27) and they were either less effective (compare top panel to bottom panel) or completely ineffective (middle three panels).

Example 20

Removing Proteases from Reconstituted Systems

Another approach to the protease problem is to remove proteases from translation systems. The PURE kit purchased from the Post-Genome Institute contains two components: Solution A and Solution B, the contents of which are not disclosed. The combined contents of these 2 Components comprise all elements needed to do in vitro transcription and translation from a PCR product including ribosomes, translation factors, an energy source, T7 polymerase, and ribonucleotides. When 1 ul of solutions A and B are analyzed by 1% agarose gel electrophoresis and stained with ethidium bromide, solution B shows a staining pattern that resembles that obtained from ribosomes, while solution A does not. Analysis of solutions A and B using the mass spec-based protease assay (with R6 as described above) demonstrate that solution A has no protease activity, while solution B has a protease that completely degrades the R6 test peptide by removing 4 residues from the C terminus. Thus, solution B contains ribosomes, contaminating proteases and perhaps other essential factors required for in vitro translation.

In order to remove the protease activity from solution B, 100 ul of solution B was added to 200 ul of deionized water and spun through a YM100 Microcon filter with a 100 kDa cut-off (Millipore, Inc) at 10,000 rpm for 5 minutes in a benchtop microfuge at room temperature. The R6 mass spec-based protease assay showed that the filtrate greatly reduced protease activity. However, when 3 ul of solution B filtrate was added to 7 ul of solution A, the resulting mixture was unable to generate a peptide from a PCR product template. By contrast, when 10 picomoles of zonally purified E. coli ribosomes (shown to be devoid of protease activity using the R6 assay) in 1 ul of water are added to this mixture, translation does take place. 10 picomoles of zonally purified E. coli ribosomes added to solution A without any solution B filtrate does not allow translation. Thus, solution B contains ribosomes but the filtrate does not, while the filtrate does contain other essential factors for translation. The new translation mixture (hence forth referred to as Amber-PURE) can be dispensed in 10 ul aliquots and frozen at −70 degrees for later use. A 10 ul aliquot contains 3 ul of diluted and filtered solution B, 7 ul of solution A and 10 picomoles of zonally purified ribosomes.

Example 21

Using Reconstituted Systems Depleted of Proteases

The previous example illustrates that one approach to the protease problem of reconstituted systems is to remove proteases from translation systems. In this example, the protease-depleted system is used to produce the reference peptide (R6) by in vitro translation using DNA coding for the R6 peptide. Template for the reaction consists of a PCR product encoding the R6 peptide that is made by filling in overlapping oligonucleotides of the following sequence:

```
Forward:
TAATACGACTCACTATAGGGAGGAGGACAGCTATGGACTACAAGGACGACG    (SEQ ID NO: 154)

ATGACAAGAGGAGGAGGAGGAGGAGGT

Reverse:
CAAAAAACCCCTCAAGACCCGTTTAGAGGCCCCAAGGGGTTATGCTAGTCAG  (SEQ ID NO: 155)

AAGAAGAACCTCCTCCTCCTCCTCTT
```

Addition of 1 ul of the PCR product to either 10 ul of PURE or 10 ul of Amber-PURE followed by incubation at 37 degrees for 20 minutes results in the generation of the R6 test peptide (the predicted mass of formylated R6 is 2,553 Da). Most of the peptide products obtained from PURE are smaller than the parent peptide and correspond to degradation products (FIG. 28A). This shows that the commercially available reconstituted system as it is sold is not suitable for in vitro translation of polypeptides that are detected using a sensitive assay such as the mass spec-based assay described herein. In contrast, most of the peptide product obtained from the Amber-PURE is the intact patent peptide and not degradation products (FIG. 28B). Thus, a protease-depleted reconstituted system can be used for in vitro translation of polypeptides where detection is by mass spec.

Amber-PURE can also be used to produce peptides for genetic testing purposes. For example, using the Amber-PURE system, the mass spectra of a peptide encoded by a 210 base pair test sequence of the APC gene shows the wild type peptide as well as mutants. More specifically, codons 1299-1368 (70 codons containing 210 bases) of the APC gene were amplified with the following primers:

```
Forward:
TAATACGACTCACTATAGGGAGGAGGACAGCTATGGACTACAAGGACGACG    (SEQ ID NO: 156)

ATGACAAGACGACACAGGAAGCAGATTCT

Reverse:
TTTTTATGCGTAGTCTGGTACGTCGTATGGGTAGTGTTCAGGTGGACTTTTGGG (SEQ ID NO: 157)
```

The forward primer contains a T7 polymerase binding sequence and sequence encoding the FLAG epitope that is used for purification purposes. The reverse primer encodes an HA epitope tag and provides a stop codon. An additional reverse primer was used to encode a peptide having a His-Gly amino acid substitution:

```
Reverse His > Gly:
TTTTTATGCGTAGTCTGGTACGTCGTATGGGTAGCCTTCAGGTGGACTTTTGGG (SEQ ID NO: 158)
```

These primers were used to amplify genomic DNA having the wildtype APC gene, or genomic DNA taken from tumor cell lines having truncating mutations in the APC gene. The peptides encoded by the PCR products have the following sequences and masses:

```
Wildtype (Mass 11,037):                                              (SEQ ID NO: 159)
MDYKDDDDKTTQEADSANTLQIAEIKEKIGTRSAEDPVSEVPAVSQHPRTKSSRL

QGSSLSSESARHKAVEFSSGAKSPSKSGAQTPKSPPEHYPYDVPDYA
```

Mutant codon 1309 Del 5 (Mass 3,404 with formyl group at N terminus):

```
MDYKDDDDKTTQEADSANTLQIAEIKDWN       (SEQ ID NO: 160)
```

Mutant codon 1338 CAG>TAG (Mass 6,134 with formyl group at N terminus):

```
MDYKDDDDKTTQEADSANTLQIAEIKEKIGTRSAEDPVSEVPAVSQHPRTKSSRL  (SEQ ID NO: 161)

Mutant codon 1367 CAG > TAG (Mass 8,981 with formyl
group
at N terminus):
MDYKDDDDKTTQEADSANTLQIAEIKEKIGTRSAEDPVSEVPAVSQHPRTKSSRL  (SEQ ID NO: 162)

QGSSLSSESARHKAVEFSSGAKSPSKSGA
```

Point mutation His(1374)>Gly(1374)(WT Mass 10,987 with formyl group at N terminus):

```
MDYKDDDDKTTQEADSANTLQIAEIKEKIGTRSAEDPVSEVPAVSQHPRTKSSRL  (SEQ ID NO: 163)

QGSSLSSESARHKAVEFSSGAKSPSKSGAQTPKSPPEGYPYDVPDYA
```

1 microliter of PCR product was added to 10 ul of AmberPURE and incubated 20 minutes at 37 degrees. Synthesis was stopped by addition of 100 ul of a solution containing 1% Triton-X 100 and 100 mM ammonium bicarbonate (Tx100/ABC). This solution was then purified on a microcolumn containing 1 ul of M2 anti-FLAG antibody coated sepharose beads and washed with 100 ul Tx100/ABC and 100 ul distilled water. The bound peptides were released with 1 ul of maldi matrix (10 mg/ml sinapinic acid, 0.1% TFA, 50% acetonitrile) directly onto a maldi plate and analyzed with a Voyager DE-Pro Maldi-Tof mass spectrometer. The results (data not shows) reveal the dominant peak for each spectrum has the expected mass of the encoded peptide; mutant peaks are easily distinguished from the wildtype signal (even when the wild-type to mutant PCR template ratio is 4 to 1).

Example 22

Depleting Wild-Type Polypeptides

Detection of a mutant sequence is often complicated by the presence of large amounts of the wild-type sequence. For example, human APC genes isolated from stool samples will contain mostly the wild-type sequence even if the patient has a polyp containing a mutant version of the APC gene. Mass spectra of APC peptides made in vitro from stool sample DNA from such a patient will show a dominant wild-type signal that can make detection of the truncated species difficult. Since the wild-type peptide has an intact C-terminus and the mutant does not, it is possible to deplete the wildtype peptides using an antibody against the C-terminal epitope (e.g. the HA epitope) present in the C-terminus.

This approach has been documented for a region of the APC gene containing codons 1299-1317. The mutant truncated peptide was made from a sequence having the codon 1309 Del mutation (see Example 21, above). The formylated wildtype peptide has a mass of 5,769 Da, while the mutant truncated peptide has mass of 3,404 Da. When the wild-type sequence (FIG. 29A) or the truncated peptide (FIG. 29B) are made alone, the peaks are quite evident. However, when the two are made together and the template ratio is 1:256 (mutant: wild-type), the truncated peak is not readily detected (FIG. 29C). On the other hand, if the peptide mixture, after peptide synthesis, is run over an anti-HA microcolumn containing 5 ul of anti-HA agarose beads (Sigma, St Louis, Mo.), thereby depleting wild-type polypeptide sequences by binding to the C-terminal epitope, the truncated sequence is readily detected (FIG. 29D) even when starting with a template ratio of 1:256 (mutant:wild-type). The results show detection is readily achieved under conditions where the depletion process is incomplete and there is considerable wild-type sequence remaining (indeed, from the peak heights one can estimate that the wild-type polypeptides are present in a ratio of at least 10:1 vis-à-vis the truncated peptide). Of course, more complete depletion protocols (e.g. optimizing affinity chromatography conditions by a) using a larger column, b) utilizing a higher affinity ligand:epitope system, or c) adjusting flow rates, etc.) can be employed to further enhance sensitivity.

Example 23

Temperature Effects

As discussed above, it is possible that mRNA secondary structure interferes with efficient cell-free protein expression yields. One approach to this problem is to increase the temperature of the translation reaction from 37° C. to between 39° C. and 45° C. more preferably to approximately 42° C. or 43° C. In order to check the effect of temperature on cell-free translation, the translation reaction was carried out in this example at various temperatures. The cell-free reaction mixture contained 7 µl of PURESYSTEM classic II translation system (Post Genome Institute Co, Japan) and 1 µL of DNA (approximately 200 ng). The translation reaction was allowed to proceed for 45 mm at the indicated temperatures. After the incubation, the reaction was terminated by addition of 100 µL of wash solution containing 100 mM EDTA, 1×PBS (phosphate buffered saline) and 0.1% Triton X-100 and immediately applied to the microcolumn containing 1 µl of packed beads (EZview™ Red ANTI-FLAG® M2 Affinity Gel; Sigma, St. Louis). The beads were then washed with 50 µL of wash solution followed by 50 µL of deionized H$_2$O and the bound peptide was eluted with ~2 µl of matrix solution (20 mg/mL sinapinic acid, 50% acetonitrile, 0.3% TFA) directly onto a MALDI plate. In a control experiment, translation was carried out without any added DNA (PCR product) and was processed as described above. The results of temperature dependence are shown in FIGS. 30A and 30B. When the translation was carried out using the 2 different APC PCR amplicons (APC-58 and APC-60) at two different temperatures (37° C. and 42° C.), predominant peaks corresponding to the expected molecular weight of WT fragments were observed and the overall intensity of the peaks and signal to noise ratio were much higher at 42° C. than 37° C., measured under identical conditions, indicating the increase in translation yield at higher temperature. Similarly, increasing the temperature beyond 45° C.; significantly decreased the yield of translation reaction (FIG. 30C).

Example 24

Primer Design

As mentioned above, in one embodiment, primers are designed to avoid undesirable folding. In this example, optimization of primers in order to avoid mRNA structure in ribosome binding site and stop codon. Without limiting the present invention to any particular mechanism, by introducing silent substitutions in the 5' and 3' primers it is believed that undesirable base paring can be avoided. In order to check the effect of mRNA structure on cell-free translation, PCR amplicons were made using two different 5'-end primers. Various primers were designed by introducing silent substitutions in the 5' and 3' primers in order to avoid undesirable base paring. For example, in one experiment two different forward primers were used in PCR amplification of segment S6 (see FIG. 31A) and their influence on the translation yield was measured. The forward primers 1 and 2 Contained several different nucleotides both in the 5'-UTR and in the FLAG tag sequence immediately downstream of the initiation codon. The cell-free reaction mixture contained 7 µl of PURESYSTEM classic II translation system (Post Genome Institute Co, Japan) and 1 µl of DNA (approximately 200 ng). The translation reaction was allowed to proceed for 45 min at 42° C. After the incubation, the reaction was terminated by addition of 100 µL of wash solution containing 100 mM EDTA, 1×PBS (phosphate buffered saline) and 0.1% Triton-X100 and immediately applied to the microcolumn containing 1 µL of packed beads (EZview™ Red ANTI-FLAG® M2 Affinity Gel; Sigma, St. Louis). The beads were then washed with 50 µL of wash solution followed by 50 µL of deionized H$_2$O and the bound peptide was eluted with ~2 µL of matrix solution (20 mg/mL sinapinic acid, 50% acetonitrile, 0.3% TFA) directly onto a MALDI plate. In a control experiment, translation was carried out without any added DNA (PCR product) and was processed as described above.

The mRNA structure of S6 segments encoded by the two primers was predicted by the program Mfold (Zuker, M., Mfold web server for nucleic acid folding and hybridization prediction. Nucleic Acids Res, 2003, 31(13), 3406-3415) to have considerably different folding patterns with regards to which will have a hair pin loop and which will have bubble like structures (FIGS. 31A and 31B). The results indicated a much higher yield in the case of forward primer 1 when measured by both mass-spectrometry (FIG. 31C) and ELISA assay (FIG. 31D).

Example 25

Additives

As mentioned previously, in one embodiment, the present invention contemplates adding components to the translation reaction to avoid or at least reduce secondary structure problems. In this example, in order to check the effect of mRNA structure destabilizers, the translation was carried in presence and absence of several reagents. These included MgCl$_2$ in the millimolar range and betaine (trimethylglycine) in the submolar range which we have shown do not interfere significantly with protein expression. For example, in one experiment, the translation reaction was supplemented with 5 mM magnesium ions by adding magnesium chloride. The cell-free reaction mixture contained 7 µl of PURESYSTEM classic II translation system (Post Genome Institute Co, Japan) and 1 µl of DNA (approximately 200 ng). The translation reaction was allowed to proceed for 45 min at 42° C. After the incubation, the reaction was terminated by addition of 100 µL of wash solution containing 100 mM EDTA, 1×PBS (phosphate buffered saline) and 0.1% Triton-X100 and immediately applied to the microcolumn containing 1 µL of packed beads (EZview™ Red ANTI-FLAG® M2 Affinity Gel; Sigma, St. Louis). The beads were then washed with 50 µL of wash solution followed by 50 µL of deionized $H_2O$ and the bound peptide was eluted with ~2 µL of matrix solution (20 mg/mL sinapinic acid, 50% acetonitrile, 0.3% TFA) directly onto a MALDI plate. The results shown in FIG. 32 indicated much higher yield was obtained in presence of 5 mM added magnesium.

Example 26

Removal of Full-Length Peptides

In order to increase the sensitivity of the mass spec assay to detect small levels of chain truncating mutants, depletion assay was developed. This approach involves enriching the mutant fraction via (at least partial) depletion of the full-length (e.g. non-truncating) peptides. In one experiment, removal of most of the full-length peptide by capturing the fragment using a C-terminal epitope (HA) was employed. The results of such depletion experiments are shown in FIG. 33. It can be seen from FIG. 33 that mutant can be enrich by removal of full length WT polypeptides from the mixture prior to Mass spectrometry. In addition, this epitope tag provides additional mass separation of at least 1102 Da between the wild-type and mutant signals, which results in enhanced spectral detection of mutant peptides.

Example 27

Alternative Reading Frame (ARF) Stop Codon Design

It is possible for a frame shifting mutation to lead to loss of the in-frame primer encoded stop codon resulting in an in vitro expressed polypeptide which is actually longer than the WT polypeptide. In order to avoid this problem, we have invented the ARF stop codon which is encoded through the reverse primer. This primer contains three codons TTT ATT TAT complementary to ATA AAT AAA in the 5'→3' sequences, which encode Ile-Asn-Lys (the "INK" sequence). The INK sequence contains termination codon TAA in two alternative reading frames. The presence of these extra codons guarantees that any frame-shift mutation within the test sequence results in a premature termination of the peptide synthesis.

Example 28

Yields Measured by ELISA

The basis of the measurement is to capture the produced polypeptide fragments on an ELISA plate using the N-terminal flag epitope using an immobilized anti-flag antibody. The amount of peptide captured is then measured using the C-terminal HA epitope using an antibody directed against HA. The actual amount of peptide produced is then determined by comparing the chemiluminescent signal to a calibration curve derived using FLAG-HA (MDYKDDDDKNFPFF-FETLKLSSRVYPYDVPDYA), a test synthetic model peptide, having FLAG-epitope sequence at N-terminal and HA at C-terminal. In one experiment, this peptide was serially diluted 25-fold to 200-fold (i.e. 25×, 37.5×, 5×, 75×, 100×, 150×, 200×). A 96-well ELISA plate (Thermoelectron, Lab-systems Products, Franklin, Mass.) was coated with 250 ng/mL anti-Flag-M2 antibody (Sigma, St. Louis, Mo.). After binding, the plate was washed three times with TBS-T (TBS with 0.05% Tween 20) followed by two washes with TBS and developed using a chemiluminescent HRP substrate (Supersignal Femto, Pierce, Rockford, Ill.). The results, shown in FIG. 34, indicate the linearity between amounts of peptide captured in a well verses chemiluminescent signal. From this signal, the amount of nascent peptide produced in the MASSIVE-PRO assay can be calculated.

Example 29

Detection of a 1% Mutant Population

It has been estimated that 1% mutant copies relative to WT are likely to be present in patients (and perhaps less than 1%) with CRC or large adenomas that are likely to transform into neoplastic polyps (Kinzler, K. W. and B. Vogelstein, Cancer-susceptibility genes. Gatekeepers and caretakers. Nature, 1997, 386(6627), 761-763). In order to test the feasibility of high sensitivity mutation detection using MASSIVE-PRO, we initially analyzed various mixtures of WT and mutant APC DNA obtained from cell lines. In this example, codons 1301-1331 of the APC gene were utilized as a test sequence (90 bases excluding primer sequences). The PCR products obtained from the WT and mutant cell-line DNA were mixed in various ratios (100:0 (100%) to 100:1 (1%)) and used for cell-free translation in the PURE system. After the translation, nascent peptides were purified by capture using the N-terminal FLAG-epitope. Our results (FIG. 35) show clearly that MASSIVE-PRO can unambiguously detect a 1% mutant population.

Example 30

Design of a Primer without the Stop Codon

In order to increase the sensitivity of the mass spec assay to detect small levels of chain truncating mutants, a WT translation suppression assay was developed. While not limiting the present invention to any particular mechanism, it is believed that this approach involves enriching the mutant fraction by (at least partially) arresting the full length mRNA/polypeptides on the ribosomes during the translation. In this example, arrest of most of the full-length polypeptide on ribosome was achieved using the amplicons without the stop codon at 3'-end. Since the amplicon does not contain stop codon the mRNA/polypeptide complex is not efficiently released from the polyribosome complex. The results of such translation suppression methodology are shown in FIG. 36. It can be seen from the comparison of FIG. 36 with FIG. 35 that the signal from the mutant can be enriched by (putatively) arresting the full-length polypeptide on the ribosome relative to the wild-type signal.

Example 31

Multiplexing

An important advantage of Mass spectrometry is the ability to analyze simultaneously the mass of multiple polypeptides. In the context of the present invention, this can be an important advantage, since multiplex detection of several WT segments and simultaneous scanning for possible mutations can lower time and cost of ultimate CRC assay. We have performed several experiments using 2 different APC segments; importantly, these were translated in a single cell-free reaction. It is important to note that one segment was derived from a heterozygous cell line containing a mutation in that segment. After the translation, nascent peptides were co-purified using a FLAG-antibody capture and analyzed by mass spectrometry. The results of one such experiment is shown in FIG. 37. The top two traces show mass spectra recorded of the individual WT APC S4 (middle trace) and the WT APC S8 with its chain-truncating mutant at codon 1450 (top trace). The two APC segments plus the mutant all exhibit the expected masses calculated from the nucleotide sequences. Importantly, all three bands can also be detected in the multiplexed reaction and measurement, demonstrating the feasibility of at least performing 2-fold multiplexing.

Example 32

Reducing Background

Preliminary studies indicate that as yet unidentified impurities introduced onto the MALDI substrate produce a relatively constant background in the mass spectra. While efforts can be pursued as described above to reduce such impurities, it is possible to enhance the ability to detect authentic mutant peaks by removing this constant background. For this purpose, special software is utilized to analyze the data and detect new peaks in the mass spectra. Such software is already commercially available for proteomics research (for example ClinProTools software for biomarker detection and evaluation from Bruker Daltonics). Our initial studies have revealed that there exists a constant background in typical MASSIVE-PRO spectra which survives purification steps discussed above. We have been able to successful remove much of this background by utilizing standard spectral subtraction software, thus allowing small mutant peaks to be detected (FIG. 38).

Example 33

Fecal and Urine DNA

In this example, we demonstrate the feasibility of using fecal DNA for mass spec analysis. In this case, the fecal DNA was isolated using standard Qiagen method. PCR products were first obtained using DNA isolated from 100 mg of stool samples (volunteer DNA: healthy subject). Polypeptides coded for by specific regions of the APC gene were translated using a reconstituted PURE cell-free translation system. The translated products were captured using anti-FLAG antibody beads directed against the N-terminal FLAG-epitope incorporated into the nascent polypeptide. Unbound material is extensively washed from the beads. The nascent polypeptide(s) were then eluted using matrix solution (acetonitrile-TFA-sinapinic acid) and analyzed by MALDI-MS. Two different regions of the APC gene approximately 33 amino acids in length, designated S1 and S4), were chosen for analysis using both cell-line and fecal DNA (see FIG. 39A caption). As seen in FIG. 39A, both sources of DNA yield almost identical mass spectral results. In particular, the wild type peaks appear at mass 7274 and 7520 Da for both sources of DNA.

In addition to stool DNA, APC MASSIVE-PRO was performed on the DNA isolated from urine. As seen in FIG. 39B, both sources of DNA (urine and human genomic DNA) yield almost identical mass spectral results. In particular, the wild type peak appears at mass 6412 Da for both sources of DNA.

In addition, we have performed APC MASSIVE-PRO on the DNA isolated from stool obtained from healthy volunteers as well as colorectal cancer (CRC) patients. As seen in FIG. 39C, one of the CRC patients shows an additional peak which corresponds to the Δ5 mutation at codon 1309 in APC gene.

Example 34

P53 Mutation Detection

To demonstrate the feasibility of detecting mutations in the P53 gene by mass spec, we have carried out PCR corresponding to Exon 5, 7 and 8 (where most of the mutations are clustered) using DNA isolated from cell-lines with defined mutations. The PCR product was then translated in an *E. Coli* PURE system (PGI, Japan). The translated products were captured using anti-FLAG antibody beads (since the FLAG-epitope was incorporated during the PCR at N-terminal) and the unbound material extensively washed. The eluted protein fragment(s) were then eluted using matrix solution (acetonitrile-TFA-matrix) and analyzed by MALDI-MS. The result of one such experiment is shown is FIG. 40. The top spectrum corresponds to wild-type P53 and bottom spectrum to a mutant where codon 175 has been altered (CGC→CAC) resulting in amino acid substitution R→H.

Example 35

Polyp DNA

In this example, we demonstrate the feasibility of using polyps DNA for MASSIVE-PRO analysis. In this case, the DNA was isolated from two polyp samples (normal and mutant) using standard Qiagen method. PCR products were first obtained using DNA isolated from several 10 micron sections of polyps tissue blocks. Polypeptides coded for by specific regions of the APC gene were translated using a reconstituted PURE cell-free translation system. The translated products were captured using anti-FLAG antibody beads directed against the N-terminal FLAG-epitope incorporated into the nascent polypeptide. Unbound material is extensively washed from the beads. The nascent polypeptide(s) were then eluted using matrix solution (acetonitrile-TFA-sinapinic acid) and analyzed by MALDI-MS. As seen in FIG. 41, the normal sample P2-1 show the single peak with predicted mass of 7385 Da. While mutant sample P2-2 show two peaks (one for WT allele at 7385 Da and other for mutant allele at 4496 Da) indicating that the sample P2-2 has CGA->TGA mutation at codon 1450 in APC gene which gives the truncated product of predicted mass of 4496 Da.

Example 36

K-RAS Mutation Detection

In this example, in order to demonstrate the feasibility of detecting mutations in the K-RAS gene by mass spec, we have carried out PCR corresponding to the first 30 codons of K-RAS gene (where most of the mutations are clustered) using human genomic DNA as well as DNA isolated from human stool and urine samples. The two primers were as follows:

```
K-Ras-MP5:
5'-TAATACGACTCACTATA GGGAGAGGAGGTATATCA ATG GAT
TAT AAA GAC GAT GAT GAT AAA ACT GAA TAT AAA CTT
GTG GTA-3'
and K-Ras-MP3:
5'-TTA GTC CAC AAA ATG ATT CTG AAT-3'
```

The PCR product was then translated in an *E. Coli* PURE system (PGI, Japan). The translated products were captured using anti-FLAG antibody beads (since the FLAG-epitope was incorporated during the PCR at N-terrninal) and the unbound material extensively washed. The eluted protein fragment(s) were then eluted using matrix solution (acetonitrile-TFA-matrix) and analyzed by MALDI-MS. As seen in FIG. 42, the DNA obtained from all the sources (genomic, stool and urine) yield almost identical mass spectral results. In particular, in all the samples, the wild type peak appears at mass 4212 Da.

Example 37

Filtering the Translation Mix

Our preliminary studies indicate that the filtration of translation mix using YM-100 membrane filters (Millipore, Mass.) prior to FLAG purification, which removes the ribosome fraction, significantly improves the background. These background peaks are due to incomplete translation products since these peptides remain bound to the ribosomes. Ribosome removal was performed by: (1) mixing the translation reaction with 10× volume of ice-cold 50 mM Tris-acetate, 10 mM MgCl2 pH 7.5 solution immediately after the reaction completion; (2) applying the resulting solution on a pre-chilled Microcon YM-100 filter (Millipore, 100 kDa MWCO); (3) centrifugation at 14,000 rpm for 5 to 10 minutes and (4) collecting the pass-through. This pass through is then subjected to FLAG-purification and MASSIVE-PRO.

FIG. 43 shows mass-spectrum of anti-FLAG-purified segment APC-61 before (top trace) and after (bottom trace) ribosome removal by YM-100 filtration. These results indicate that the ribosome removal procedure results in significant reduction of peaks arising from the incompletely translated peptides (inset, peaks marked *) and also from the components of the translation mixture itself (peaks in the 8000-16000 Da region, marked **).

Example 38

Assaying Over 80% of CRC-Associated Mutations

Detailed analysis of the latest APC mutation database compiled by Dr. Soussi for sporadic colorectal cancer indicates that exon 15 alone contains more than 95% of the total mutations associated with CRC (FIG. 44). In particular, out of 842 total cases of sporadic CRC reported, only 38 Cases (4.2%) were found in exons 1-14. In addition, only 4 mutations (out of 842) were mis-sense (i. e. non-chain truncation); the remaining cases (838) were all mutations resulting in chain truncation. Thus, scanning exon 15 should pickup approximately 95% of the mutations that occur for sporadic CRC. A more restricted region within Exon 15 is the so-called mutation cluster region (MCR) which contains approximately 83% of all the mutations associated with CRC. This region was the focus of an earlier study utilizing digital PTT. Traverso et al., *N. Engl J Med.* 346:311-320 (2002). However, unlike MASSIVE-PRO, this method requires over 144 individual PCR and cell-free protein expression reactions per scanned segment to achieve 1% sensitivity.

In one embodiment, the present invention contemplates 12 primer sets designed to amplify specific sequences (called segments) of the cell-line APC gene (S1-S12; FIG. 44) using the DNA (e.g. isolated from fecal material, urine, polyps, etc.). It is not intended that the present invention be limited to the precise primers or primer sets. However, Table 4 provides 12 illustrative 5'-primers and Table 5 provides 12 illustrative 3'-primers. Together, these primers permit coverage of the MCR region.

While these 12 sets may be optimal for cell-lines, the integrity of fecal DNA can affect the ability to perform PCR-amplification over regions this large. Therefore, in another embodiment, the same region could be covered with 30 or fewer primers sets, more preferably 20 or fewer primer sets.

Other embodiments and uses of the invention will be apparent to those skilled in the art from consideration of the specification and practice of the invention disclosed herein. It is intended that the specification and examples be considered exemplary only, with the scope of particular embodiments of the invention indicated by the following claims.

TABLE 1

Truncation Mutations In Human Molecular Genetics

| Disease References | % Truncating Mutations | Gene |
|---|---|---|
| Familial Adenomatous Polyposis | 95% | APC |
| Hereditary desmold disease | 100% | APC |
| Ataxia telangiectasia | 90% | ATM |
| Hereditary Breast and Ovarian Cancer | 90% | BRCA1 |
|  | 90% | BRCA2 |
| Cystic Fibrosis | 15% | CFTR |
| Duchenne Muscular Dystrophy | 95% | DMD |
| Emery-Dreifuss Muscular Dystrophy | 80% | EMD |
| Fanconi anaemia | 80% | FAA |
| Hunter Syndrome | 50% | IDS |
| Hereditary non-polyposis colorectal cancer | ~80% | hMSH2 |
|  | 70% | hMLH1 |
| Neurofibromatosis type 1 | 50% | NF1 |
| Neurofibromatosis type 2 | 65% | NF2 |
| Polycystic Kidney Disease | 95% | PKD1 |
| Rubinstein-Taybi Syndrome | 10% | RTS |

The percentage of truncating mutations reported which should be detectable using PTT.

The invention claimed is:

1. A method, comprising:
    a) providing:
        i) a nucleic acid sequence encoding a polypeptide, said polypeptide being between 10 and 150 amino acids in length; and
        ii) a reconstituted in vitro translation system comprising recombinant proteins, at least one protease inhibitor and isotopically-depleted amino acids;
    b) introducing said nucleic acid into said reconstituted translation system under conditions such that said polypeptide is produced, said polypeptide comprising isotopically-depleted amino acids; and
    c) determining the molecular mass of said polypeptide by mass spectrometry.

2. The method of claim 1, wherein said isotopically-depleted amino acids are $^{13}C$-depleted.

3. The method of claim 1, wherein said isotopically-depleted amino acids are $^{15}N$-depleted.

4. The method of claim 1, wherein said isotopically-depleted amino acids are $^{13}C$- and $^{15}N$-depleted.

5. A method, comprising:
    a) providing:
        i) a first nucleic acid sequence encoding a polypeptide comprising a wild-type sequence;
        ii) a second nucleic acid sequence encoding a truncated polypeptide of said wild-type sequence, said truncated polypeptide being 10 to 150 amino acids in length; and
        iii) a reconstituted in vitro translation system comprising recombinant proteins, at least one protease inhibitor and isotopically-depleted amino acids;
    b) introducing said first and second nucleic acid sequences into said reconstituted translation system under conditions such that said wild-type and truncated polypeptides are produced, said wild-type and truncated polypeptides comprising isotopically-depleted amino acids; and
    c) determining the molecular mass of said truncated polypeptide by mass spectrometry.

6. A method, comprising:
    a) providing:
        i) a nucleic acid sequence encoding a polypeptide, said polypeptide being between 10 and 150 amino acids in length; and
        ii) a reconstituted in vitro translation system lacking natural amino acids and comprising recombinant proteins, at least one protease inhibitor and isotopically-depleted amino acids;
    b) introducing said nucleic acid into said reconstituted translation system under conditions such that said polypeptide is produced, said polypeptide comprising isotopically-depleted amino acids; and
    c) determining the molecular mass of said polypeptide by mass spectrometry.

* * * * *

SEQUENCE LISTING

<160> NUMBER OF SEQ ID NOS: 167

<210> SEQ ID NO 1
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 1

Asp Tyr Lys Asp Asp Asp Asp Lys Arg Arg Arg Arg Arg Arg Arg
1               5                   10                  15

Arg

<210> SEQ ID NO 2
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 2

Asp Tyr Lys Asp Asp Asp Asp Lys Arg Arg Arg Arg Arg Arg Arg
1               5                   10                  15

Arg Phe Phe Phe
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 3

Asp Tyr Lys Asp Asp Asp Asp Lys Arg Arg Arg Arg Arg Arg Arg
1               5                   10                  15

Arg Tyr Tyr Tyr
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 4

Asp Tyr Lys Asp Asp Asp Asp Lys Arg Arg Arg Arg Arg Arg Arg
1               5                   10                  15

```
Arg Leu Leu Leu
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 5

Asp Tyr Lys Asp Asp Asp Asp Lys Arg Arg Arg Arg Arg Arg Arg
1               5                   10                  15

Arg Asp Asp Asp
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 6

Asp Tyr Lys Asp Asp Asp Asp Lys Arg Arg Arg Arg Arg Arg Arg
1               5                   10                  15

Arg Lys Lys Lys
            20

<210> SEQ ID NO 7
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 7

Met Asp Tyr Lys Asp Asp Asp Asp Lys Arg Arg Arg Arg Arg Arg
1               5                   10                  15

Arg Arg

<210> SEQ ID NO 8
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 8

Met Asp Tyr Lys Asp Asp Asp Asp Lys Arg Arg Arg Arg Arg Arg
1               5                   10                  15
```

Arg Arg Phe Phe Phe
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 9

Met Asp Tyr Lys Asp Asp Asp Asp Lys Arg Arg Arg Arg Arg Arg Arg
1               5                   10                  15

Arg Arg Tyr Tyr Tyr
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 10

Met Asp Tyr Lys Asp Asp Asp Asp Lys Arg Arg Arg Arg Arg Arg Arg
1               5                   10                  15

Arg Arg Leu Leu Leu
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 11

Met Asp Tyr Lys Asp Asp Asp Asp Lys Arg Arg Arg Arg Arg Arg Arg
1               5                   10                  15

Arg Arg Asp Asp Asp
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 12

Met Asp Tyr Lys Asp Asp Asp Asp Lys Arg Arg Arg Arg Arg Arg Arg

```
                 1               5                  10                 15
Arg Arg Lys Lys Lys
               20

<210> SEQ ID NO 13
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 13

Glu Gln Lys Leu Ile Ser Glu Glu Asp Leu Arg Arg Arg Arg Arg
1               5                  10                  15

Arg Arg Arg

<210> SEQ ID NO 14
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 14

Glu Gln Lys Leu Ile Ser Glu Glu Asp Leu Arg Arg Arg Arg Arg
1               5                  10                  15

Arg Arg Arg Phe Phe Phe
               20

<210> SEQ ID NO 15
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 15

Glu Gln Lys Leu Ile Ser Glu Glu Asp Leu Arg Arg Arg Arg Arg
1               5                  10                  15

Arg Arg Arg Tyr Tyr Tyr
               20

<210> SEQ ID NO 16
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 16

Glu Gln Lys Leu Ile Ser Glu Glu Asp Leu Arg Arg Arg Arg Arg Arg
```

```
                1               5                  10                 15

Arg Arg Arg Leu Leu Leu
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 17

Glu Gln Lys Leu Ile Ser Glu Glu Asp Leu Arg Arg Arg Arg Arg
1               5                  10                 15

Arg Arg Arg Asp Asp Asp
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 18

Glu Gln Lys Leu Ile Ser Glu Glu Asp Leu Arg Arg Arg Arg Arg
1               5                  10                 15

Arg Arg Arg Lys Lys Lys
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 19

Met Glu Gln Lys Leu Ile Ser Glu Glu Asp Leu Arg Arg Arg Arg
1               5                  10                 15

Arg Arg Arg Arg
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 20
```

-continued

Met Glu Gln Lys Leu Ile Ser Glu Glu Asp Leu Arg Arg Arg Arg
1               5                   10                  15

Arg Arg Arg Arg Phe Phe Phe
            20

<210> SEQ ID NO 21
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 21

Met Glu Gln Lys Leu Ile Ser Glu Glu Asp Leu Arg Arg Arg Arg
1               5                   10                  15

Arg Arg Arg Arg Tyr Tyr Tyr
            20

<210> SEQ ID NO 22
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 22

Met Glu Gln Lys Leu Ile Ser Glu Glu Asp Leu Arg Arg Arg Arg
1               5                   10                  15

Arg Arg Arg Arg Leu Leu Leu
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 23

Met Glu Gln Lys Leu Ile Ser Glu Glu Asp Leu Arg Arg Arg Arg
1               5                   10                  15

Arg Arg Arg Arg Asp Asp Asp
            20

<210> SEQ ID NO 24
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 24

```
Met Glu Gln Lys Leu Ile Ser Glu Glu Asp Leu Arg Arg Arg Arg
1               5                   10                  15

Arg Arg Arg Arg Lys Lys Lys
            20
```

<210> SEQ ID NO 25
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 25

```
Trp Ser His Pro Gln Phe Glu Lys Arg Arg Arg Arg Arg Arg Arg
1               5                   10                  15

Arg
```

<210> SEQ ID NO 26
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 26

```
Trp Ser His Pro Gln Phe Glu Lys Arg Arg Arg Arg Arg Arg Arg
1               5                   10                  15

Arg Phe Phe Phe
            20
```

<210> SEQ ID NO 27
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 27

```
Trp Ser His Pro Gln Phe Glu Lys Arg Arg Arg Arg Arg Arg Arg
1               5                   10                  15

Arg Tyr Tyr Tyr
            20
```

<210> SEQ ID NO 28
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 28

```
Trp Ser His Pro Gln Phe Glu Lys Arg Arg Arg Arg Arg Arg Arg
1               5                  10                  15

Arg Leu Leu Leu
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 29

Trp Ser His Pro Gln Phe Glu Lys Arg Arg Arg Arg Arg Arg Arg
1               5                  10                  15

Arg Asp Asp Asp
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(17)
<223> OTHER INFORMATION: Some arginines may be missing.

<400> SEQUENCE: 30

Trp Ser His Pro Gln Phe Glu Lys Arg Arg Arg Arg Arg Arg Arg
1               5                  10                  15

Arg Lys Lys Lys
            20

<210> SEQ ID NO 31
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 31

Met Trp Ser His Pro Gln Phe Glu Lys Arg Arg Arg Arg Arg Arg
1               5                  10                  15

Arg Arg

<210> SEQ ID NO 32
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 32
```

Met Trp Ser His Pro Gln Phe Glu Lys Arg Arg Arg Arg Arg Arg
1               5                   10                  15

Arg Arg Phe Phe Phe
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 33

Met Trp Ser His Pro Gln Phe Glu Lys Arg Arg Arg Arg Arg Arg
1               5                   10                  15

Arg Arg Tyr Tyr Tyr
            20

<210> SEQ ID NO 34
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 34

Met Trp Ser His Pro Gln Phe Glu Lys Arg Arg Arg Arg Arg Arg
1               5                   10                  15

Arg Arg Leu Leu Leu
            20

<210> SEQ ID NO 35
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 35

Met Trp Ser His Pro Gln Phe Glu Lys Arg Arg Arg Arg Arg Arg
1               5                   10                  15

Arg Arg Asp Asp Asp
            20

<210> SEQ ID NO 36
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

```
<400> SEQUENCE: 36

Met Trp Ser His Pro Gln Phe Glu Lys Arg Arg Arg Arg Arg Arg
1               5                   10                  15

Arg Arg Lys Lys Lys
            20

<210> SEQ ID NO 37
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.

<400> SEQUENCE: 37

Cys Ser Pro Phe Glu Val Gln Val Ser Pro Glu Ala Gly Ala Gln Lys
1               5                   10                  15

Arg Arg Arg Arg Arg Arg Arg Arg Arg
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.

<400> SEQUENCE: 38

Cys Ser Pro Phe Glu Val Gln Val Ser Pro Glu Ala Gly Ala Gln Lys
1               5                   10                  15

Arg Arg Arg Arg Arg Arg Arg Arg Arg Phe Phe
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.

<400> SEQUENCE: 39

Cys Ser Pro Phe Glu Val Gln Val Ser Pro Glu Ala Gly Ala Gln Lys
1               5                   10                  15

Arg Arg Arg Arg Arg Arg Arg Arg Arg Tyr Tyr Tyr
            20                  25

<210> SEQ ID NO 40
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.
```

<400> SEQUENCE: 40

Cys Ser Pro Phe Glu Val Gln Val Ser Pro Glu Ala Gly Ala Gln Lys
1               5                   10                  15

Arg Arg Arg Arg Arg Arg Arg Arg Arg Leu Leu Leu
            20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.

<400> SEQUENCE: 41

Cys Ser Pro Phe Glu Val Gln Val Ser Pro Glu Ala Gly Ala Gln Lys
1               5                   10                  15

Arg Arg Arg Arg Arg Arg Arg Arg Arg Asp Asp Asp
            20                  25

<210> SEQ ID NO 42
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(25)
<223> OTHER INFORMATION: Some arginines may be missing.

<400> SEQUENCE: 42

Cys Ser Pro Phe Glu Val Gln Val Ser Pro Glu Ala Gly Ala Gln Lys
1               5                   10                  15

Arg Arg Arg Arg Arg Arg Arg Arg Arg Lys Lys Lys
            20                  25

<210> SEQ ID NO 43
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(26)
<223> OTHER INFORMATION: Some arginines may be missing.

<400> SEQUENCE: 43

Met Cys Ser Pro Phe Glu Val Gln Val Ser Pro Glu Ala Gly Ala Gln
1               5                   10                  15

Lys Arg Arg Arg Arg Arg Arg Arg Arg Arg
            20                  25

<210> SEQ ID NO 44
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(26)

<223> OTHER INFORMATION: Some arginines may be missing.

<400> SEQUENCE: 44

Met Cys Ser Pro Phe Glu Val Gln Val Ser Pro Glu Ala Gly Ala Gln
1               5                   10                  15

Lys Arg Arg Arg Arg Arg Arg Arg Arg Phe Phe Phe
            20                  25

<210> SEQ ID NO 45
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(26)
<223> OTHER INFORMATION: Some arginines may be missing.

<400> SEQUENCE: 45

Met Cys Ser Pro Phe Glu Val Gln Val Ser Pro Glu Ala Gly Ala Gln
1               5                   10                  15

Lys Arg Arg Arg Arg Arg Arg Arg Arg Tyr Tyr Tyr
            20                  25

<210> SEQ ID NO 46
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(26)
<223> OTHER INFORMATION: Some arginines may be missing.

<400> SEQUENCE: 46

Met Cys Ser Pro Phe Glu Val Gln Val Ser Pro Glu Ala Gly Ala Gln
1               5                   10                  15

Lys Arg Arg Arg Arg Arg Arg Arg Arg Leu Leu Leu
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(26)
<223> OTHER INFORMATION: Some arginines may be missing.

<400> SEQUENCE: 47

Met Cys Ser Pro Phe Glu Val Gln Val Ser Pro Glu Ala Gly Ala Gln
1               5                   10                  15

Lys Arg Arg Arg Arg Arg Arg Arg Arg Asp Asp Asp
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE

```
<222> LOCATION: (18)..(26)
<223> OTHER INFORMATION: Some arginines may be missing.

<400> SEQUENCE: 48

Met Cys Ser Pro Phe Glu Val Gln Val Ser Pro Glu Ala Gly Ala Gln
1               5                   10                  15

Lys Arg Arg Arg Arg Arg Arg Arg Arg Lys Lys Lys
            20                  25

<210> SEQ ID NO 49
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 49

Met Ala Ser Met Thr Gly Gly Gln Gln Met Gly Arg Arg Arg Arg Arg
1               5                   10                  15

Arg Arg Arg Arg
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 50

Met Ala Ser Met Thr Gly Gly Gln Gln Met Gly Arg Arg Arg Arg Arg
1               5                   10                  15

Arg Arg Arg Arg Phe Phe Phe
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 51

Met Ala Ser Met Thr Gly Gly Gln Gln Met Gly Arg Arg Arg Arg Arg
1               5                   10                  15

Arg Arg Arg Arg Tyr Tyr Tyr
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (12)..(20)
<223> OTHER INFORMATION: Some arginines may be missing.

<400> SEQUENCE: 52

Met Ala Ser Met Thr Gly Gly Gln Gln Met Gly Arg Arg Arg Arg
1               5                   10                  15

Arg Arg Arg Arg Leu Leu Leu
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 53

Met Ala Ser Met Thr Gly Gly Gln Gln Met Gly Arg Arg Arg Arg
1               5                   10                  15

Arg Arg Arg Arg Asp Asp Asp
            20

<210> SEQ ID NO 54
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 54

Met Ala Ser Met Thr Gly Gly Gln Gln Met Gly Arg Arg Arg Arg
1               5                   10                  15

Arg Arg Arg Arg Lys Lys Lys
            20

<210> SEQ ID NO 55
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 55

Met Met Ala Ser Met Thr Gly Gly Gln Gln Met Gly Arg Arg Arg
1               5                   10                  15

Arg Arg Arg Arg Arg
            20

<210> SEQ ID NO 56
<211> LENGTH: 24
<212> TYPE: PRT
<213> ORGANISM: Artificial Sequence
<220> FEATURE:
<223> OTHER INFORMATION: Synthetic
```

-continued

```
<220> FEATURE:
<221> NAME/KEY: MISC_FEATURE
<222> LOCATION: (13)..(21)
<223> OTHER INFORMATION: Some arginines may be missing.

<400> SEQUENCE: 56

Met Met Ala Ser Met Thr Gly Gly Gln Gln Met Gly Arg Arg Arg Arg
1               5                   10                  15
Arg Arg Arg Arg Arg Phe Phe Phe
            20

<210> SEQ ID NO 57
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 57

Met Met Ala Ser Met Thr Gly Gly Gln Gln Met Gly Arg Arg Arg Arg
1               5                   10                  15
Arg Arg Arg Arg Arg Tyr Tyr Tyr
            20

<210> SEQ ID NO 58
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 58

Met Met Ala Ser Met Thr Gly Gly Gln Gln Met Gly Arg Arg Arg Arg
1               5                   10                  15
Arg Arg Arg Arg Arg Leu Leu Leu
            20

<210> SEQ ID NO 59
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 59

Met Met Ala Ser Met Thr Gly Gly Gln Gln Met Gly Arg Arg Arg Arg
1               5                   10                  15
Arg Arg Arg Arg Arg Asp Asp Asp
            20

<210> SEQ ID NO 60
<211> LENGTH: 24
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 60

Met Met Ala Ser Met Thr Gly Gly Gln Gln Met Gly Arg Arg Arg
1               5                   10                  15

Arg Arg Arg Arg Arg Lys Lys Lys
            20

<210> SEQ ID NO 61
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 61

Tyr Pro Tyr Asp Val Pro Asp Tyr Ala Arg Arg Arg Arg Arg Arg
1               5                   10                  15

Arg Arg

<210> SEQ ID NO 62
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 62

Tyr Pro Tyr Asp Val Pro Asp Tyr Ala Arg Arg Arg Arg Arg Arg
1               5                   10                  15

Arg Arg Phe Phe Phe
            20

<210> SEQ ID NO 63
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 63

Tyr Pro Tyr Asp Val Pro Asp Tyr Ala Arg Arg Arg Arg Arg Arg
1               5                   10                  15

Arg Arg Tyr Tyr Tyr
            20

<210> SEQ ID NO 64
<211> LENGTH: 21
<212> TYPE: PRT
<213> ORGANISM: Artificial Sequence
<220> FEATURE:
```

<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 64

Tyr Pro Tyr Asp Val Pro Asp Tyr Ala Arg Arg Arg Arg Arg Arg
1               5                   10                  15

Arg Arg Leu Leu Leu
            20

<210> SEQ ID NO 65
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 65

Tyr Pro Tyr Asp Val Pro Asp Tyr Ala Arg Arg Arg Arg Arg Arg
1               5                   10                  15

Arg Arg Asp Asp Asp
            20

<210> SEQ ID NO 66
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(18)
<223> OTHER INFORMATION: Some arginines may be missing.

<400> SEQUENCE: 66

Tyr Pro Tyr Asp Val Pro Asp Tyr Ala Arg Arg Arg Arg Arg Arg
1               5                   10                  15

Arg Arg Lys Lys Lys
            20

<210> SEQ ID NO 67
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 67

Met Tyr Pro Tyr Asp Val Pro Asp Tyr Ala Arg Arg Arg Arg Arg
1               5                   10                  15

Arg Arg Arg

<210> SEQ ID NO 68
<211> LENGTH: 22
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 68

Met Tyr Pro Tyr Asp Val Pro Asp Tyr Ala Arg Arg Arg Arg Arg
1               5                   10                  15

Arg Arg Arg Phe Phe Phe
            20

<210> SEQ ID NO 69
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 69

Met Tyr Pro Tyr Asp Val Pro Asp Tyr Ala Arg Arg Arg Arg Arg
1               5                   10                  15

Arg Arg Arg Tyr Tyr Tyr
            20

<210> SEQ ID NO 70
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 70

Met Tyr Pro Tyr Asp Val Pro Asp Tyr Ala Arg Arg Arg Arg Arg
1               5                   10                  15

Arg Arg Arg Leu Leu Leu
            20

<210> SEQ ID NO 71
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 71

Met Tyr Pro Tyr Asp Val Pro Asp Tyr Ala Arg Arg Arg Arg Arg
1               5                   10                  15

Arg Arg Arg Asp Asp Asp
            20

<210> SEQ ID NO 72
<211> LENGTH: 22
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (11)..(19)
<223> OTHER INFORMATION: Some arginines may be missing.

<400> SEQUENCE: 72

Met Tyr Pro Tyr Asp Val Pro Asp Tyr Ala Arg Arg Arg Arg Arg
1               5                   10                  15

Arg Arg Arg Lys Lys Lys
            20

<210> SEQ ID NO 73
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 73

Glu Asp Gln Val Asp Pro Arg Leu Ile Asp Gly Lys Arg Arg Arg
1               5                   10                  15

Arg Arg Arg Arg Arg Arg
            20

<210> SEQ ID NO 74
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 74

Glu Asp Gln Val Asp Pro Arg Leu Ile Asp Gly Lys Arg Arg Arg
1               5                   10                  15

Arg Arg Arg Arg Arg Phe Phe Phe
            20

<210> SEQ ID NO 75
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 75

Glu Asp Gln Val Asp Pro Arg Leu Ile Asp Gly Lys Arg Arg Arg
1               5                   10                  15

Arg Arg Arg Arg Arg Tyr Tyr Tyr
            20

<210> SEQ ID NO 76
<211> LENGTH: 24
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 76

Glu Asp Gln Val Asp Pro Arg Leu Ile Asp Gly Lys Arg Arg Arg Arg
1               5                   10                  15

Arg Arg Arg Arg Arg Leu Leu Leu
            20

<210> SEQ ID NO 77
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 77

Glu Asp Gln Val Asp Pro Arg Leu Ile Asp Gly Lys Arg Arg Arg Arg
1               5                   10                  15

Arg Arg Arg Arg Arg Asp Asp Asp
            20

<210> SEQ ID NO 78
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 78

Glu Asp Gln Val Asp Pro Arg Leu Ile Asp Gly Lys Arg Arg Arg Arg
1               5                   10                  15

Arg Arg Arg Arg Arg Lys Lys Lys
            20

<210> SEQ ID NO 79
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 79

Met Glu Asp Gln Val Asp Pro Arg Leu Ile Asp Gly Lys Arg Arg Arg
1               5                   10                  15

Arg Arg Arg Arg Arg Arg
            20

<210> SEQ ID NO 80
<211> LENGTH: 25
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 80

Met Glu Asp Gln Val Asp Pro Arg Leu Ile Asp Gly Lys Arg Arg Arg
1               5                   10                  15

Arg Arg Arg Arg Arg Arg Phe Phe Phe
            20                  25

<210> SEQ ID NO 81
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 81

Met Glu Asp Gln Val Asp Pro Arg Leu Ile Asp Gly Lys Arg Arg Arg
1               5                   10                  15

Arg Arg Arg Arg Arg Arg Tyr Tyr Tyr
            20                  25

<210> SEQ ID NO 82
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 82

Met Glu Asp Gln Val Asp Pro Arg Leu Ile Asp Gly Lys Arg Arg Arg
1               5                   10                  15

Arg Arg Arg Arg Arg Arg Leu Leu Leu
            20                  25

<210> SEQ ID NO 83
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 83

Met Glu Asp Gln Val Asp Pro Arg Leu Ile Asp Gly Lys Arg Arg Arg
1               5                   10                  15

Arg Arg Arg Arg Arg Arg Asp Asp Asp
            20                  25

<210> SEQ ID NO 84
```

```
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(22)
<223> OTHER INFORMATION: Some arginines may be missing.

<400> SEQUENCE: 84

Met Glu Asp Gln Val Asp Pro Arg Leu Ile Asp Gly Lys Arg Arg Arg
1               5                   10                  15

Arg Arg Arg Arg Arg Arg Lys Lys Lys
            20                  25

<210> SEQ ID NO 85
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 85

Gln Pro Glu Leu Ala Pro Glu Asp Pro Glu Asp Arg Arg Arg Arg Arg
1               5                   10                  15

Arg Arg Arg Arg
            20

<210> SEQ ID NO 86
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 86

Gln Pro Glu Leu Ala Pro Glu Asp Pro Glu Asp Arg Arg Arg Arg Arg
1               5                   10                  15

Arg Arg Arg Arg Phe Phe Phe
            20

<210> SEQ ID NO 87
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 87

Gln Pro Glu Leu Ala Pro Glu Asp Pro Glu Asp Arg Arg Arg Arg Arg
1               5                   10                  15

Arg Arg Arg Arg Tyr Tyr Tyr
            20
```

```
<210> SEQ ID NO 88
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 88

Gln Pro Glu Leu Ala Pro Glu Asp Pro Glu Asp Arg Arg Arg Arg Arg
1               5                   10                  15

Arg Arg Arg Arg Leu Leu Leu
            20

<210> SEQ ID NO 89
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 89

Gln Pro Glu Leu Ala Pro Glu Asp Pro Glu Asp Arg Arg Arg Arg Arg
1               5                   10                  15

Arg Arg Arg Arg Asp Asp Asp
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(20)
<223> OTHER INFORMATION: Some arginines may be missing.

<400> SEQUENCE: 90

Gln Pro Glu Leu Ala Pro Glu Asp Pro Glu Asp Arg Arg Arg Arg Arg
1               5                   10                  15

Arg Arg Arg Arg Lys Lys Lys
            20

<210> SEQ ID NO 91
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 91

Met Gln Pro Glu Leu Ala Pro Glu Asp Pro Glu Asp Arg Arg Arg Arg
1               5                   10                  15

Arg Arg Arg Arg Arg
            20
```

<210> SEQ ID NO 92
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 92

Met Gln Pro Glu Leu Ala Pro Glu Asp Pro Glu Asp Arg Arg Arg Arg
1               5                   10                  15

Arg Arg Arg Arg Arg Phe Phe Phe
            20

<210> SEQ ID NO 93
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 93

Met Gln Pro Glu Leu Ala Pro Glu Asp Pro Glu Asp Arg Arg Arg Arg
1               5                   10                  15

Arg Arg Arg Arg Arg Tyr Tyr Tyr
            20

<210> SEQ ID NO 94
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 94

Met Gln Pro Glu Leu Ala Pro Glu Asp Pro Glu Asp Arg Arg Arg Arg
1               5                   10                  15

Arg Arg Arg Arg Arg Leu Leu Leu
            20

<210> SEQ ID NO 95
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 95

Met Gln Pro Glu Leu Ala Pro Glu Asp Pro Glu Asp Arg Arg Arg Arg
1               5                   10                  15

Arg Arg Arg Arg Arg Asp Asp Asp
            20

```
<210> SEQ ID NO 96
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(21)
<223> OTHER INFORMATION: Some arginines may be missing.

<400> SEQUENCE: 96

Met Gln Pro Glu Leu Ala Pro Glu Asp Pro Glu Asp Arg Arg Arg Arg
1               5                   10                  15

Arg Arg Arg Arg Arg Lys Lys Lys
            20

<210> SEQ ID NO 97
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 97

His His His His His His Arg Arg Arg Arg Arg Arg Arg Arg Arg
1               5                   10                  15

<210> SEQ ID NO 98
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 98

His His His His His His Arg Arg Arg Arg Arg Arg Arg Arg Arg Phe
1               5                   10                  15

Phe Phe

<210> SEQ ID NO 99
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 99

His His His His His His Arg Arg Arg Arg Arg Arg Arg Arg Arg Tyr
1               5                   10                  15

Tyr Tyr

<210> SEQ ID NO 100
```

```
<400> SEQUENCE: 100

000

<210> SEQ ID NO 101
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 101

His His His His His His Arg Arg Arg Arg Arg Arg Arg Arg Arg Leu
1               5                   10                  15

Leu Leu

<210> SEQ ID NO 102
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 102

His His His His His His Arg Arg Arg Arg Arg Arg Arg Arg Arg Asp
1               5                   10                  15

Asp Asp

<210> SEQ ID NO 103
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(15)
<223> OTHER INFORMATION: Some arginines may be missing.

<400> SEQUENCE: 103

His His His His His His Arg Arg Arg Arg Arg Arg Arg Arg Arg Lys
1               5                   10                  15

Lys Lys

<210> SEQ ID NO 104
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 104

Met His His His His His His Arg Arg Arg Arg Arg Arg Arg Arg Arg
1               5                   10                  15
```

```
<210> SEQ ID NO 105
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 105

Met His His His His His His Arg Arg Arg Arg Arg Arg Arg Arg
1               5                   10                  15
Phe Phe Phe

<210> SEQ ID NO 106
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 106

Met His His His His His His Arg Arg Arg Arg Arg Arg Arg Arg
1               5                   10                  15
Tyr Tyr Tyr

<210> SEQ ID NO 107
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 107

Met His His His His His His Arg Arg Arg Arg Arg Arg Arg Arg
1               5                   10                  15
Leu Leu Leu

<210> SEQ ID NO 108
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 108

Met His His His His His His Arg Arg Arg Arg Arg Arg Arg Arg
1               5                   10                  15
Asp Asp Asp

<210> SEQ ID NO 109
<211> LENGTH: 19
<212> TYPE: PRT
```

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(16)
<223> OTHER INFORMATION: Some arginines may be missing.

<400> SEQUENCE: 109

Met His His His His His His Arg Arg Arg Arg Arg Arg Arg Arg Arg
1               5                   10                  15

Lys Lys Lys

<210> SEQ ID NO 110
<211> LENGTH: 18
<212> TYPE: DNA
<213> ORGANISM: Artificial Sequence
<220> FEATURE:
<223> OTHER INFORMATION: Synthetic

<400> SEQUENCE: 110
catcaccatc accatcac                                                 18

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
gactacaagg acgacgacga caag                                          24

<210> SEQ ID NO 112
<211> LENGTH: 30
<212> TYPE: DNA
<213> ORGANISM: Artificial Sequence
<220> FEATURE:
<223> OTHER INFORMATION: Synthetic

<400> SEQUENCE: 112
gagcagaagc tgatcagcga ggaggacctg                                    30

<210> SEQ ID NO 113
<211> LENGTH: 24
<212> TYPE: DNA
<213> ORGANISM: Artificial Sequence
<220> FEATURE:
<223> OTHER INFORMATION: Synthetic

<400> SEQUENCE: 113
tggagccacc cccagttcga gaag                                          24

<210> SEQ ID NO 114
<211> LENGTH: 48
<212> TYPE: DNA
<213> ORGANISM: Artificial Sequence
<220> FEATURE:
<223> OTHER INFORMATION: Synthetic

<400> SEQUENCE: 114
tgcagcccct tcgaggtgca ggtgagcccc gaggccggcg cccagaag                48

<210> SEQ ID NO 115
<211> LENGTH: 33
<212> TYPE: DNA

<210> SEQ ID NO 115
<211> LENGTH: 33
<212> TYPE: DNA
<213> ORGANISM: Artificial Sequence
<220> FEATURE:
<223> OTHER INFORMATION: Synthetic

<400> SEQUENCE: 115
atggccagca tgaccggcgg ccagcagatg ggc          33

<210> SEQ ID NO 116
<211> LENGTH: 33
<212> TYPE: DNA
<213> ORGANISM: Artificial Sequence
<220> FEATURE:
<223> OTHER INFORMATION: Synthetic

<400> SEQUENCE: 116
tacaccgaca tcgagatgaa ccgcctgggc aag          33

<210> SEQ ID NO 117
<211> LENGTH: 27
<212> TYPE: DNA
<213> ORGANISM: Artificial Sequence
<220> FEATURE:
<223> OTHER INFORMATION: Synthetic

<400> SEQUENCE: 117
tacccctacg acgtgcccga ctacgcc                 27

<210> SEQ ID NO 118
<211> LENGTH: 36
<212> TYPE: DNA
<213> ORGANISM: Artificial Sequence
<220> FEATURE:
<223> OTHER INFORMATION: Synthetic

<400> SEQUENCE: 118
gaggaccagg tggaccccccg cctgatcgac ggcaag      36

<210> SEQ ID NO 119
<211> LENGTH: 33
<212> TYPE: DNA
<213> ORGANISM: Artificial Sequence
<220> FEATURE:
<223> OTHER INFORMATION: Synthetic

<400> SEQUENCE: 119
cagcccgagc tggcccccga ggaccccgag gac          33

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

His His His His His His
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

```
Asp Tyr Lys Asp Asp Asp Asp Lys
1               5
```

<210> SEQ ID NO 122
<211> LENGTH: 10
<212> TYPE: PRT
<213> ORGANISM: Artificial Sequence
<220> FEATURE:
<223> OTHER INFORMATION: Synthetic

<400> SEQUENCE: 122

```
Glu Gln Lys Leu Ile Ser Glu Glu Asp Leu
1               5                   10
```

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

```
Trp Ser His Pro Gln Phe Glu Lys
1               5
```

<210> SEQ ID NO 124
<211> LENGTH: 16
<212> TYPE: PRT
<213> ORGANISM: Artificial Sequence
<220> FEATURE:
<223> OTHER INFORMATION: Synthetic

<400> SEQUENCE: 124

```
Cys Ser Pro Phe Glu Val Gln Val Ser Pro Glu Ala Gly Ala Gln Lys
1               5                   10                  15
```

<210> SEQ ID NO 125
<211> LENGTH: 11
<212> TYPE: PRT
<213> ORGANISM: Artificial Sequence
<220> FEATURE:
<223> OTHER INFORMATION: Synthetic

<400> SEQUENCE: 125

```
Met Ala Ser Met Thr Gly Gly Gln Gln Met Gly
1               5                   10
```

<210> SEQ ID NO 126
<211> LENGTH: 11
<212> TYPE: PRT
<213> ORGANISM: Artificial Sequence
<220> FEATURE:
<223> OTHER INFORMATION: Synthetic

<400> SEQUENCE: 126

```
Tyr Thr Asp Ile Glu Met Asn Arg Leu Gly Lys
1               5                   10
```

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127

```
Tyr Pro Tyr Asp Val Pro Asp Tyr Ala
```

```
1               5

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Glu Asp Gln Val Asp Pro Arg Leu Ile Asp Gly Lys
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic

<400> SEQUENCE: 129

Gln Pro Glu Leu Ala Pro Glu Asp Pro Glu Asp
1               5                   10

<210> SEQ ID NO 130
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n can be a or g.

<400> SEQUENCE: 130 gccnccatgg                                                            10

<210> SEQ ID NO 131
<211> LENGTH: 9
<212> TYPE: RNA
<213> ORGANISM: Artificial Sequence
<220> FEATURE:
<223> OTHER INFORMATION: Synthetic

<400> SEQUENCE: 131 uaaggaggu                                                              9

<210> SEQ ID NO 132
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(19)
<223> OTHER INFORMATION: n can be a, c, g, or u.
<220> FEATURE:
<221> NAME/KEY: misc_feature
<222> LOCATION: (15)..(19)
<223> OTHER INFORMATION: Some may be missing.

<400> SEQUENCE: 132
uaaggaggun nnnnnnnnna ug                                              22

<210> SEQ ID NO 133
<211> LENGTH: 9
```

```
<212> TYPE: DNA
<213> ORGANISM: Artificial Sequence
<220> FEATURE:
<223> OTHER INFORMATION: Synthetic

<400> SEQUENCE: 133 ataaataaa                                                                   9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ile Asn Lys
1

<210> SEQ ID NO 135
<211> LENGTH: 9
<212> TYPE: DNA
<213> ORGANISM: Artificial Sequence
<220> FEATURE:
<223> OTHER INFORMATION: Synthetic

<400> SEQUENCE: 135 tttatttat                                                                   9

<210> SEQ ID NO 136
<211> LENGTH: 111
<212> TYPE: DNA
<213> ORGANISM: Artificial Sequence
<220> FEATURE:
<223> OTHER INFORMATION: Synthetic

<400> SEQUENCE: 136
gaattctaat acgactcact atagggttaa ctttaagaag gagatataca tatggaacaa          60
aaattaatct cggaagagga tttggcagat tctgatatta atattaaaac c                  111

<210> SEQ ID NO 137
<211> LENGTH: 30
<212> TYPE: DNA
<213> ORGANISM: Artificial Sequence
<220> FEATURE:
<223> OTHER INFORMATION: Synthetic

<400> SEQUENCE: 137
agcttcatta atgatggtga tggtggtgac                                           30

<210> SEQ ID NO 138
<211> LENGTH: 94
<212> TYPE: DNA
<213> ORGANISM: Artificial Sequence
<220> FEATURE:
<223> OTHER INFORMATION: Synthetic

<400> SEQUENCE: 138
ggatcctaat acgactcact atagggagac caccatggaa caaaaattaa tatcggaaga          60
ggatttgaat gtttctccat acaggtcacg ggga                                     94

<210> SEQ ID NO 139
<211> LENGTH: 51
<212> TYPE: DNA
<213> ORGANISM: Artificial Sequence
```

<220> FEATURE:
<223> OTHER INFORMATION: Synthetic

<400> SEQUENCE: 139
ttattaatga tggtgatggt ggtgttctgt aggaatggta tctcgttttt c    51

<210> SEQ ID NO 140
<211> LENGTH: 60
<212> TYPE: DNA
<213> ORGANISM: Artificial Sequence
<220> FEATURE:
<223> OTHER INFORMATION: Synthetic

<400> SEQUENCE: 140
ttattaatga tggtgatggt ggtgtttatt tatttctgta ggaatggtat ctcgtttttc    60

<210> SEQ ID NO 141
<211> LENGTH: 114
<212> TYPE: DNA
<213> ORGANISM: Artificial Sequence
<220> FEATURE:
<223> OTHER INFORMATION: Synthetic

<400> SEQUENCE: 141
ggatcctaat acgactcact atagggagac caccatggga caccaccatc accatcacgg    60
agattacaaa gatgacgatg acaaagagga gccgcagtca gatcctagcg tcga    114

<210> SEQ ID NO 142
<211> LENGTH: 68
<212> TYPE: DNA
<213> ORGANISM: Artificial Sequence
<220> FEATURE:
<223> OTHER INFORMATION: Synthetic

<400> SEQUENCE: 142
attattacaa atcctcttcc gagattaatt tttgttcgtc tgagtcaggc ccttctgtct    60
tgaacatg    68

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
ctcattcagc tctcggaaca tctcgaagcg    30

<210> SEQ ID NO 144
<211> LENGTH: 115
<212> TYPE: DNA
<213> ORGANISM: Artificial Sequence
<220> FEATURE:
<223> OTHER INFORMATION: Synthetic

<400> SEQUENCE: 144
ggatcctaat acgactcact atagggagac caccatgcac caccatcacc atcacggagg    60
agattacaaa gatgacgatg acaaagtttc tccatacagg tcacggggag ccaat    115

<210> SEQ ID NO 145
<211> LENGTH: 67
<212> TYPE: DNA
<213> ORGANISM: Artificial Sequence
<220> FEATURE:

-continued

<223> OTHER INFORMATION: Synthetic

<400> SEQUENCE: 145
attattacaa atcctcttcc gagattaatt tttgttcact tctgccttct gtaggaatgg    60
tatctcg                                                              67

<210> SEQ ID NO 146
<211> LENGTH: 99
<212> TYPE: DNA
<213> ORGANISM: Artificial Sequence
<220> FEATURE:
<223> OTHER INFORMATION: Synthetic

<400> SEQUENCE: 146
ggatcctaat acgactcact atagggagac caccatgggc tacaccgaca tcgagatgaa    60
ccgcctggca aggtttctcc atacaggtca cggggagcc                           99

<210> SEQ ID NO 147
<211> LENGTH: 59
<212> TYPE: DNA
<213> ORGANISM: Artificial Sequence
<220> FEATURE:
<223> OTHER INFORMATION: Synthetic

<400> SEQUENCE: 147
ttattacagc agcttgtgca ggtcgctgaa ggtacttctg ccttctgtag gaatgtatc     59

<210> SEQ ID NO 148
<211> LENGTH: 11
<212> TYPE: PRT
<213> ORGANISM: Artificial Sequence
<220> FEATURE:
<223> OTHER INFORMATION: Synthetic

<400> SEQUENCE: 148

Tyr Thr Asp Ile Glu Met Asn Arg Leu Gly Lys
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetic

<400> SEQUENCE: 149

Thr Phe Ser Asp Leu His Lys Leu Leu
1               5

<210> SEQ ID NO 150
<211> LENGTH: 12
<212> TYPE: PRT
<213> ORGANISM: Artificial Sequence
<220> FEATURE:
<223> OTHER INFORMATION: Synthetic

<400> SEQUENCE: 150

Met Tyr Thr Asp Ile Glu Met Asn Arg Leu Gly Lys
1               5                   10

<210> SEQ ID NO 151
<211> LENGTH: 9
<212> TYPE: PRT
<213> ORGANISM: Artificial Sequence
<220> FEATURE:

<223> OTHER INFORMATION: Synthetic

<400> SEQUENCE: 151

Thr Phe Ser Asp Leu Trp Lys Leu Leu
1               5

<210> SEQ ID NO 152
<211> LENGTH: 18
<212> TYPE: PRT
<213> ORGANISM: Artificial Sequence
<220> FEATURE:
<223> OTHER INFORMATION: Synthetic

<400> SEQUENCE: 152

Met Asp Tyr Lys Asp Asp Asp Asp Lys Arg Arg Arg Arg Arg Phe
1               5                   10                  15

Phe Phe

<210> SEQ ID NO 153
<211> LENGTH: 14
<212> TYPE: PRT
<213> ORGANISM: Artificial Sequence
<220> FEATURE:
<223> OTHER INFORMATION: Synthetic

<400> SEQUENCE: 153

Met Asp Tyr Lys Asp Asp Asp Asp Lys Arg Arg Arg Arg Arg
1               5                   10

<210> SEQ ID NO 154
<211> LENGTH: 78
<212> TYPE: DNA
<213> ORGANISM: Artificial Sequence
<220> FEATURE:
<223> OTHER INFORMATION: Synthetic

<400> SEQUENCE: 154
taatacgact cactataggg aggaggacag ctatggacta caaggacgac gatgacaaga      60
ggaggaggag gaggaggt                                                   78

<210> SEQ ID NO 155
<211> LENGTH: 81
<212> TYPE: DNA
<213> ORGANISM: Artificial Sequence
<220> FEATURE:
<223> OTHER INFORMATION: Synthetic

<400> SEQUENCE: 155 caaaaaccc ctcaagaccc gtttagaggc cccaaggggt tatgctagtc agaagaagaa       60
cctcctcctc ctcctcctct t                                               81

<210> SEQ ID NO 156
<211> LENGTH: 80
<212> TYPE: DNA
<213> ORGANISM: Artificial Sequence
<220> FEATURE:
<223> OTHER INFORMATION: Synthetic

<400> SEQUENCE: 156
taatacgact cactataggg aggaggacag ctatggacta caaggacgac gatgacaaga      60
cgacacagga agcagattct                                                 80

<210> SEQ ID NO 157

```
<211> LENGTH: 54
<212> TYPE: DNA
<213> ORGANISM: Artificial Sequence
<220> FEATURE:
<223> OTHER INFORMATION: Synthetic

<400> SEQUENCE: 157
tttttatgcg tagtctggta cgtcgtatgg gtagtgttca ggtggacttt tggg      54

<210> SEQ ID NO 158
<211> LENGTH: 54
<212> TYPE: DNA
<213> ORGANISM: Artificial Sequence
<220> FEATURE:
<223> OTHER INFORMATION: Synthetic

<400> SEQUENCE: 158
tttttatgcg tagtctggta cgtcgtatgg gtagccttca ggtggacttt tggg      54

<210> SEQ ID NO 159
<211> LENGTH: 102
<212> TYPE: PRT
<213> ORGANISM: Artificial Sequence
<220> FEATURE:
<223> OTHER INFORMATION: Synthetic

<400> SEQUENCE: 159
```

Met Asp Tyr Lys Asp Asp Asp Lys Thr Thr Gln Glu Ala Asp Ser
 1               5                  10                  15

Ala Asn Thr Leu Gln Ile Ala Glu Ile Lys Glu Lys Ile Gly Thr Arg
            20                  25                  30

Ser Ala Glu Asp Pro Val Ser Glu Val Pro Ala Val Ser Gln His Pro
        35                  40                  45

Arg Thr Lys Ser Ser Arg Leu Gln Gly Ser Ser Leu Ser Ser Glu Ser
    50                  55                  60

Ala Arg His Lys Ala Val Glu Phe Ser Ser Gly Ala Lys Ser Pro Ser
65                  70                  75                  80

Lys Ser Gly Ala Gln Thr Pro Lys Ser Pro Pro Glu His Tyr Pro Tyr
                85                  90                  95

Asp Val Pro Asp Tyr Ala
            100

```
<210> SEQ ID NO 160
<211> LENGTH: 29
<212> TYPE: PRT
<213> ORGANISM: Artificial Sequence
<220> FEATURE:
<223> OTHER INFORMATION: Synthetic

<400> SEQUENCE: 160
```

Met Asp Tyr Lys Asp Asp Asp Lys Thr Thr Gln Glu Ala Asp Ser
 1               5                  10                  15

Ala Asn Thr Leu Gln Ile Ala Glu Ile Lys Asp Trp Asn
            20                  25

```
<210> SEQ ID NO 161
<211> LENGTH: 55
<212> TYPE: PRT
<213> ORGANISM: Artificial Sequence
<220> FEATURE:
<223> OTHER INFORMATION: Synthetic

<400> SEQUENCE: 161
```

Met Asp Tyr Lys Asp Asp Asp Lys Thr Thr Gln Glu Ala Asp Ser
1               5                   10                  15

Ala Asn Thr Leu Gln Ile Ala Glu Ile Lys Glu Lys Ile Gly Thr Arg
                20                  25                  30

Ser Ala Glu Asp Pro Val Ser Glu Val Pro Ala Val Ser Gln His Pro
                35                  40                  45

Arg Thr Lys Ser Ser Arg Leu
    50              55

<210> SEQ ID NO 162
<211> LENGTH: 84
<212> TYPE: PRT
<213> ORGANISM: Artificial Sequence
<220> FEATURE:
<223> OTHER INFORMATION: Synthetic

<400> SEQUENCE: 162

Met Asp Tyr Lys Asp Asp Asp Lys Thr Thr Gln Glu Ala Asp Ser
1               5                   10                  15

Ala Asn Thr Leu Gln Ile Ala Glu Ile Lys Glu Lys Ile Gly Thr Arg
                20                  25                  30

Ser Ala Glu Asp Pro Val Ser Glu Val Pro Ala Val Ser Gln His Pro
                35                  40                  45

Arg Thr Lys Ser Ser Arg Leu Gln Gly Ser Ser Leu Ser Ser Glu Ser
    50              55                  60

Ala Arg His Lys Ala Val Glu Phe Ser Ser Gly Ala Lys Ser Pro Ser
65                  70                  75                  80

Lys Ser Gly Ala

<210> SEQ ID NO 163
<211> LENGTH: 102
<212> TYPE: PRT
<213> ORGANISM: Artificial Sequence
<220> FEATURE:
<223> OTHER INFORMATION: Synthetic

<400> SEQUENCE: 163

Met Asp Tyr Lys Asp Asp Asp Lys Thr Thr Gln Glu Ala Asp Ser
1               5                   10                  15

Ala Asn Thr Leu Gln Ile Ala Glu Ile Lys Glu Lys Ile Gly Thr Arg
                20                  25                  30

Ser Ala Glu Asp Pro Val Ser Glu Val Pro Ala Val Ser Gln His Pro
                35                  40                  45

Arg Thr Lys Ser Ser Arg Leu Gln Gly Ser Ser Leu Ser Ser Glu Ser
    50              55                  60

Ala Arg His Lys Ala Val Glu Phe Ser Ser Gly Ala Lys Ser Pro Ser
65                  70                  75                  80

Lys Ser Gly Ala Gln Thr Pro Lys Ser Pro Pro Glu Gly Tyr Pro Tyr
                85                  90                  95

Asp Val Pro Asp Tyr Ala
            100

<210> SEQ ID NO 164
<211> LENGTH: 5
<212> TYPE: PRT
<213> ORGANISM: Artificial Sequence
<220> FEATURE:
<223> OTHER INFORMATION: Synthetic

<400> SEQUENCE: 164

```
Ala Val Tyr Lys Trp
1               5

<210> SEQ ID NO 165
<211> LENGTH: 33
<212> TYPE: RNA
<213> ORGANISM: Artificial Sequence
<220> FEATURE:
<223> OTHER INFORMATION: Synthetic

<400> SEQUENCE: 165
auguacacua aacaugauga uauccgaaaa uga                                    33

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Met Tyr Thr Lys Asp His Asp Ile Arg Lys
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic

<400> SEQUENCE: 167

Lys Arg Ile Asp Asp His Lys Thr Tyr Met
1               5                   10
```